US008921338B2

(12) United States Patent
Lebreton

(10) Patent No.: US 8,921,338 B2
(45) Date of Patent: *Dec. 30, 2014

(54) FLUID COMPOSITIONS FOR IMPROVING SKIN CONDITIONS

(71) Applicant: Allergan Industrie SAS, Pringy (FR)

(72) Inventor: Pierre F. Lebreton, Annecy (FR)

(73) Assignee: Allergan Industrie, SAS, Pringy (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/077,980

(22) Filed: Nov. 12, 2013

(65) Prior Publication Data

US 2014/0066401 A1 Mar. 6, 2014

Related U.S. Application Data

(63) Continuation of application No. 12/777,106, filed on May 10, 2010, now Pat. No. 8,586,562.

(60) Provisional application No. 61/313,664, filed on Mar. 12, 2010.

(51) Int. Cl.
| A61K 31/728 | (2006.01) |
| A61K 31/715 | (2006.01) |
| A61K 8/73 | (2006.01) |
| A61Q 19/00 | (2006.01) |
| A61K 8/34 | (2006.01) |
| A61Q 19/08 | (2006.01) |

(52) U.S. Cl.
CPC . *A61K 8/73* (2013.01); *A61Q 19/00* (2013.01); *A61K 8/345* (2013.01); *A61K 2800/91* (2013.01); *A61Q 19/08* (2013.01); *A61K 8/735* (2013.01)
USPC .......................... 514/54; 536/123.1; 536/124

(58) Field of Classification Search
USPC ................................ 514/54; 536/123.1, 124
See application file for complete search history.

(56) References Cited

U.S. PATENT DOCUMENTS

| 2,128,827 A | 8/1938 | Killian |
| 3,548,056 A | 12/1970 | Eigen et al. |
| 3,763,009 A | 10/1973 | Suzuki et al. |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs |
| 4,642,117 A | 2/1987 | Nguyen et al. |
| 4,713,448 A | 12/1987 | Balazs |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leshchiner et al. |
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto et al. |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | della Valle |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai |
| 5,880,107 A | 3/1999 | Buenter |
| 5,886,042 A | 3/1999 | Yu et al. |

(Continued)

FOREIGN PATENT DOCUMENTS

| CA | 949965 | 6/1974 |
| EP | 0273823 | 7/1988 |

(Continued)

OTHER PUBLICATIONS

Aesthetic Buyers Guide, "Juvéderm Raises Standards" Jan./Feb. 2007 (5 pp.), www.miinews.com.
Adams, "An Analysis of Clinical Studies of the Uses of Crosslinked Hyaluronan, Hylan, in the Treatment of Osteoarthritis", J. Rheumatol Suppl., Aug. 1993; 39:16-8.
Albano, Emanuele, et al., "Hydroxyethyl Radicals in Ethanol Hepatotoxicity," Frontiers in Bioscience 4:533-540 (1999).
Allemann et al., "Hyaluronic acid gel (JUVEDERM) preparations in the treatment of facial wrinkles and folds", 2008, Clinical Interventions in Aging, vol. 3, No. 4, pp. 629-634.
Antunes, Alberto A., et al., "Efficacy of Intrarectal Lidocaine Hydrochloride Gel for Pain control in Patients Undergoing Transrectal Prostate Biopsy", International Braz J Urol, vol. 30(5): 380-383, Sep.-Oct. 2004.

(Continued)

*Primary Examiner* — Shaojia Anna Jiang
*Assistant Examiner* — Michael C Henry
(74) *Attorney, Agent, or Firm* — Linda Allyson Nassif

(57) ABSTRACT

The present specification discloses fluid compositions comprising a matrix polymer and stabilizing component, methods of making such fluid compositions, and methods of treating skin conditions in an individual using such fluid compositions.

14 Claims, 3 Drawing Sheets

(56) References Cited

U.S. PATENT DOCUMENTS

| | | |
|---|---|---|
| 5,935,164 A | 8/1999 | Iversen |
| 5,972,326 A | 10/1999 | Galin et al. |
| 5,980,930 A | 11/1999 | Fenton et al. |
| 6,013,679 A | 1/2000 | Kuo et al. |
| 6,066,325 A | 5/2000 | Wallace et al. |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | chin |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci et al. |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,166,570 B2 | 1/2007 | Hunter et al. |
| 7,192,984 B2 | 3/2007 | Berg |
| 7,196,180 B2 | 3/2007 | Aeschlimann |
| 7,314,636 B2 | 1/2008 | Caseres et al. |
| 7,491,709 B2 | 2/2009 | Carey |
| 7,741,476 B2 | 6/2010 | Lebreton |
| 7,902,171 B2 | 3/2011 | Reinmuller et al. |
| 8,052,990 B2 | 11/2011 | Hermitte et al. |
| 8,124,120 B2 | 2/2012 | Sadozai et al. |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 | 3/2013 | Stroumpoulis et al. |
| 8,394,783 B2 | 3/2013 | Stroumpoulis et al. |
| 8,394,784 B2 | 3/2013 | Stroumpoulis et al. |
| 8,455,465 B2 | 6/2013 | Molliard |
| 8,513,216 B2 | 8/2013 | Stroumpoulis et al. |
| 8,524,213 B2 | 9/2013 | Leshchiner et al. |
| 8,563,532 B2 | 10/2013 | Lebreton |
| 8,575,129 B2 | 11/2013 | Bellini |
| 8,586,562 B2 | 11/2013 | Lebreton |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0226936 A1 | 10/2005 | Agerup |
| 2005/0271729 A1 | 12/2005 | Wang |
| 2005/0281880 A1 | 12/2005 | Wang |
| 2005/0287180 A1 | 12/2005 | Chen |
| 2006/0040894 A1 | 2/2006 | Hunter et al. |
| 2006/0095137 A1 | 5/2006 | Chung et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Biterman et al. |
| 2008/0207794 A1 | 8/2008 | Wright et al. |
| 2008/0241252 A1 | 10/2008 | Lyons |
| 2008/0268051 A1 | 10/2008 | Lyons et al. |
| 2008/0274946 A1 | 11/2008 | Giampapa |
| 2008/0279806 A1 | 11/2008 | Cho |
| 2008/0293637 A1 | 11/2008 | Schroeder et al. |
| 2009/0017091 A1 | 1/2009 | Daniloff et al. |
| 2009/0018102 A1 | 1/2009 | Moutet |
| 2009/0022808 A1 | 1/2009 | Championn |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel |
| 2009/0148527 A1 | 6/2009 | Robinson |
| 2009/0155314 A1 | 6/2009 | Tezel |
| 2009/0155362 A1 | 6/2009 | Longin |
| 2009/0169615 A1 | 7/2009 | Pinsky |
| 2009/0263447 A1 | 10/2009 | Asius et al. |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Herber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0255068 A1 | 10/2010 | Stroumpoulis et al. |
| 2010/0316683 A1 | 12/2010 | Piron |
| 2011/0034684 A1 | 2/2011 | Yokokawa |
| 2011/0077737 A1 | 3/2011 | Stroumpoulis et al. |
| 2011/0118206 A1 | 5/2011 | Lebreton |
| 2011/0171286 A1 | 7/2011 | Cecile et al. |
| 2011/0171311 A1 | 7/2011 | Gousse et al. |
| 2011/0172180 A1 | 7/2011 | Gousse et al. |
| 2011/0229574 A1 | 9/2011 | Guillen et al. |
| 2012/0010146 A1 | 1/2012 | Han et al. |
| 2012/0034462 A1 | 2/2012 | Stroumpoulis et al. |
| 2012/0071437 A1 | 3/2012 | Stroumpoulis et al. |
| 2012/0095206 A1 | 4/2012 | Chen |
| 2012/0100217 A1 | 4/2012 | Green |
| 2012/0164098 A1 | 6/2012 | Schroeder et al. |
| 2012/0172328 A1 | 7/2012 | Lebreton |
| 2012/0189589 A1 | 7/2012 | Van Epps et al. |
| 2012/0189590 A1 | 7/2012 | Van Epps et al. |
| 2012/0189708 A1 | 7/2012 | Van Epps et al. |
| 2012/0190644 A1 | 7/2012 | D'este |
| 2012/0208890 A1 | 8/2012 | Gousse et al. |
| 2012/0225842 A1 | 9/2012 | Cecile et al. |
| 2012/0232030 A1 | 9/2012 | Gousse et al. |
| 2013/0023658 A1 | 1/2013 | Stroumpoulis et al. |

(56) References Cited

U.S. PATENT DOCUMENTS

| | | |
|---|---|---|
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0123210 A1 | 5/2013 | Liu |
| 2013/0131011 A1 | 5/2013 | Lebreton |
| 2013/0136780 A1 | 5/2013 | Tezel et al. |
| 2013/0203696 A1 | 8/2013 | Liu |
| 2013/0209532 A1 | 8/2013 | Stroumpoulis et al. |
| 2013/0210760 A1 | 8/2013 | Liu |
| 2013/0237615 A1 | 9/2013 | Meunier |
| 2013/0244943 A1 | 9/2013 | Yu et al. |
| 2013/0244970 A1 | 9/2013 | Lebreton |
| 2013/0274222 A1 | 10/2013 | Home |
| 2014/0011980 A1 | 1/2014 | Chitre et al. |
| 2014/0011990 A1 | 1/2014 | Lebreton |

FOREIGN PATENT DOCUMENTS

| | | |
|---|---|---|
| EP | 0416250 | 3/1991 |
| EP | 0416846 | 3/1991 |
| EP | 1247522 | 10/2002 |
| EP | 1419792 | 4/2003 |
| EP | 1398131 | 3/2004 |
| EP | 1532991 | 5/2005 |
| EP | 1726299 | 11/2006 |
| EP | 2236523 | 10/2010 |
| FR | 2733427 | 10/1996 |
| FR | 2920000 | 2/2009 |
| FR | 2924615 | 6/2009 |
| JP | 55-153711 | 11/1980 |
| JP | 2002080501 | 3/2002 |
| JP | 2007063177 | 3/2007 |
| WO | 8600079 | 1/1986 |
| WO | 8600912 | 2/1986 |
| WO | 9200105 | 1/1992 |
| WO | 9220349 | 11/1992 |
| WO | 9401468 | 1/1994 |
| WO | 9402517 | 2/1994 |
| WO | 9633751 | 1/1996 |
| WO | 9704012 | 2/1997 |
| WO | 9835639 | 8/1998 |
| WO | 9835640 | 8/1998 |
| WO | 0001428 | 1/2000 |
| WO | 0179342 | 10/2001 |
| WO | 0205753 | 1/2002 |
| WO | 0206350 | 1/2002 |
| WO | 0209792 | 2/2002 |
| WO | 0217713 | 3/2002 |
| WO | 03007782 | 1/2003 |
| WO | 2004020473 | 3/2004 |
| WO | 2004022603 | 3/2004 |
| WO | 2004073759 | 9/2004 |
| WO | WO 2004/073759 A1 * | 9/2004 |
| WO | 2004092223 | 10/2004 |
| WO | 2005040224 | 5/2005 |
| WO | 2005067944 | 7/2005 |
| WO | 2005074913 | 8/2005 |
| WO | 2005112888 | 12/2005 |
| WO | 2006023645 | 3/2006 |
| WO | 2006067608 | 6/2006 |
| WO | 2007018124 | 2/2007 |
| WO | 2007070617 | 6/2007 |
| WO | 2007077399 | 7/2007 |
| WO | 2007128923 | 11/2007 |
| WO | 2007136738 | 11/2007 |
| WO | 2008034176 | 3/2008 |
| WO | 2008068297 | 6/2008 |
| WO | 2008072230 | 6/2008 |
| WO | 2008077172 | 7/2008 |
| WO | 2008098019 | 8/2008 |
| WO | 2008139122 | 11/2008 |
| WO | 2008148967 | 12/2008 |
| WO | 2008157608 | 12/2008 |
| WO | 2009024719 | 2/2009 |
| WO | 2009026158 | 2/2009 |
| WO | 2009028764 | 3/2009 |
| WO | 2009034559 | 3/2009 |
| WO | 2009073437 | 6/2009 |
| WO | 2010003797 | 1/2010 |
| WO | 2010027471 | 3/2010 |
| WO | 2010028025 | 3/2010 |
| WO | 2010029344 | 3/2010 |
| WO | 2010038771 | 4/2010 |
| WO | 2010051641 | 5/2010 |
| WO | 2010052430 | 5/2010 |
| WO | 2010053918 | 5/2010 |
| WO | 2010061005 | 6/2010 |
| WO | 2010015900 | 2/2011 |
| WO | 20121077055 | 6/2012 |

OTHER PUBLICATIONS

Atanassoff, Peter G., et al., "The Effect of Intradermal Administration of Lidocaine and Morphine on the Response to Thermal Stimulation", Anesth Analg 1997; 84:1340-3.

Baumann et al. "Juvederm vs. Zyplast Nasolabial Fold Study Group, Comparison of smooth-gel hyaluronic acid dermal fillers with cross-linked bovine collagen: a multicenter, double-masked, randomized, within-subject study." Dermatol. Surg. 33(Suppl 2): S128-S135 (2007).

Beasley et al. :Hyaluronic acid fillers: a comprehensive review. Facial Plast. Surg. 25(2): 86-94 (2009).

Beer "Dermal fillers and combinations of fillers for facial rejuvenation." Dermatol. Clin. 27(4): 427-432 (2009).

Belda, Jose I., et al., "Hyaluronic acid combined with mannitol to improve protection against free-radical endothelial damage: Experimental Model," J. Cataract Refract Surg 2005; 31:1213-1218.

Bircher, Andreas J., et al., "Delayed-type hypersensitivity to subcutaneous lidocaine with tolerance to articaine: confirmation by in vivo and in vitro tests", Contact Dermatitis 1996, 34, 387-389.

Bluel et al., "Evaluation of Reconstituted Collagen Tape as a Model for Chemically Modified Soft Tissues", Biomat. Med. De. Art. Org., 9(1):37-46 (1981).

Buck et al, "Injectable Fillers for our Facial Rejuvenation: a Review", Journal of Plastic, Reconstructive and Aesthetic Surgery, (2009), 62:11-18, XP002668828.

Capozzi et al., "Distant Migration of Silicone Gel From a Ruptured Breats Implant", Plastic and Reconstructive Surgery, 1978; 62:302-3.

Carlin, G., et al., "Effect of anti-inflammatory drugs on xanthine oxidase and xanthine oxidase induced depolymerization of hyaluronic acid," Agents and Actions. 16 (5):377-384 (1985).

Carruthers et al. "The science and art of dermal fillers for soft-tissue augmentation." J. Drugs Dermatol. 8(4): 335-350 (2009).

Champion, et al., "Role of Target Geometry in Phagocytosis", S. Proc. Nat. Acad. Sci., Mar. 2008, 2006, vol. 103, No. 13, pp. 4930-4934.

Chin, Thomas M., et al., "Allergic Hypersensitivity to Lidocaine Hydrochloride", International journal of Dermatology, vol. 19, Apr. 1980, pp. 147-148.

Chvapil, "Collagen Sponse: Theory and Practice of Medical Applications", J. Biomed Mater. Res., II, pp. 721-741 (1977).

Clark et al., "The Influence of Triamcinolone Acetonide on Joint Stiffness in the Rat", J Bone Joint Surg Am, 1971; 53:1409-1414.

Cohen et al., "Organization and Adhesive Properties of the Hyaluronan Pericellular Coat of Chondrocytes and Epithelial Cells", Biophys J., 2003; 85:1996-2005.

Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.

Deland, "Intrathecal Toxicity Studies with Benzyl Alcohol", Toxicol Appl Pharmacol, 1973; 25(2):153.

Desai et al., J Pharm Sci Feb. 1995; 84 (2): 212-5.

Eyre et al., Top Curr. Chem., 2005, vol. 247, pp. 207-229.

(56) References Cited

OTHER PUBLICATIONS

Falcone et al. "Crosslinked hyaluronic acid dermal fillers: a comparison of rheological properties." J Biomed Mater Res A. 87(1): 264-271 (2008).

Falcone et al. "Temporary polysaccharide dermal fillers: a model for persistence based on physical properties." Dermatol Surg. 35(8): 1238-1243 (2009).

Farley, Jon S., et al., "Diluting Lidocaine and Mepivacaine in Balanced Salt Solution Reduces the Pain of Intradermal Injection", Regional Anesthesia 19(1):48-51, 1994.

Frati, Elena, et al., "Degradation of hyaluronic acid by photosensitized riboflavin in vitro. Modulation of the effect by transition metals, radical quenchers, and metal chelators," Free Radical Biology Medicine 22 (7):1139-1144 (1997).

Fujinaga, Masahiko, et al., "Reproductive and Teratogenic Effects of Lidocaine in Sprague-Dawley Rats", Anesthesiology 65:626-632, 1986.

Gammaitoni, Arnold R., et al., "Pharmacokinetics and safety of continuously applied lidocaine patches 5%", Am J Health Syst Pharm, vol. 59, Nov. 15, 2002, pp. 2215-2220.

GinShiCel MH Hydroxy Propyl methyl Cellulose, Web Page http://www.ginshicel.cn/MHPC.html, Nov. 12, 2008.

Gold MH, "Use of Hyaluronic acid fillers for the treatment of the aging face." Clin. Interventions Aging 2(3): 369-376 (2007).

Goldberg "Breakthroughs in US dermal fillers for facial soft-tissue augmentation." J Cosmet Laser Ther. 11(4): 240-247 (2009).

Graefe, Hendrik, et al., "Sensitive and specific photometric determination of mannitol in human serum," Clin Chem Lab Med. 41 (8):1049-1055 (2003).

Grecomoro et al., "Intra-Articular Treatment with Sodium Hyaluronate in Gonarthrosis" a Controlled Clinical Trial Versus Placebo, Pharmatherapeutica, 1987; 5(2):137-41.

Grillo et al., "Thermal Reconstitution of Collagen from Solution and the Response to Its Heterologous Implantation", JSR II, No. 1, pp. 69-82 (1962).

Hassan et al., Effects of Adjuvants to local anaesthetics on their duration. III. Experimental studies of hyaluronic acid. Abstract Pub Med [Acta Anesthesiol Scand. May 1985; 29(4):384-8].

Hayashibara, "AA2G"; Sep. 23, 2007, http://web.archive.org/web/20079230720 10/http://www.hayashibara-intl.com/cosmetics/aa2g.html.

Helary et al., "Concentrated collagen hydrogels as dermal substitutes", Biomaterials 31 (2010) 481-490.

Helliwell, "Use of an Objective Measure of Articular Stiffness to Record Changes in Finger Joints After Intra-Articular Injection of Corticosteroid", An Theum Dis, 1997; 56:7.

Hertzberger-Ten et al., "Intra-Articular Steroids in Pauciarticular Juvenile Chronic Arthritis", Type I, Eur J Ped 1991; 150:170-172.

Hetherington, "Potential for Patient Harm From Intrathecal Administration of Preserved Solutions", Med J Aust, 2000, 173(3):p. 141.

Hurst, "Adhesive Arachnoiditis and Vascular Blockage Caused by Detergents and Other Chemical Irritants: an Experimental Study", J Path Bact, 1955; 70:167.

Intramed Mannitol 20% m/v Infusion, package insert, pp. 1-2 (2010) http://home.intekom.com/pharm/intramed/manit120.html.

Jones et al., "Intra-Articular Hyaluronic Acid Compared to Intra-Articular Triamcinolone Hexacetonide in Inflammatory Knee Osteoarthritis", Osteoarthritis Cartilage, 1995, 3:269-273.

Kablik et al. "Comparative physical properties of hyaluronic acid dermal fillers." Dermatol. Surg. Suppl. 35(Suppl. 1): 302-312 (2009).

Klein, "Skin Filling Collagen and Other Injectables of the Skin", Dermatologic Clinics, Jul. 2001, vol. 19, No. 3, pp. 491-588, ix, XP00919589.

Kulicke et al., "Visco-Elastic Properties of Sodium Hyaluronate Solutions," American Institue of Physics (2008).

Laeschke, "Biocompatibility of Microparticles into Soft Tissue Fillers", 23 Semin. Cutan. Med. Surg., 214 (2004).

Lamar et al., "Antifibrosis Effect of Novel Gels in Anterior Ciliary Sclerotomy *ACS)," ARVO 2002 abstract.

Levy, Jaime et al., "Lidocaine hypersensitivity after subconjunctival injection", Can J Ophthalmol 2006; 41:204-6.

Lindvall et al.; "Influence of Various Compunds on the Degradation of Hyaluronic Acid by a Myeloperoxidase System"; Chemico-Biological Interactions; vol. 90; pp. 1-12; 1994.

Lupo, MP., "Hyaluronic acid fillers in facial rejuvenation." Semin. Cutan. Med. Surg. 25(3): 122-126 (2006).

MacKley, et al., "Delayed-Type Hypersensitivity to Lidocaine", Arch Dermatol, vol. 139, Mar. 2003, pp. 343-346.

Mancinelli et al., "Intramuscular High-Dose Triamcinolone Acetonide in the Treatment of Severe Chronic Asthma", West J. Med, Nov. 1997: 167(5), 322-329.

Matsumoto, Alan H, et al., "Reducing the Discomfort of Lidocaine Administration through pH Buffering," Journal of Vascular and Interventional Radiology, Jan.-Feb. 1994, pp. 171-175.

McCarty et al., "Inflammatory Reaction After Intrasynovial Injection of Microcrystalline Adrenocorticosteroid Esters", Arthritis and Rheumatism, 7(4):359-367 (1964).

McCleland, Plastric Reconstructive Surgery, 100(6), Nov. 1997, pp. 1466-1474.

McPherson, John M., "Development and Biochemical Characterization of Injectable Collagen," J. Dermatol Surg Oncol, 14 (Suppl1):Jul. 7, 1988, pp. 13-20.

Millay et al.; "Vasoconstrictors in Facial Plastic Surgery"; Archives of Otolaryngology-Head & Neck Surgery; vol. 117; pp. 160-163; Feb. 1991.

Orvisky, E., et al., "High-molecular-weight hyaluronan—a valuable tool in testing the antioxidative activity of amphiphilic drugs stobadine and vinpocetine," Pharm.Biomed.Anal. 16:419-424 (1997).

Osmitrol (generic name Mannitol),Official FDA Information, side effects and uses, pp. 1-10 (2010) http://www.drugs.com/pro/osmitrol.html.

Park et al., "Biological Characterization of EDC-crosslinked Collagen-Hyaluronic Acid Matrix in Dermal Tissue Restoration", Biomaterials 24 (2003) 1631-1641.

Park et al., "Characterization of Porous Collagen/Hyaluronic Acid Scaffold Modified by 1-ethyl-3-(3-dimethylaminopropyl)carbodiimide cross-linking", Biomaterials 23 (2002): 1205-1212.

Powell; "Stability of Lidocaine in Aqueous Solution: Effect of Temperature, pH, Buffer, and Metal Ions on Amide Hydrolysis"; Pharmaceutical Research; vol. 4, No. 1, 1987.

Prestwich, Glenn D., "Evaluating drug efficacy and toxicology in three dimensions: using synthetic extracellular matrices in drug discovery," Accounts of Chemical Research 41 (1):139-148 (2008).

Rehakova, Milena, et al., "Properties of collagen and hyaluronic acid composite materials and their modifications by chemical crosslinking," Journal of Biomedical Research, vol. 30, 1996, pp. 36-372, XP002590342.

Remington's Pharmaceutical Science Mac Publishing Company, Easton, PA 16th Edition 1980.

Rosenblatt et al., "The Effect of Collagen Fiber Size Distribution on the Release Rate of Proteins from Collagen Matrices by Diffusion", J. Controlled Rel., 9, pp. 195-203 (1989).

Rosenblatt et al., "Chain Rigidity and Diffusional Release in Biopolymer Gels", Proceed. Inter. Symp. Control. Rel. Bioact. Mater., 20, pp. 264-265 (1993) Controlled Release Society, Inc.

Sannino et al., "Crosslinking of Cellulose Derivatives and Hyaluronic Acid with Water-Soluble Carbodiimide," Polymer 46 (2005)pp. 11206-11212.

Sculptra® Aesthetic (injectable poly-L-lactic acid) Directions for Use, Dermik Laboratories product insert (Jul. 2009), sanofi-aventis U.S. LLC.

Segura et al. "Crosslinked hyaluronic acid hydrogels: a strategy to functionalize and pattern." Biomaterials 26(4): 359-371 (2005).

Selvi et al, "Arthritis Induced by Corticosteroid Crystals", J. Rheumatology, 2004, 34:3.

Serban et al. "Modular Extracellular Matrices: Solutions for the Puzzle." Methods 45(1): 93-98 (2008).

Shu et al. "Synthesis and evaluation of injectable, in situ crosslinkable synthetic extracellular matrices for tissue engineering." J. Biomed. Mater. Res. A. 79(4): 902-912 (2006).

(56) References Cited

OTHER PUBLICATIONS

Silver et al., "Physical Properties of Hyaluronic Acid and Hydroxypropylmethylcellulose in Solution: Evaluation of Coating Ability," Journal of Applied Biomaterials, vol. 5, 89-98 (1994).
Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers by; vol. 31, No. 24; pp. 6173-6181; Aug. 1, 2010.
Smith, Kevin C., et al., "Five Percent Lidocaine Cream Applied Simultaneously to Skin and Mucosa of the Lips Creates Excellent Anesthesia for Filler Injections", Dermatol Surg 2005; 31:1635-1637.
Tezel et al. "The science of hyaluronic acid dermal fillers." J. Cosmet. Laser Ther. 10(1): 35-42 (2008).
TRB Chemedica Ophthalmic Line, VISIOL, product info., pp. 1-2.
Visiol, Viscoelstic gel for use in ocular surgery, (2010) p. 1, htt:// www.trbchemedica.com/index.php/option=com_content&tas.
Waraszkiewicz, Sigmund M., et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, Nov. 1981, pp. 1215-1218.
Wahl, "European Evaluation of a New Hyaluronic Acid Filler Incorporating Lidocaine", Journal of Cosmetic Dermatology; vol. 7; pp. 298-303; 2008.
Weidmann; "New Hyaluronic Acid Filler for Subdermal and Long-Lasting vol. Restoration of the Face"; European Dermatology; pp. 65-68; 2009.
Xia, Yun et al., "Comparison of Effects of Lidocaine Hydrochloride, Buffered Lidocaine, Diphenhydramine, and Normal Saline After Intradermal Injection", Journal of Clinical Anesthesia 14:339-343, 2002.
Yeom et al. "Effect of Cross-Linking Reagents for Hyaluronic Acid Hydrogel Dermal Fillers on Tissue Augmentation and Regeneration." Bioconjugate Chem., 21(2): 240-247 (2010).
Yui, Nobuhiko, et al., "Inflammation responsive degradation of crosslinked hyaluronic acid gels," Journal of Controlled release, 22 (1992) pp. 105-116.
Yui, Nobuhiko, et al., "Photo-responsive degradation of heterogeneous hydrogels comprising crosslinked hyaluronic acid and lipid microspheres for temporal drug delivery," Journal of Controlled Release, 26 (1993) pp. 141-145.
Yun, Yh et al. "Hyaluronan Microspheres for Sustained Gene Delivery and Site-Specific Targeting", Biomaterials, vol. 25, 2004, pp. 147-157.
Zheng et al. "In situ crosslinkable hyaluronan hydrogels for tissue engineering." Biomaterials 25(7-8): 1339-1348 (2004).
Zulian et al., Triamcinolone Acetonide and Hexacetonide Intra-Articular Treatment of Symmetrical Joints in Juvenile . Idiopathic Arthritis: a Double-Blind Trial, Rheum 2004.
Boulle et al., "Lip Augmentation and Contour Correction With a Ribose Cross-linked Collagen Dermal Filler", Journals of Drugs in Dermatology, Mar. 2009, vol. 8, Issue 3, pp. 1-8.
Crosslinking Technical Handbook, Thermo Scientific, pp. 1-48, published Apr. 2009.
Park et al., "In vireio evaluation of conjugated Hyalruonic acid with Ascorbic Acid", Journal of Bone & Joint Surgery, British vol. 92-B, XP-002706399, 2010.

* cited by examiner

FLUID COMPOSITIONS FOR IMPROVING SKIN CONDITIONS

This patent application is a continuation of U.S. patent application Ser. No. 12/777,106, filed May 10, 2010, which claims priority pursuant to 35 U.S.C. §119(e) to U.S. Provisional Patent Application Ser. No. 61/313,664 filed Mar. 12, 2010, the entire disclosure of each of these applications being incorporated herein by this reference.

Dermal fillers are useful in soft tissue and dermal correction. One common polymer used in dermal filler compositions is hyaluronan, also known as hyaluronic acid (HA). Although exhibiting excellent biocompatibility and affinity for water molecules, in its natural state, hyaluronan exhibits poor biomechanical properties as a dermal filler. Tezel and Fredrickson, *The Science of Hyaluronic Acid Dermal Fillers*, J Cosmet Laser Ther. 10(1): 35-42 (2008); Kablik, et al., *Comparative Physical Properties of Hyaluronic Acid Dermal Fillers*, Dermatol Surg. 35 Suppl 1: 302-312 (2009); Beasley, et al., *Hyaluronic Acid Fillers: A Comprehensive Review*, Facial Plast Surg. 25(2): 86-94 (2009); each of which is hereby incorporated by reference in its entirety. One primary reason is that this polymer is soluble and is cleared rapidly when administered into a skin region. Tezel, supra, 2008; Kablik, supra, 2009; Beasley, supra, 2009. This in vivo clearance is primarily achieved by degradation, principally enzymatic degradation via hyaluronidase and chemical degradation via free-radicals. To minimize the effect of these in vivo degradation pathways, matrix polymers like hyaluronan are crosslinked to one another to form a hydrogel. Because hydrogels are more solid substance that are readily soluble, dermal fillers comprising such crosslinked matrix polymers remain in place at the implant site. Tezel, supra, 2008; Kablik, supra, 2009; Beasley, supra, 2009. A crosslinked matrix polymer like hyaluronan is also more suitable as a component of a dermal filler because it's more solid nature improves the mechanical properties of the filler, allowing the filler to better lift and fill a skin region. Tezel, supra, 2008; Kablik, supra, 2009; Beasley, supra, 2009.

Hyaluronan is abundant in the different layers of the skin, where it has multiple functions such as to ensure good hydration, assist in the organization of the collagen matrix, and act as a filler material assisting the organization of the extracellular matrix. However, with age, the quantity of hyaluronan present in the skin decreases. This loss of hyaluronan results in various skin conditions such as, e.g., skin dehydration, lack of skin elasticity, skin roughness, lack of skin tautness, skin stretch line and/or marks, skin paleness, skin wrinkles, and the like. As such, it would be desirable to have a skin therapy that can replace the endogenous matrix polymers that are lost with age in order to treat these skin conditions. However, current dermal fillers comprising hydrogels of crosslinked matrix polymers like crosslinked hyaluronan cannot be used to replace the lost endogenous polymers because the crosslinking prevents the ability of these polymers to integrate into the extracellular matrix. However, as discussed above, although uncrosslinked matrix polymers like hyaluronan are soluble, and as such, could integrate into the extracellular matrix and replace lost endogenous hyaluronan, uncrosslinked matrix polymers are rapidly cleared from the body by in vivo degradation pathways. Thus, what is needed is a fluid composition comprising uncrosslinked matrix polymers that include an additional stabilizing component that reduces or prevents matrix polymer degradation.

The fluid compositions disclosed in the present specification achieve this goal. Such fluid compositions comprise a matrix polymer and a stabilizing component that reduces or prevents in vivo degradation of the matrix polymer. Administration of the disclosed fluid compositions improves skin conditions such as, e.g., hydration and the cutaneous elasticity by compensating for the loss of the endogenous polymer.

Thus, aspects of the present specification provide a fluid composition comprising a matrix polymer and a stabilizing component. Matrix polymers useful to make such fluid compositions include, without limitation, a glycosaminoglycan (like chondroitin sulfate, dermatan sulfate, keratan sulfate, hyaluronan) and lubricin. Stabilizing components useful to make such fluid compositions include, without limitation, polyols and flavonoids.

Other aspects of the present specification provide a method of making a fluid composition disclosed in the present specification. In an aspect, a method for making a fluid composition comprises the steps of: a) combining a stabilizing component with a physiologically-acceptable buffer to make a stabilizing component-buffered solution; and b) combining a matrix polymer with the stabilizing component-buffered solution to hydrate the matrix polymer. In another aspect, a method for making a fluid composition comprises the steps of: a) combining a stabilizing component with a physiologically-acceptable buffer to make a stabilizing component-buffered solution; b) combining a matrix polymer with the stabilizing component-buffered solution to hydrate the matrix polymer, and; c) sizing the fluid composition. This method may, or may not, further comprise a step comprising titrating a stabilizing component-buffered solution to obtain a desired pH after step (a); a step comprising filtering the stabilizing component-buffered solution after step (a); a step (b) where combining a matrix polymer with the stabilizing component-buffered solution to hydrate the matrix polymer occurs by mixing the matrix polymer with the stabilizing component-buffered solution at a low speed for a relatively long period of time; a step (b) where combining a matrix polymer with the stabilizing component-buffered solution to hydrate the matrix polymer occurs by mixing the matrix polymer with the stabilizing component-buffered solution at a low speed for a relatively long period of time and then followed by a rest for a relative long period of time; a step (b) where combining a matrix polymer with the stabilizing component-buffered solution to hydrate the matrix polymer occurs by mixing the matrix polymer with the stabilizing component-buffered solution at a low speed for a relatively long period of time and then by mixing the matrix polymer with the stabilizing component-buffered solution using a cycle of alternating periods of agitation for a relatively short period of time followed by periods of rest for a relatively long period of time; a step (b) where combining a matrix polymer with the stabilizing component-buffered solution to hydrate the matrix polymer occurs by mixing the matrix polymer with the stabilizing component-buffered solution at a low speed for a relatively long period of time and then by mixing the matrix polymer with the stabilizing component-buffered solution using a cycle of alternating periods of agitation for a relatively short period of time followed by periods of rest for a relatively long period of time, and then followed by a rest for a relative long period of time; a step comprising degassing a fluid composition after step (b) or step (c); a step comprising filling a syringe with a fluid composition after step (c); and/or a step comprising sterilizing a syringe filled with a fluid composition after step (c).

Yet other aspects of the present specification provide a fluid composition disclosed in the present specification made by a method disclosed in the present specification.

Still other aspects of the present specification provide a method of improving a condition of skin in an individual in need thereof, the method comprising the steps of administering a fluid composition disclosed in the present specification into a dermal region of the individual, wherein the administration improves the condition. Skin conditions treated by the disclosed fluid compositions include, without limitation, skin dehydration, a lack of skin elasticity, skin roughness, a lack of skin tautness, a skin stretch line or mark, skin paleness, and/or skin wrinkles.

BRIEF DESCRIPTION OF THE DRAWINGS

FIG. 1 is a graph showing the results of hyaluronan polymer degradation with and without mannitol.

DETAILED DESCRIPTION

Figure 1A:
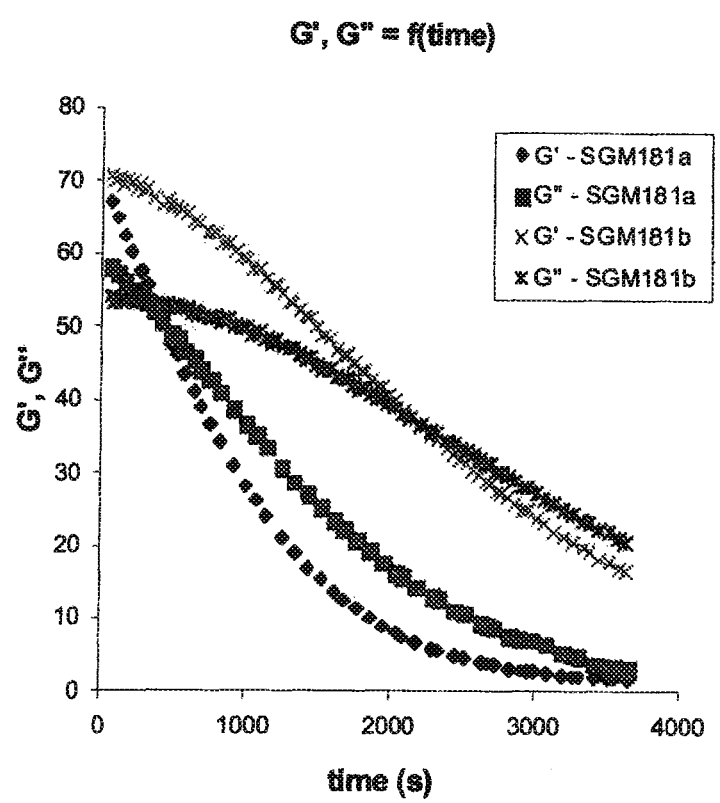
FIG. 1A shows a graph plotting G'G" over time.

Aspects of the present specification provide, in part, a fluid composition comprising a matrix polymer and a stabilizing component. As used herein, the term "fluid" refers to a continuous, amorphous substance whose molecules move freely past one another. A fluid cannot sustain a shearing force when at rest and undergoes a continuous change in shape when subjected to such a force. It should be noted, that although the compositions disclosed in the present specification are fluid in nature due to the presence of uncross linked matrix polymers, such fluid compositions, may, although may not, include cross linked matrix polymers, which, by its nature, is a gel or other solid substance. As such, certain fluid compositions disclosed in the present specification exhibit viscoelastic properties.

Aspects of the present specification provide, in part, a fluid composition comprising a matrix polymer. As used herein, the term "matrix polymer" refers to a polymer that can become part of or function as an extracellular matrix polymer and pharmaceutically acceptable salts thereof. Non-limiting examples of a matrix polymer include a glycosaminoglycan like chondroitin sulfate, dermatan sulfate, keratan sulfate, hyaluronan; lubricants; and collagens. Non-limiting examples of a pharmaceutically acceptable salt of a matrix polymer includes sodium salts, potassium salts, magnesium salts, calcium salts, and combinations thereof.

Aspects of the present specification provide, in part, a fluid composition comprising a glycosaminoglycan. As used herein, the term "glycosaminoglycan" is synonymous with "GAG" and "mucopolysaccharide" and refers to long unbranched polysaccharides consisting of a repeating disaccharide units. The repeating unit consists of a hexose (six-carbon sugar) or a hexuronic acid, linked to a hexosamine (six-carbon sugar containing nitrogen) and pharmaceutically acceptable salts thereof. Members of the GAG family vary in the type of hexosamine, hexose or hexuronic acid unit they contain, such as, e.g., glucuronic acid, iduronic acid, galactose, galactosamine, glucosamine) and may also vary in the geometry of the glycosidic linkage. Any glycosaminoglycan is useful in the compositions disclosed in the present specification with the proviso that the glycosaminoglycan improves a condition of the skin, such as, e.g., hydration or elasticity. Table 1 lists representative GAGs.

TABLE 1

Examples of GAGs

| Name | Hexuronic acid/Hexose | Hexosamine | Glycosidic linkage geometry | Unique features |
|---|---|---|---|---|
| Chondroitin sulfate | GlcUA or GlcUA(2S) | GalNAc or GalNAc(4S) or GalNAc(6S) or GalNAc(4S,6S) | -4GlcUAβ1-3GalNAcβ1- | Most prevalent GAG |
| Dermatan sulfate | GlcUA or IdoUA or IdoUA(2S) | GalNAc or GalNAc(4S) or GalNAc(6S) or GalNAc(4S,6S) | -4IdoUAβ1-3GalNAcβ1- | Distinguished from chondroitin sulfate by the presence of iduronic acid, although some hexuronic acid monosaccharides may be glucuronic acid. |
| Keratan sulfate | Gal or Gal(6S) | GlcNAc or GlcNAc(6S) | -3Gal(6S)β1-4GlcNAc(6S)β1- | Keratan sulfate type II may be fucosylated. |
| Heparin | GlcUA or IdoUA(2S) | GlcNAc or GlcNS or GlcNAc(6S) or GlcNS(6S) | -4IdoUA(2S)α1-4GlcNS(6S)α1- | Highest negative charge density of any known biological molecule |
| Heparan sulfate | GlcUA or IdoUA or IdoUA(2S) | GlcNAc or GlcNS or GlcNAc(6S) or GlcNS(6S) | -4GlcUAβ1-4GlcNAcα1- | Highly similar in structure to heparin, however heparan sulfates disaccharide units are organised into distinct sulfated and non-sulfated domains. |

TABLE 1-continued

Examples of GAGs

| Name | Hexuronic acid/Hexose | Hexosamine | Glycosidic linkage geometry | Unique features |
|---|---|---|---|---|
| Hyaluronan | GlcUA | GlcNAc | -4GlcUAβ1-3GlcNAcβ1- | The only GAG that is exclusively non-sulfated |

GlcUA = β-D-glucuronic acid
GlcUA(2S) = 2-O-sulfo-β-D-glucuronic acid
IdoUA = α-L-iduronic acid
IdoUA(2S) = 2-O-sulfo-α-L-iduronic acid
Gal = β-D-galactose
Gal(6S) = 6-O-sulfo-β-D-galactose
GalNAc = β-D-N-acetylgalactosamine
GalNAc(4S) = β-D-N-acetylgalactosamine-4-O-sulfate
GalNAc(6S) = β-D-N-acetylgalactosamine-6-O-sulfate
GalNAc(4S,6S) = β-D-N-acetylgalactosamine-4-O, 6-O-sulfate
GlcNAc = α-D-N-acetylglucosamine
GlcNS = α-D-N-sulfoglucosamine
GlcNS(6S) = α-D-N-sulfoglucosamine-6-O-sulfate Aspects of the present specification provide, in part, a fluid composition comprising a chondroitin sulfate. As used herein, the term "chondroitin sulfate" refers to an unbranched, sulfated GAG of variable length comprising disaccharides of two alternating monosaccharides of D-glucuronic acid (GlcA) and N-acetyl-D-galactosamine (GalNAc) and pharmaceutically acceptable salts thereof. A chondroitin sulfate may also include D-glucuronic acid residues that are epimerized into L-iduronic acid (IdoA), in which case the resulting disaccharide is referred to as dermatan sulfate. A chondroitin sulfate polymer can have a chain of over 100 individual sugars, each of which can be sulfated in variable positions and quantities. Chondroitin sulfate is an important structural component of cartilage and provides much of its resistance to compression. Any chondroitin sulfate is useful in the compositions disclosed in the present specification with the proviso that the chondroitin sulfate improves a condition of the skin, such as, e.g., hydration or elasticity. Non-limiting examples of pharmaceutically acceptable salts of chondroitin sulfate include sodium chondroitin sulfate, potassium chondroitin sulfate, magnesium chondroitin sulfate, calcium chondroitin sulfate, and combinations thereof.

Aspects of the present specification provide, in part, a fluid composition comprising a keratan sulfate. As used herein, the term "keratan sulfate" refers to a GAG of variable length comprising disaccharide units, which themselves include β-D-galactose and N-acetyl-D-galactosamine (GalNAc) and pharmaceutically acceptable salts thereof. Disaccharides within the repeating region of keratan sulfate may be fucosylated and N-Acetylneuraminic acid caps the end of the chains. Any keratan sulfate is useful in the compositions disclosed in the present specification with the proviso that the keratan sulfate improves a condition of the skin, such as, e.g., hydration or elasticity. Non-limiting examples of pharmaceutically acceptable salts of keratan sulfate include sodium keratan sulfate, potassium keratan sulfate, magnesium keratan sulfate, calcium keratan sulfate, and combinations thereof.

Aspects of the present specification provide, in part, a fluid composition comprising a hyaluronan. As used herein, the term "hyaluronic acid" is synonymous with "HA", "hyaluronic acid", and "hyaluronate" refers to an anionic, non-sulfated glycosaminoglycan polymer comprising disaccharide units, which themselves include D-glucuronic acid and D-N-acetylglucosamine monomers, linked together via alternating β-1,4 and β-1,3 glycosidic bonds and pharmaceutically acceptable salts thereof. Hyaluronan can be purified from animal and non-animal sources. Polymers of hyaluronan can range in size from about 5,000 Da to about 20,000,000 Da. Any hyaluronan is useful in the compositions disclosed in the present specification with the proviso that the hyaluronan improves a condition of the skin, such as, e.g., hydration or elasticity. Non-limiting examples of pharmaceutically acceptable salts of hyaluronan include sodium hyaluronan, potassium hyaluronan, magnesium hyaluronan, calcium hyaluronan, and combinations thereof.

Aspects of the present specification provide, in part, a fluid composition comprising a lubricin. As used herein, the term "lubricin" refers to a large, water soluble glycoprotein encoded by the PRG4 gene and pharmaceutically acceptable salts thereof. It has a molecular weight of 206,000 Da and comprises approximately equal proportions of protein and glycosaminoglycans. The structure of lubricin molecule is that of a partially extended flexible rod and, in solution, occupies a smaller spatial domain than would be expected from structural predictions. This characteristic may aid in the molecule's boundary lubricating ability. Lubricin is present in synovial fluid and on the surface (superficial layer) of articular cartilage and therefore plays an important role in joint lubrication and synovial homeostasis. Any lubricin is useful in the compositions disclosed in the present specification with the proviso that the lubricin improves a condition of the skin, such as, e.g., hydration or elasticity. Non-limiting examples of pharmaceutically acceptable salts of lubricin include sodium lubricin, potassium lubricin, magnesium lubricin, calcium lubricin, and combinations thereof.

Aspects of the present specification provide, in part, a fluid composition comprising a crosslinked matrix polymer. As sued herein, the term "crosslinked" refers to the intermolecular bonds joining the individual polymer molecules, or monomer chains, into a more stable structure like a gel. As such, a crosslinked matrix polymer has at least one intermolecular bond joining at least one individual polymer molecule to another one. Matrix polymers disclosed in the present specification may be crosslinked using dialdehydes and disulfides crosslinking agents including, without limitation, divinyl sulfones, diglycidyl ethers, and bis-epoxides. Non-limiting examples of hyaluronan crosslinking agents include divinyl sulfone (DVS), 1,4-butanediol diglycidyl ether (BDDE), 1,2-bis(2,3-epoxypropoxy)ethylene (EGDGE), 1,2,7,8-diepoxyoctane (DEO), biscarbodiimide (BCD), adipic dihydrazide (ADH), bis(sulfosuccinimidyl)suberate (BS), hexamethylenediamine (NMDA), 1-(2,3-epoxypropyl)-2,3-epoxycyclohexane, or combinations thereof.

Aspects of the present specification provide, in part, a fluid composition comprising a crosslinked matrix polymer having a degree of crosslinking. As used herein, the term "degree of crosslinking" refers to the percentage of matrix polymer monomeric units that are bound to a cross-linking agent, such as, e.g., the disaccharide monomer units of hyaluronan. Thus, a fluid composition that has a crosslinked matrix polymer with a 4% degree of crosslinking means that on average there are four crosslinking molecules for every 100 monomeric units. Every other parameter being equal, the greater the degree of crosslinking, the harder the gel becomes. Non-limiting examples of a degree of crosslinking include about 1% to about 15%.

Aspects of the present specification provide, in part, a fluid composition comprising a uncrosslinked matrix polymer. As used herein, the term "uncrosslinked" refers to a lack of intermolecular bonds joining the individual matrix polymer molecules, or monomer chains. As such, an uncrosslinked matrix polymer is not linked to any other matrix polymer by an intermolecular bond.

Aspects of the present specification provide, in part, a fluid composition comprising a substantially uncrosslinked matrix polymer. As sued herein, the term "substantially uncrosslinked" refers to the presence of uncrosslinked matrix polymers in a fluid composition disclosed in the present specification at a level of at least 90% by weight of the composition, with the remaining at most 10% by weight of the composition being comprised of other components including crosslinked matrix polymers. The matrix polymer included in a fluid composition disclosed in the present specification exhibit a low degree of cross-linking in order to remain water soluble.

Aspects of the present specification provide, in part, a fluid composition that is essentially free of a crosslinked matrix polymer. As used herein, the term "essentially free" (or "consisting essentially of") refers to a fluid composition where only trace amounts of cross-linked matrix polymers can be detected.

Aspects of the present specification provide, in part, a fluid composition that is entirely free of a crosslinked matrix polymer. As used herein, the term "entirely free" refers to a fluid composition that within the detection range of the instrument or process being used, crosslinked matrix polymers cannot be detected or its presence cannot be confirmed.

Aspects of the present specification provide, in part, a fluid composition comprising a ratio of crosslinked matrix polymer and uncrosslinked polymer. This ratio of crosslinked and uncrosslinked matrix polymer is also known as the gel:fluid ratio. Any gel:fluid ratio is useful in making the fluid compositions disclosed in the present specification with the proviso that such ratio produces a fluid composition disclosed in the present specification that improves a skin condition as disclosed in the present specification. Non-limiting examples of gel:fluid ratios include 100:0, 98:2, 90:10, 75:25, 70:30, 60:40, 50:50, 40:60, 30:70, 25:75, 10:90; 2:98, and 0:100.

Aspects of the present specification provide, in part, a fluid composition comprising a matrix polymer having a mean molecular weight. As used herein, the term "molecular weight" refers to the sum of the atomic weights of the atoms in a molecule. For example, that of methane ($CH_4$) is 16.043 g/mol, the atomic weights being carbon=12.011 g/mol, hydrogen=1.008 g/mol.

Thus, in an embodiment, a fluid composition comprises a substantially uncrosslinked matrix polymer. In other aspects of this embodiment, a fluid composition comprises an uncrosslinked matrix polymer where the uncrosslinked matrix polymer represents, e.g., about 90% by weight, about 91% by weight, about 92% by weight, about 93% by weight, about 94% by weight, about 95% by weight, about 96% by weight, about 97% by weight, about 98% by weight, or about 99%, or about 100% by weight, of the total matrix polymer present in the composition. In yet other aspects of this embodiment, a fluid composition comprises an uncrosslinked matrix polymer where the uncrosslinked matrix polymer represents, e.g., at least 90% by weight, at least 91% by weight, at least 92% by weight, at least 93% by weight, at least 94% by weight, at least 95% by weight, at least 96% by weight, at least 97% by weight, at least 98% by weight, or at least 99% by weight, of the total matrix polymer present in the composition. In still other aspects of this embodiment, a fluid composition comprises an uncrosslinked matrix polymer where the uncrosslinked matrix polymer represents, e.g., about 90% to about 100% by weight, about 93% to about 100% by weight, about 95% to about 100% by weight, or about 97% to about 100% by weight, of the total matrix polymer present in the composition.

In another embodiment, a fluid composition comprises a substantially uncrosslinked glycosaminoglycan. In aspects of this embodiment, a fluid composition comprises a substantially uncrosslinked chondroitin sulfate polymer, a substantially uncrosslinked chondroitin sulfate polymer, or a substantially uncrosslinked hyaluronan polymer. In other aspects of this embodiment, a fluid composition comprises an uncrosslinked glycosaminoglycan where the uncrosslinked glycosaminoglycan represents, e.g., about 90% by weight, about 91% by weight, about 92% by weight, about 93% by weight, about 94% by weight, about 95% by weight, about 96% by weight, about 97% by weight, about 98% by weight, or about 99%, or about 100% by weight, of the total glycosaminoglycan present in the composition. In yet other aspects of this embodiment, a fluid composition comprises an uncrosslinked glycosaminoglycan where the uncrosslinked glycosaminoglycan represents, e.g., at least 90% by weight, at least 91% by weight, at least 92% by weight, at least 93% by weight, at least 94% by weight, at least 95% by weight, at least 96% by weight, at least 97% by weight, at least 98% by weight, or at least 99% by weight, of the total glycosaminoglycan present in the composition. In still other aspects of this embodiment, a fluid composition comprises an uncrosslinked glycosaminoglycan where the uncrosslinked glycosaminoglycan represents, e.g., about 90% to about 100% by weight, about 93% to about 100% by weight, about 95% to about 100% by weight, or about 97% to about 100% by weight, of the total glycosaminoglycan present in the composition.

In yet another embodiment, a fluid composition comprises a substantially uncrosslinked lubricin. In aspects of this embodiment, a fluid composition comprises an uncrosslinked lubricin where the uncrosslinked lubricin represents, e.g., about 90% by weight, about 91% by weight, about 92% by weight, about 93% by weight, about 94% by weight, about 95% by weight, about 96% by weight, about 97% by weight, about 98% by weight, or about 99%, or about 100% by weight, of the total lubricin present in the composition. In other aspects of this embodiment, a fluid composition comprises an uncrosslinked lubricin where the uncrosslinked lubricin represents, e.g., at least 90% by weight, at least 91% by weight, at least 92% by weight, at least 93% by weight, at least 94% by weight, at least 95% by weight, at least 96% by weight, at least 97% by weight, at least 98% by weight, or at least 99% by weight, of the total lubricin present in the composition. In yet other aspects of this embodiment, a fluid composition comprises an uncrosslinked lubricin where the uncrosslinked lubricin represents, e.g., about 90% to about 100% by weight, about 93% to about 100% by weight, about 95% to about 100% by weight, or about 97% to about 100% by weight, of the total lubricin present in the composition.

In another embodiment, a fluid composition comprises an uncrosslinked matrix polymer that is entirely free of a crosslinked matrix polymer.

In yet another embodiment, a fluid composition comprises an uncrosslinked glycosaminoglycan that is entirely free of a crosslinked glycosaminoglycan. In an aspect of this embodiment, a fluid composition comprises an uncrosslinked chondroitin sulfate polymer that is entirely free of a crosslinked chondroitin sulfate polymer. In another aspect of this embodiment, a fluid composition comprises an uncrosslinked keratan sulfate polymer that is entirely free of a crosslinked keratan sulfate polymer. In yet another aspect of this embodiment, a fluid composition comprises an uncrosslinked hyaluronan polymer that is entirely free of a crosslinked hyaluronan polymer.

In still another embodiment, a fluid composition comprises an uncrosslinked lubricin that is entirely free of a crosslinked lubricin.

In another embodiment, a fluid composition comprises an uncrosslinked matrix polymer that is essentially free of a crosslinked matrix polymer.

In yet another embodiment, a fluid composition comprises an uncrosslinked glycosaminoglycan that is essentially free of a crosslinked glycosaminoglycan. In an aspect of this embodiment, a fluid composition comprises an uncrosslinked chondroitin sulfate polymer that is essentially free of a crosslinked chondroitin sulfate polymer. In another aspect of this embodiment, a fluid composition comprises an uncrosslinked keratan sulfate polymer that is essentially free of a crosslinked keratan sulfate polymer. In yet another aspect of this embodiment, a fluid composition comprises an uncrosslinked hyaluronan polymer that is essentially free of a crosslinked hyaluronan polymer.

In still another embodiment, a fluid composition comprises an uncrosslinked lubricin that is essentially free of a crosslinked lubricin.

In another embodiment, a fluid composition comprises a crosslinked matrix polymer. In other aspects of this embodiment, a fluid composition comprises a crosslinked matrix polymer where the partially crosslinked matrix polymer represents, e.g., about 1% by weight, about 2% by weight, about 3% by weight, about 4% by weight, about 5% by weight, about 6% by weight, about 7% by weight, about 8% by weight, or about 9%, or about 10% by weight, of the total matrix polymer present in the composition. In yet other aspects of this embodiment, a fluid composition comprises a crosslinked matrix polymer where the partially crosslinked matrix polymer represents, e.g., at most 1% by weight, at most 2% by weight, at most 3% by weight, at most 4% by weight, at most 5% by weight, at most 6% by weight, at most 7% by weight, at most 8% by weight, at most 9% by weight, or at most 10% by weight, of the total matrix polymer present in the composition. In still other aspects of this embodiment, a fluid composition comprises a crosslinked matrix polymer where the partially crosslinked matrix polymer represents, e.g., about 0% to about 10% by weight, about 1% to about 10% by weight, about 3% to about 10% by weight, or about 5% to about 10% by weight, of the total matrix polymer present in the composition.

In other aspects of this embodiment, a fluid composition comprises a crosslinked matrix polymer where the degree of crosslinking is about 1%, about 2%, about 3%, about 4%, about 5%, about 6%, about 7%, about 8%, about 9%, about 10%, about 11%, about 12%, about 13%, about 14%, or about 15%. In yet other aspects of this embodiment, a fluid composition comprises a crosslinked matrix polymer where the degree of crosslinking is at most 1%, at most 2%, at most 3%, at most 4%, at most 5%, at most 6%, at most 7%, at most 8%, at most 9%, at most 10%, at most 11%, at most 12%, at most 13%, at most 14%, or at most 15%. In still other aspects of this embodiment, a fluid composition comprises a crosslinked matrix polymer where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%.

In yet another embodiment, a fluid composition comprises a crosslinked glycosaminoglycan. In aspect of this embodiment, a fluid composition comprises a crosslinked chondroitin sulfate polymer, a crosslinked keratan sulfate polymer, or a crosslinked hyaluronan polymer. In other aspects of this embodiment, a fluid composition comprises a crosslinked glycosaminoglycan where the crosslinked glycosaminoglycan represents, e.g., about 1% by weight, about 2% by weight, about 3% by weight, about 4% by weight, about 5% by weight, about 6% by weight, about 7% by weight, about 8% by weight, or about 9%, or about 10% by weight, of the total glycosaminoglycan present in the composition. In yet other aspects of this embodiment, a fluid composition comprises a crosslinked glycosaminoglycan where the crosslinked glycosaminoglycan represents, e.g., at most 1% by weight, at most 2% by weight, at most 3% by weight, at most 4% by weight, at most 5% by weight, at most 6% by weight, at most 7% by weight, at most 8% by weight, at most 9% by weight, or at most 10% by weight, of the total glycosaminoglycan present in the composition. In still other aspects of this embodiment, a fluid composition comprises a crosslinked glycosaminoglycan where the crosslinked glycosaminoglycan represents, e.g., about 0% to about 10% by weight, about 1% to about 10% by weight, about 3% to about 10% by weight, or about 5% to about 10% by weight, of the total glycosaminoglycan present in the composition.

In other aspects of this embodiment, a fluid composition comprises a crosslinked glycosaminoglycan where the degree of crosslinking is about 1%, about 2%, about 3%, about 4%, about 5%, about 6%, about 7%, about 8%, about 9%, about 10%, about 11%, about 12%, about 13%, about 14%, or about 15%. In yet other aspects of this embodiment, a fluid composition comprises a crosslinked glycosaminoglycan where the degree of crosslinking is at most 1%, at most 2%, at most 3%, at most 4%, at most 5%, at most 6%, at most 7%, at most 8%, at most 9%, at most 10%, at most 11%, at most 12%, at most 13%, at most 14%, or at most 15%. In still other aspects of this embodiment, a fluid composition comprises a crosslinked glycosaminoglycan where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%.

In still another embodiment, a fluid composition comprises a crosslinked lubricin. In aspects of this embodiment, a fluid composition comprises a crosslinked lubricin where the crosslinked lubricin represents, e.g., about 1% by weight, about 2% by weight, about 3% by weight, about 4% by weight, about 5% by weight, about 6% by weight, about 7% by weight, about 8% by weight, or about 9%, or about 10% by weight, of the total lubricin present in the composition. In other aspects of this embodiment, a fluid composition comprises a crosslinked lubricin where the crosslinked lubricin represents, e.g., at most 1% by weight, at most 2% by weight, at most 3% by weight, at most 4% by weight, at most 5% by weight, at most 6% by weight, at most 7% by weight, at most 8% by weight, at most 9% by weight, or at most 10% by weight, of the total lubricin present in the composition. In yet other aspects of this embodiment, a fluid composition comprises a crosslinked lubricin where the crosslinked lubricin represents, e.g., about 0% to about 10% by weight, about 1% to about 10% by weight, about 3% to about 10% by weight, or about 5% to about 10% by weight, of the total lubricin present in the composition.

In other aspects of this embodiment, a fluid composition comprises a crosslinked lubricin where the degree of crosslinking is about 1%, about 2%, about 3%, about 4%, about 5%, about 6%, about 7%, about 8%, about 9%, about 10%, about 11%, about 12%, about 13%, about 14%, or about 15%. In yet other aspects of this embodiment, a fluid composition comprises a crosslinked lubricin where the degree of crosslinking is at most 1%, at most 2%, at most 3%, at most 4%, at most 5%, at most 6%, at most 7%, at most 8%, at most 9%, at most 10%, at most 11%, at most 12%, at most 13%, at most 14%, or at most 15%. In still other aspects of this embodiment, a fluid composition comprises a crosslinked lubricin where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%.

In another embodiment, a fluid composition comprises an uncrosslinked matrix polymer where the uncrosslinked matrix polymer is present in an amount sufficient to improve a condition of the skin, such as, e.g., hydration or elasticity. In aspects of this embodiment, a fluid composition comprises an uncrosslinked matrix polymer where the uncrosslinked matrix polymer is present at a concentration of, e.g., about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 13.5 mg/mL, about 14 mg/mL, about 15 mg/mL, about 16 mg/mL, about 17 mg/mL, about 18 mg/mL, about 19 mg/mL, or about 20 mg/mL. In other aspects of this embodiment, a fluid composition comprises an uncrosslinked matrix polymer where the uncrosslinked matrix polymer is present at a concentration of, e.g., at least 1 mg/mL, at least 5 mg/mL, at least 10 mg/mL, at least 15 mg/mL, at least 20 mg/mL, or at least 25 mg/mL. In yet other aspects of this embodiment, a fluid composition comprises an uncrosslinked matrix polymer where the uncrosslinked matrix polymer is present at a concentration of, e.g., at most 1 mg/mL, at most 5 mg/mL, at most 10 mg/mL, at most 15 mg/mL, at most 20 mg/mL, or at most 25 mg/mL. In still other aspects of this embodiment, a fluid composition comprises an uncrosslinked matrix polymer where the uncrosslinked matrix polymer is present at a concentration of, e.g., about 7.5 mg/mL to about 19.5 mg/mL, about 8.5 mg/mL to about 18.5 mg/mL, about 9.5 mg/mL to about 17.5 mg/mL, about 10.5 mg/mL to about 16.5 mg/mL, about 11.5 mg/mL to about 15.5 mg/mL, or about 12.5 mg/mL to about 14.5 mg/mL.

In yet another embodiment, a fluid composition comprises an uncrosslinked glycosaminoglycan where the uncrosslinked glycosaminoglycan is present in an amount sufficient to improve a condition of the skin, such as, e.g., hydration or elasticity. In aspects of this embodiment, a fluid composition comprises an uncrosslinked glycosaminoglycan where the uncrosslinked glycosaminoglycan is present at a concentration of, e.g., about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 13.5 mg/mL, about 14 mg/mL, about 15 mg/mL, about 16 mg/mL, about 17 mg/mL, about 18 mg/mL, about 19 mg/mL, or about 20 mg/mL. In other aspects of this embodiment, a fluid composition comprises an uncrosslinked glycosaminoglycan where the uncrosslinked glycosaminoglycan is present at a concentration of, e.g., at least 1 mg/mL, at least 2 mg/mL, at least 3 mg/mL, at least 4 mg/mL, at least 5 mg/mL, at least 10 mg/mL, at least 15 mg/mL, at least 20 mg/mL, or at least 25 mg/mL. In yet other aspects of this embodiment, a fluid composition comprises an uncrosslinked glycosaminoglycan where the uncrosslinked glycosaminoglycan is present at a concentration of, e.g., at most 1 mg/mL, at most 2 mg/mL, at most 3 mg/mL, at most 4 mg/mL, at most 5 mg/mL, at most 10 mg/mL, at most 15 mg/mL, at most 20 mg/mL, or at most 25 mg/mL. In still other aspects of this embodiment, a fluid composition comprises an uncrosslinked glycosaminoglycan where the uncrosslinked glycosaminoglycan is present at a concentration of, e.g., about 7.5 mg/mL to about 19.5 mg/mL, about 8.5 mg/mL to about 18.5 mg/mL, about 9.5 mg/mL to about 17.5 mg/mL, about 10.5 mg/mL to about 16.5 mg/mL, about 11.5 mg/mL to about 15.5 mg/mL, or about 12.5 mg/mL to about 14.5 mg/mL.

In still another embodiment, a fluid composition comprises an uncrosslinked lubricin where the uncrosslinked lubricin is present in an amount sufficient to improve a condition of the skin, such as, e.g., hydration or elasticity. In aspects of this embodiment, a fluid composition comprises an uncrosslinked lubricin where the uncrosslinked lubricin is present at a concentration of, e.g., about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 13.5 mg/mL, about 14 mg/mL, about 15 mg/mL, about 16 mg/mL, about 17 mg/mL, about 18 mg/mL, about 19 mg/mL, or about 20 mg/mL. In other aspects of this embodiment, a fluid composition comprises an uncrosslinked lubricin where the uncrosslinked lubricin is present at a concentration of, e.g., at least 1 mg/mL, at least 5 mg/mL, at least 10 mg/mL, at least 15 mg/mL, at least 20 mg/mL, or at least 25 mg/mL. In yet other aspects of this embodiment, a fluid composition comprises an uncrosslinked lubricin where the uncrosslinked lubricin is present at a concentration of, e.g., at most 1 mg/mL, at most 5 mg/mL, at most 10 mg/mL, at most 15 mg/mL, at most 20 mg/mL, or at most 25 mg/mL. In still other aspects of this embodiment, a fluid composition comprises an uncrosslinked lubricin where the uncrosslinked lubricin is present at a concentration of, e.g., about 7.5 mg/mL to about 19.5 mg/mL, about 8.5 mg/mL to about 18.5 mg/mL, about 9.5 mg/mL to about 17.5 mg/mL, about 10.5 mg/mL to about 16.5 mg/mL, about 11.5 mg/mL to about 15.5 mg/mL, or about 12.5 mg/mL to about 14.5 mg/mL.

In a further embodiment, a fluid composition comprises a crosslinked matrix polymer and an uncrosslinked matrix polymer. In another aspect of this embodiment, a fluid composition comprises a crosslinked matrix polymer and an uncrosslinked matrix polymer where the gel:fluid ratio is sufficient to form a fluid. In other aspects of this embodiment, a fluid composition comprises a crosslinked matrix polymer and an uncrosslinked matrix polymer where the gel:fluid ratio is, e.g., about 0:100, about 1:99, about 2:98, about 3:97, about 4:96, about 5:95, about 6:94, about 7:93, about 8:92, about 9:91, or about 10:90. In yet other aspects of this embodiment, a fluid composition comprises a crosslinked matrix polymer and an uncrosslinked matrix polymer where the gel:fluid ratio is, e.g., at most 1:99, at most 2:98, at most 3:97, at most 4:96, at most 5:95, at most 6:94, at most 7:93, at most 8:92, at most 9:91, or at most 10:90. In still other aspects of this embodiment, a fluid composition comprises a crosslinked matrix polymer and an uncrosslinked matrix polymer where the gel:fluid ratio is, e.g., about 0:100 to about 3:97, about 0:100 to about 5:95, or about 0:100 to about 10:90.

In other aspects of this embodiment, a fluid composition comprises a crosslinked matrix polymer and an uncrosslinked matrix polymer where the gel:fluid ratio is, e.g., about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 98:2, or about 100:0. In yet other aspects of this embodiment, a fluid composition comprises a crosslinked matrix polymer and an uncrosslinked matrix polymer where the gel:fluid ratio is, e.g., at most 15:85, at most 20:80, at most 25:75, at most 30:70, at most 35:65, at most 40:60, at most 45:55, at most 50:50, at most 55:45, at most 60:40, at most 65:35, at most 70:30, at most 75:25, at most 80:20, at most 85:15, at most 90:10, at most 95:5, at most 98:2, or at most 100:0. In still other aspects of this embodiment, a fluid composition comprises a crosslinked matrix polymer and an uncrosslinked matrix polymer where the gel:fluid ratio is, e.g., about 10:90 to about 70:30, about 15:85 to about 70:30, about 10:90 to about 55:45, about 80:20 to about 95:5, about 90:10 to about 100:0, about 75:25 to about 100:0, or about 60:40 to about 100:0.

In another embodiment, a fluid composition comprises a substantially uncrosslinked hyaluronan. In aspects of this embodiment, a fluid composition comprises an uncrosslinked hyaluronan where the uncrosslinked hyaluronan represents, e.g., about 90% by weight, about 91% by weight, about 92% by weight, about 93% by weight, about 94% by weight, about 95% by weight, about 96% by weight, about 97% by weight, about 98% by weight, or about 99%, or about 100% by weight, of the total hyaluronan present in the composition. In other aspects of this embodiment, a fluid composition comprises an uncrosslinked hyaluronan where the uncrosslinked hyaluronan represents, e.g., at least 90% by weight, at least 91% by weight, at least 92% by weight, at least 93% by weight, at least 94% by weight, at least 95% by weight, at least 96% by weight, at least 97% by weight, at least 98% by weight, or at least 99% by weight, of the total hyaluronan present in the composition. In yet other aspects of this embodiment, a fluid composition comprises an uncrosslinked hyaluronan where the uncrosslinked hyaluronan represents, e.g., about 90% to about 100% by weight, about 93% to about 100% by weight, about 95% to about 100% by weight, or about 97% to about 100% by weight, of the total hyaluronan present in the composition.

In yet another embodiment, a fluid composition comprises an uncrosslinked hyaluronan where the uncrosslinked hyaluronan is present in an amount sufficient to improve a condition of the skin, such as, e.g., hydration or elasticity. In aspects of this embodiment, a fluid composition comprises an uncrosslinked hyaluronan where the uncrosslinked hyaluronan is present at a concentration of, e.g., about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 13.5 mg/mL, about 14 mg/mL, about 15 mg/mL, about 16 mg/mL, about 17 mg/mL, about 18 mg/mL, about 19 mg/mL, or about 20 mg/mL. In other aspects of this embodiment, a fluid composition comprises an uncrosslinked hyaluronan where the uncrosslinked hyaluronan is present at a concentration of, e.g., at least 1 mg/mL, at least 5 mg/mL, at least 10 mg/mL, at least 15 mg/mL, at least 20 mg/mL, or at least 25 mg/mL. In yet other aspects of this embodiment, a fluid composition comprises an uncrosslinked hyaluronan where the uncrosslinked hyaluronan is present at a concentration of, e.g., at most 1 mg/mL, at most 5 mg/mL, at most 10 mg/mL, at most 15 mg/mL, at most 20 mg/mL, or at most 25 mg/mL. In still other aspects of this embodiment, a fluid composition comprises an uncrosslinked hyaluronan where the uncrosslinked hyaluronan is present at a concentration of, e.g., about 7.5 mg/mL to about 19.5 mg/mL, about 8.5 mg/mL to about 18.5 mg/mL, about 9.5 mg/mL to about 17.5 mg/mL, about 10.5 mg/mL to about 16.5 mg/mL, about 11.5 mg/mL to about 15.5 mg/mL, or about 12.5 mg/mL to about 14.5 mg/mL.

In other aspects of this embodiment, a fluid composition comprises an uncrosslinked hyaluronan where the uncrosslinked hyaluronan has a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other aspects of this embodiment, a fluid composition comprises an uncrosslinked hyaluronan where the uncrosslinked hyaluronan has a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other aspects of this embodiment, a fluid composition comprises an uncrosslinked hyaluronan where the uncrosslinked hyaluronan has a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da. In further aspects, a fluid composition comprises an uncrosslinked hyaluronan where the uncrosslinked hyaluronan has a mean molecular weight of, e.g., greater than 2,000,000 Da and less than about 3,000,000 Da, greater than 2,000,000 Da and less than about 3,500,000 Da, greater than 2,000,000 Da and less than about 4,000,000 Da, greater than 2,000,000 Da and less than about 4,500,000 Da, greater than 2,000,000 Da and less than about 5,000,000 Da.

In another embodiment, a fluid composition comprises an uncrosslinked hyaluronan where the uncrosslinked hyaluronan comprises a combination of both high molecular weight hyaluronan and low molecular weight hyaluronan, in various ratios. As used herein, the term "high molecular weight hyaluronan" refers to a hyaluronan polymer that has a molecular weight of 1,000,000 Da or greater. Non-limiting examples of a high molecular weight hyaluronan include a hyaluronan of about 1,500,000 Da, a hyaluronan of about 2,000,000 Da, a hyaluronan of about 2,500,000 Da, a hyaluronan of about 3,000,000 Da, a hyaluronan of about 3,500,000 Da, a hyaluronan of about 4,000,000 Da, a hyaluronan of about 4,500,000 Da, and a hyaluronan of about 5,000,000 Da. As used herein, the term "low molecular weight hyaluronan" refers to a hyaluronan polymer that has a molecular weight of less than 1,000,000 Da. Non-limiting examples of a low molecular weight hyaluronan include a hyaluronan of about 200,000 Da, a hyaluronan of about 300,000 Da, a hyaluronan of about 400,000 Da, a hyaluronan of about 500,000 Da, a hyaluronan of about 600,000 Da, a hyaluronan of about 700,000 Da, a hyaluronan of about 800,000 Da, and a hyaluronan of about 900,000 Da.

Thus, in an embodiment, a fluid composition comprises an uncrosslinked hyaluronan where the uncrosslinked hyaluronan comprises a combination of both high molecular weight hyaluronan and low molecular weight hyaluronan in a ratio of about 20:1, about 15:1, about 10:1, about 5:1, about 1:1, about 1:5 about 1:10, about 1:15, or about 1:20.

In still another embodiment, a fluid composition comprises a crosslinked hyaluronan. In aspects of this embodiment, a fluid composition comprises a crosslinked hyaluronan where the crosslinked hyaluronan represents, e.g., about 1% by weight, about 2% by weight, about 3% by weight, about 4% by weight, about 5% by weight, about 6% by weight, about 7% by weight, about 8% by weight, or about 9%, or about 10% by weight, of the total hyaluronan present in the composition. In other aspects of this embodiment, a fluid composition comprises a crosslinked hyaluronan where the crosslinked hyaluronan represents, e.g., at most 1% by weight, at most 2% by weight, at most 3% by weight, at most 4% by weight, at most 5% by weight, at most 6% by weight, at most 7% by weight, at most 8% by weight, at most 9% by weight, or at most 10% by weight, of the total hyaluronan present in the composition. In yet other aspects of this embodiment, a fluid composition comprises a crosslinked hyaluronan where the crosslinked hyaluronan represents, e.g., about 0% to about 10% by weight, about 1% to about 10% by weight, about 3% to about 10% by weight, or about 5% to about 10% by weight, of the total hyaluronan present in the composition.

In other aspects of this embodiment, a fluid composition comprises a crosslinked hyaluronan where the degree of crosslinking is about 1%, about 2%, about 3%, about 4%, about 5%, about 6%, about 7%, about 8%, about 9%, about 10%, about 11%, about 12%, about 13%, about 14%, or about 15%. In yet other aspects of this embodiment, a fluid composition comprises a crosslinked hyaluronan where the degree of crosslinking is at most 1%, at most 2%, at most 3%, at most 4%, at most 5%, at most 6%, at most 7%, at most 8%, at most 9%, at most 10%, at most 11%, at most 12%, at most 13%, at most 14%, or at most 15%. In still other aspects of this embodiment, a fluid composition comprises a crosslinked hyaluronan where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%.

In other aspects of this embodiment, a fluid composition comprises a crosslinked hyaluronan where the crosslinked hyaluronan has a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other aspects of this embodiment, a fluid composition comprises a crosslinked hyaluronan where the crosslinked hyaluronan has a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other aspects of this embodiment, a fluid composition comprises a crosslinked hyaluronan where the crosslinked hyaluronan has a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da.

In a further embodiment, a fluid composition comprises a crosslinked hyaluronan and an uncrosslinked hyaluronan. In an aspect of this embodiment, a fluid composition comprises a crosslinked hyaluronan and an uncrosslinked hyaluronan where the gel:fluid ratio is sufficient to form a fluid. In other aspects of this embodiment, a fluid composition comprises a crosslinked hyaluronan and an uncrosslinked hyaluronan where the gel:fluid ratio is, e.g., about 0:100, about 1:99, about 2:98, about 3:97, about 4:96, about 5:95, about 6:94, about 7:93, about 8:92, about 9:91, or about 10:90. In yet other aspects of this embodiment, a fluid composition comprises a crosslinked hyaluronan and an uncrosslinked hyaluronan where the gel:fluid ratio is, e.g., at most 1:99, at most 2:98, at most 3:97, at most 4:96, at most 5:95, at most 6:94, at most 7:93, at most 8:92, at most 9:91, or at most 10:90. In still other aspects of this embodiment, a fluid composition comprises a crosslinked hyaluronan and an uncrosslinked hyaluronan where the gel:fluid ratio is, e.g., about 0:100 to about 3:97, about 0:100 to about 5:95, or about 0:100 to about 10:90.

In other aspects of this embodiment, a fluid composition comprises a crosslinked hyaluronan and an uncrosslinked hyaluronan where the gel:fluid ratio is, e.g., about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 98:2, or about 100:0. In yet other aspects of this embodiment, a fluid composition comprises a crosslinked hyaluronan and an uncrosslinked hyaluronan where the gel:fluid ratio is, e.g., at most 15:85, at most 20:80, at most 25:75, at most 30:70, at most 35:65, at most 40:60, at most 45:55, at most 50:50, at most 55:45, at most 60:40, at most 65:35, at most 70:30, at most 75:25, at most 80:20, at most 85:15, at most 90:10, at most 95:5, at most 98:2, or at most 100:0. In still other aspects of this embodiment, a fluid composition comprises a crosslinked hyaluronan and an uncrosslinked hyaluronan where the gel:fluid ratio is, e.g., about 10:90 to about 70:30, about 15:85 to about 70:30, about 10:90 to about 55:45, about 80:20 to about 95:5, about 90:10 to about 100:0, about 75:25 to about 100:0, or about 60:40 to about 100:0.

Aspects of the present specification provide, in part, a fluid composition comprising a stabilizing component. As used herein, the term "stabilizing component" refers to a molecule that reduces or prevents the degradation of a matrix polymer disclosed in the present specification. The stabilizing component can reduce or prevent enzymatic degradation and/or reduce or prevent chemical degradation. Non-limiting examples of stabilizing components include a polyol and a flavonoid.

Aspects of the present specification provide, in part, a fluid composition comprising a polyol. As used herein, the term "polyol" is synonymous with "sugar alcohol," "polyhydric alcohol," and "polyalcohol" and refers to a hydrogenated form of carbohydrate, whose carbonyl group (aldehyde or ketone, reducing sugar) has been reduced to a primary or secondary hydroxyl group (hence the alcohol), such as, e.g., mannitol from mannose, xylitol from xylose, and lactitol from lactulose. Polyols have the general formula $H(HCHO)_n+1H$. Both monosaccharides and disaccharides can form polyols; however, polyols derived from disaccharides are not entirely hydrogenated because only one aldehyde group is available for reduction. A fluid composition disclosed in the present specification may comprise a single polyol, or a plurality of polyols.

A fluid composition disclosed in the present specification comprises a polyol that is pharmaceutically acceptable. As used herein, the term "pharmaceutically acceptable" means any molecular entity or composition that does not produce an adverse, allergic or other untoward or unwanted reaction when administered to a mammal. It is known in the art that the two-carbon polyol, glycol, is not pharmaceutically acceptable because this polyol is toxic to mammals. It is also known in the art that polyols comprising three or more carbon atoms are typically pharmaceutically acceptable. As such, polyols comprising three or more carbon atoms are generally useful in making the compositions disclosed in the present specification.

leads to the formation of the hydroxyl radical (OH.). A free radical formed in this way can give rise to a series of reactions leading to the formation of different species of active oxygen. Table 2 describes the principal active species of oxygen.

TABLE 2

Principal species of active oxygen

| Name | Chemical Symbol | Comments |
|---|---|---|
| Superoxide anion | $O_2^-$ | Superoxide anions are formed by reduction of molecular oxygen. They are minimally reactive in aqueous media, which enables them to migrate quite a long way from their site of production. Superoxide anions have a weak oxidative action but are capable of generating more reactive radicals. |
| Hydrogen peroxide | $H_2O_2$ | Hydrogen peroxides are formed either by bivalent reduction of molecular oxygen, or by dismutation of the superoxide anion. The absence of electric charges on their surface makes them very lipophilic and minimally reactive in aqueous media. The degradation of hydrogen peroxides (Fenton's reaction) produces very reactive radicals called hydroxyl radicals. |
| Hydroxyl radical | OH• | Hydroxyl radicals are formed by degradation of hydrogen peroxide in the presence of transition metals in their reduced form (Fenton's reaction). Hydroxyl radicals are very reactive. Their half-life is on the order of $10^{-9}$ s. |
| Peroxyl radical | ROO• | Peroxyl radicals are formed by addition of molecular oxygen to free carbon radicals. They are minimally reactive. |
| Organic hydroperoxide | ROOH | Organic hydroperoxides are the protonated form of peroxyl radicals. They are very reactive and decompose anew into peroxyl radicals and alcoxyl radicals. |
| Alcoxyl radical | RO• | Alcoxyl radicals are formed during the degradation of organic peroxides. They are very reactive. Their half-life is on the order of $10^{-6}$ s. |
| Nitric oxide | NO• | Nitric oxides are synthesized from arginine (an amino acid) via the action of nitric oxide synthetase. They interact with hydroxyl radicals to form peroxynitrites. Nitric oxide is a neuromediator and can also be used by immune cells to destroy microbes or dangerous cells. |
| Peroxynitrite | $ONOO^-$ | Peroxynitrites are capable of oxidizing certain substances such as methionine (an amino acid serving as a constituent of proteins and enzymes) or of reacting with SOD (Cf. § 1.3.2.a) thereby "nitrating" tyrosine (another very important amino acid) |
| Nitrosyl radical | ONOOH | Degradation of nitrosyl radicals leads to the formation of hydroxyl radicals. |

Oxidizing power : OH• > RO• > ROO• > NO•

A fluid composition disclosed in the present specification comprises a polyol in an amount sufficient to protect uncrosslinked glycosaminoglycans, like hyaluronan, from degradation, such as enzymatic degradation and chemical degradation. One primary means of such glycosaminoglycan degradation is chemical breakdown from exposure to free radicals, such as, e.g., OH. radicals. Free radicals are atoms, molecules, or ions with unpaired electrons on an open shell configuration. The unpaired electrons cause them to be highly chemically reactive.

Free radicals play an important role in a number of biological processes, some of which are necessary for life, such as the intracellular killing of bacteria by phagocytic cells such as granulocytes and macrophages. Free radicals have also been implicated in certain cell signaling processes, called redox signaling. The two most important oxygen-centered free radicals are superoxide and hydroxyl radical. They are derived from molecular oxygen under reducing conditions. For example, the superoxide anion ($O_2^-$) can capture another electron to form the peroxide ion ($O_2^{2-}$), which in turn may react with two $H^+$ protons to form hydrogen peroxide ($H_2O_2$). The degradation of hydrogen peroxide in the presence of transition metals in their reduced form (Fenton's reaction)

However, because of their reactivity, these same free radicals can participate in unwanted side reactions resulting in cell damage. For purposes of the present specification, OH. radicals interact with the hydrogen located on the carbon adjacent to the carboxyl group in the glucuronic ring of hyaluronan and other glycosaminoglycans, thereby removing it. This removal causes splitting of the glycoside bond and hence depolymerization of the polymer.

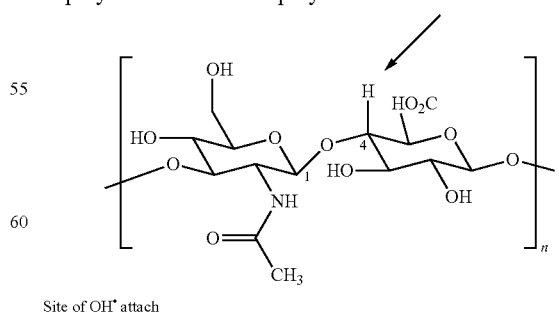

Site of OH• attach

In general, the crosslinking observed in the hyaluronan and other matrix polymers used in dermal fillers protect these polymers against the chemical breakdown of free radical species of oxygen. This is because the bonds formed during crosslinking mask the hydrogen attached by the free radicals. However, the uncrosslinked glycosaminoglycans disclosed in the present specification is afforded no such protection. The present specification discloses an alternative means of protecting matrix polymers from oxidative degradation of free radicals. It has been determined that polyols disclosed in the present specification act as stabilizing agents that can neutralize free radicals of active oxygen. As a stabilizing, a polyol is stabilizing component that protects matrix polymers like hyaluronan against the effects of oxidative stress and limiting the degradation of the fluid compositions disclosed in the present specification.

Thus, any polyol is useful in making the compositions disclosed in the present specification, with the proviso that the polyol is non-toxic to a mammal and the polyol protects uncrosslinked matrix polymers like hyaluronan from degradation. Non-limiting examples of polyols include, glycerol, erythritol, threitol, arabitol, erythritol, ribitol, xylitol, galactitol (or dulcitol), glucitol (or sorbitol), iditol, inositol, mannitol, isomalt, lactitol, maltitol, and polyglycitol. Other non-limiting examples of polyols can be found in, e.g., Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

Thus in an embodiment, a fluid composition comprises a pharmaceutically acceptable polyol that can reduce or prevent degradation of a matrix polymer. In aspects of this embodiment, a fluid composition comprises a pharmaceutically acceptable three-carbon polyol, a pharmaceutically acceptable four-carbon polyol, a pharmaceutically acceptable five-carbon polyol, a pharmaceutically acceptable six-carbon polyol, a pharmaceutically acceptable seven-carbon polyol, a pharmaceutically acceptable eight-carbon polyol, a pharmaceutically acceptable nine-carbon polyol, a pharmaceutically acceptable ten-carbon polyol, a pharmaceutically acceptable eleven-carbon polyol, or a pharmaceutically acceptable twelve-carbon polyol. In other aspects of this embodiment, a fluid composition comprises glycerol, erythritol, threitol, arabitol, erythritol, ribitol, xylitol, galactitol (or dulcitol), glucitol (or sorbitol), iditol, inositol, mannitol, isomalt, lactitol, maltitol, or polyglycitol.

In another embodiment, a fluid composition comprises a single polyol that can reduce or prevent degradation of a matrix polymer. In yet another embodiment, a fluid composition comprises a plurality of polyols, each of which can reduce or prevent the degradation of a matrix polymer. In aspects of this embodiment, a fluid composition comprises one or more polyols, two or more polyols, three or more polyols, four or more polyols, or five or more polyols. In other aspects of this embodiment, a fluid composition comprises one to five polyols, two to five polyols, three to five polyols, two to four polyols, two to five polyols, or three to five polyols.

In yet another embodiment, a fluid composition comprises a polyol in an amount sufficient to reduce or prevent degradation of a matrix polymer. In aspects of this embodiment, a fluid composition comprises a polyol in an amount of, e.g., about 0.1% (w/v) of the composition, about 0.2% (w/v) of the composition, about 0.3% (w/v) of the composition, about 0.4% (w/v) of the composition, about 0.5% (w/v) of the composition, about 0.6% (w/v) of the composition, about 0.7% (w/v) of the composition, about 0.8% (w/v) of the composition, about 0.9% (w/v) of the composition, about 1.0% (w/v) of the composition, about 2.0% (w/v) of the composition, about 3.0% (w/v) of the composition, about 4.0% (w/v) of the composition, about 5.0% (w/v) of the composition, about 6.0% (w/v) of the composition, about 7.0% (w/v) of the composition, about 8.0% (w/v) of the composition, about 9.0% (w/v) of the composition, or about 10% (w/v) of the composition. In other aspects, a fluid composition comprises a polyol in an amount of, e.g., at least 0.1% (w/v) of the composition, at least 0.2% (w/v) of the composition, at least 0.3% (w/v) of the composition, at least 0.4% (w/v) of the composition, at least 0.5% (w/v) of the composition, at least 0.6% (w/v) of the composition, at least 0.7% (w/v) of the composition, at least 0.8% (w/v) of the composition, at least 0.9% (w/v) of the composition, at least 1.0% (w/v) of the composition, at least 2.0% (w/v) of the composition, at least 3.0% (w/v) of the composition, at least 4.0% (w/v) of the composition, at least 5.0% (w/v) of the composition, at least 6.0% (w/v) of the composition, at least 7.0% (w/v) of the composition, at least 8.0% (w/v) of the composition, at least 9.0% (w/v) of the composition, or at least 10% (w/v) of the composition. In yet other aspects, a fluid composition comprises a polyol in an amount of, e.g., at most 0.1% (w/v) of the composition, at most 0.2% (w/v) of the composition, at most 0.3% (w/v) of the composition, at most 0.4% (w/v) of the composition, at most 0.5% (w/v) of the composition, at most 0.6% (w/v) of the composition, at most 0.7% (w/v) of the composition, at most 0.8% (w/v) of the composition, at most 0.9% (w/v) of the composition, at most 1.0% (w/v) of the composition, at most 2.0% (w/v) of the composition, at most 3.0% (w/v) of the composition, at most 4.0% (w/v) of the composition, at most 5.0% (w/v) of the composition, at most 6.0% (w/v) of the composition, at most 7.0% (w/v) of the composition, at most 8.0% (w/v) of the composition, at most 9.0% (w/v) of the composition, or at most 10% (w/v) of the composition. In still other aspects, a fluid composition comprises a polyol in an amount of, e.g., about 0.1% (w/v) to about 1.0% (w/v) of the composition, about 0.1% (w/v) to about 2.0% (w/v) of the composition, about 0.1% (w/v) to about 3.0% (w/v) of the composition, about 0.1% (w/v) to about 4.0% (w/v) of the composition, about 0.1% (w/v) to about 5.0% (w/v) of the composition, about 0.2% (w/v) to about 0.9% (w/v) of the composition, about 0.2% (w/v) to about 1.0% (w/v) of the composition, about 0.2% (w/v) to about 2.0% (w/v) of the composition, about 0.5% (w/v) to about 1.0% (w/v) of the composition, or about 0.5% (w/v) to about 2.0% (w/v) of the composition.

In other aspects of this embodiment, a fluid composition comprises a polyol is present at a concentration of, e.g., about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 2.0 mg/mL, about 3.0 mg/mL, about 4.0 mg/mL, about 5.0 mg/mL, about 6.0 mg/mL, about 7.0 mg/mL, about 8.0 mg/mL, about 9.0 mg/mL, or about 10 mg/mL. In yet other aspects of this embodiment, a fluid composition comprises a polyol present at a concentration of, e.g., at least 0.01 mg/mL, at least 0.02 mg/mL, at least 0.03 mg/mL, at least 0.04 mg/mL, at least 0.05 mg/mL, at least 0.06 mg/mL, at least 0.07 mg/mL, at least 0.08 mg/mL, at least 0.09 mg/mL, at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1.0 mg/mL, at least 2.0 mg/mL, at least 3.0 mg/mL, at least 4.0 mg/mL, at least 5.0 mg/mL, at least 6.0 mg/mL, at least 7.0 mg/mL, at least 8.0 mg/mL, at least 9.0 mg/mL, or at least 10 mg/mL. In still other aspects of this embodiment, a fluid composition comprises a polyol present at a concentration of, e.g., at most 0.01 mg/mL, at most 0.02 mg/mL, at most 0.03 mg/mL, at most 0.04 mg/mL, at most 0.05 mg/mL, at most 0.06 mg/mL, at most 0.07 mg/mL, at most 0.08 mg/mL, at most 0.09 mg/mL, at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1.0 mg/mL, at most 2.0 mg/mL, at most 3.0 mg/mL, at most 4.0 mg/mL, at most 5.0 mg/mL, at most 6.0 mg/mL, at most 7.0 mg/mL, at most 8.0 mg/mL, at most 9.0 mg/mL, or at most 10 mg/mL. In further aspects, a fluid composition comprises a polyol present at a concentration of, e.g., about 0.01 mg/mL to about 0.7 mg/mL, about 0.06 mg/mL to about 0.7 mg/mL, about 0.01 mg/mL to about 1.0 mg/mL, about 0.05 mg/mL to about 1.0 mg/mL, about 0.06 mg/mL to about 1.0 mg/mL, about 0.1 mg/mL to about 1.0 mg/mL, about 0.1 mg/mL to about 2.0 mg/mL, about 0.1 mg/mL to about 3.0 mg/mL, about 0.1 mg/mL to about 4.0 mg/mL, about 0.1 mg/mL to about 5.0 mg/mL, about 0.2 mg/mL to about 0.9 mg/mL, about 0.2 mg/mL to about 1.0 mg/mL, about 0.2 mg/mL to about 2.0 mg/mL, about 0.5 mg/mL to about 1.0 mg/mL, or about 0.5 mg/mL to about 2.0 mg/mL.

Aspects of the present specification provide, in part, a fluid composition that can optionally comprise or not comprise a flavonoid (Table 3). A flavonoid (or bioflavonoid) refers to the class of polyphenolic ketone-containing and non-ketone-containing secondary metabolites found in plants that are well known to have diverse beneficial biochemical and antioxidant effects. Non-limiting examples of flavonoids include C-methylated flavonoids, O-methylated flavonoids, isoflavonoids, neoflavonoids, flavonolignans, furanoflavonoids, pyranoflavonoids, methylenedioxyflavonoids, prenylated flavonoids, aurones, flavones, flavonols, flavanones, flavanonols, flavan-3-ols, flavan-4-ols, leucoanthocyanidin (flavan-3,4-diols), anthocyanidins, and tannins. It is understood that these and other substances known in the art of pharmacology can be included in a fluid composition disclosed in the present specification. See for example, Remington's *Pharmaceutical Sciences* Mac Publishing Company, Easton, Pa. 16$^{th}$ Edition 1980.

Aurones are compounds derived from 2-benzylidene-1-benzofuran-3-one. Non-limiting examples of aurones include 4,5,6-trihydroxy-aurone, aureusidin, hispidol, leptosidin, maritimetin, and sulfuretin.

Three major classes of ketone-containing flavonoids are flavones, compounds derived from 2-phenylchromen-4-one (2-phenyl-1,4-benzopyrone); isoflavones, compounds derived from 3-phenylchromen-4-one (3-phenyl-1,4-benzopyrone); and neoflavones, compounds derived from 4-phenylcoumarin (4-phenyl-1,2-benzopyrone) (Table 3). Flavones are themselves divided into four groups based on the presence or absence of 3-hydroxyl 2,3-dihydro functional groups: flavones, compounds derived from 2-phenylchromen-4-one lack both functional groups; flavonols (3-hydroxyflavone), compounds derived from 3-hydroxy-2-phenylchromen-4-one have the 3-hydroxyl group, but lack the 2,3-dihydro group; flavanones, compounds derived from 2,3-dihydro-2-phenylchromen-4-one have the 2,3-dihydro group, but lack the 3-hydroxyl group; and flavanonols (3-hydroxyflavanone or 2,3-dihydroflavonol), compounds derived from 3-hydroxy-2,3-dihydro-2-phenylchromen-4-one have both functional groups.

Non-limiting examples of flavones include acacetin, apiin, apigenin, apigetrin, artoindonesianin P, baicalein, baicalin, chrysin, cynaroside, diosmetin, diosmin, eupatilin, flavoxate, 6-hydroxyflavone, genkwanin, hidrosmin, luteolin, nepetin, nepitrin (nepetin 7-glucoside), nobiletin, orientin (isoorientin), oroxindin, oroxylin A, rhoifolin, scutellarein, scutellarin, tangeritin, techtochrysin, tetuin, tricin, veronicastroside, vitexin (isovitexin), and wogonin. Non-limiting examples of flavonols include 3-hydroxyflavone, azaleatin, fisetin, galangin, gossypetin, kaempferide, kaempferol, isorhamnetin, morin, myricetin, natsudaidain, pachypodol, quercetin, rhamnazin, rhamnetin, and sophorin. Non-limiting examples of flavanones include butin, eriodictyol, hesperetin, hesperidin, homoeriodictyol, isosakuranetin, naringenin, naringin, pinocembrin, poncirin, sakuranetin, sakuranin, and sterubin. Non-limiting examples of flavanonols include taxifolin (dihydroquercetin), and aromadedrin (dihydrokaempferol).

Isoflavonoids include isoflavones and isoflavanes (Table 3). Non-limiting examples of isoflavonoids include alpinumisoflavone, anagyroidisoflavone A and B, calycosin, daidzein, daidzin, derrubone, di-O-methylalpinumisoflavone, formononetin, genistein, genistin, glycitein, ipriflavone, irigenin, iridin, irilone, 4'-methylalpinumisoflavone, 5-O-methylgenistein, luteone, ononin, orobol, pratensein, prunetin, pseudobaptigenin, psi-tectorigenin, puerarin, retusin, tectoridin, tectorigenin, and wighteone.

Neoflavonoids include 4-arylcoumarins (neoflavones), 4-arylchromanes, dalbergiones and dalbergiquinols (Table 3). Neoflavones are compounds derived from 4-phenylcoumarin (or 4-Aryl-coumarin); neoflavenes compounds derived from 4-phenylchromen. Non-limiting examples of neoflavonoids include calophyllolide, coutareagenin, dalbergichromene, dalbergin, and nivetin.

Non-ketone-containing flavonoids, include flavan-3-ols and catechins. Flavan-3-ols (flavanols) are a class of flavonoids derived from 2-phenyl-3,4-dihydro-2H-chromen-3-ol skeleton. Catechin possesses two benzene rings (called the A- and B-rings) and a dihydropyran heterocycle (the C-ring) with an hydroxyl group on carbon 3. The A ring is similar to a resorcinol moiety while the B ring is similar to a catechol moiety. There are two chiral centers on the molecule on carbons 2 and 3. It has therefore four diastereoisomers. Two of the isomers are in trans configuration and are called catechin and the other two are in cis configuration and are called epicatechin. Non-limiting examples of non-ketone-containing flavonoids include afzelechin, arthromerin A, arthromerin B, catechin, epicatechin, epigallocatechin, epicatechin gallate, epigallocatechin gallate, epigallocatechin gallate, epiafzelechin, fisetinidol, gallocatechin, gallocatechin gallate, guibourtinidol, meciadanol (3-O-methylcatechin), mesquitol, robinetinidol, and thearubigin.

Flavan-4-ols (3-deoxyflavonoids) are flavone-derived alcohols derived from 2-phenylchroman-4-ol. Non-limiting examples of flavan-4-ols include apiforol and luteoforol.

Leucoanthocyanidin (flavan-3,4-diols) are compounds derived from 2-phenyl-3,4-dihydro-2H-chromene-3,4-diol. Non-limiting examples of flavan-3,4-diols include leucocyanidin, leucodelphinidin, leucomalvidin, leucopelargonidin, leucopeonidin, leucorobinetinidin, and melacacidin.

Anthocyanidins are compounds derived from 2-phenylchromenylium. Non-limiting examples of anthocyanidins include antirrhinin, apigeninidin, aurantinidin, capensinidin, chrysanthenin, columnidin, commelinin, cyanidin, 6-hydroxycyanidin, cyanidin-3-(di-p-coumarylglucoside)-5-glucoside, cyanosalvianin, delphinidin, diosmetinidin, europinidin, fisetinidin, gesneridin, guibourtinidin, hirsutidin, luteolinidin, malvidin, 5-desoxy-malvidin, malvin, myrtillin, oenin, peonidin, 5-desoxy-peonidin, pelargonidin, petunidin, primulin, protocyanin, protodelphin, pulchellidin, pulchellidin 3-glucoside, pulchellidin 3-rhamnoside, robinetinidin, rosinidin, tricetinidin, tulipanin, and violdelphin.

Tannins are compounds derived from 2-phenylchromenylium. There are three major classes of tannins: hydrolyzable tannins; non-hydrolyzable tannins (condensed tannins; proanthocyanidins); and pseudotannins.

Hydrolyzable tannins are themselves divided into four groups: oligomer tannins including aglycone tannins and glycoside tannins; ellagitannins; gallotannins, and unclassified tannins. Non-limiting examples of aglycone tannins include ellagic acid, gallagic acid, and gallic acid. Non-limiting examples of glycoside tannins include glucose, quinic acid, and shikimic acid. Non-limiting examples of ellagitannins include castalagin (vescalagin), castalin, casuarictin, casuariin, casuarinin, cornusiin E, grandinin, pedunculagin, punicacortein C, punigluconin, punicalagin, punicalagin alpha, punicalin, 2-O-galloyl-punicalin, stachyurin, strictinin, and tellimagrandin II. Non-limiting examples of gallotannins include corilagin, galloyl glucose, digalloyl glucose, trigalloyl glucose, tetragalloyl glucose, pentagalloyl glucose, hexagalloyl glucose, heptagalloyl glucose, octagalloyl glucose, and tannic acid. Non-limiting examples of unclassified tannins include acutissimin A, acutissimin B, chebulagic acid, chebulinic acid, cinnamtannin B1, combreglutinin, geraniin, granatin B, roburin A, roburin B, roburin C, roburin D, roburin E, stachyurin, tercatin, terflavins A, terflavins B, tergallagin, vescalin, 1,3,4-tri-O-galloylquinic acid, 3,5-di-O-galloyl-shikimic acid, and 3,4,5-tri-O-galloylshikimic acid.

Condensed tannins (proanthocyanidins) are essentially polymer chains of flavonoids such as catechins. Non-limiting examples of condensed tannins include proanthocyanidin, prodelphinidin, profisetinidin, proguibourtinidin, and prorobinetidin.

TABLE 3

| Flavonoids | | |
|---|---|---|
| Flavonoids | Base compound | Examples |
| Aurones | 2-benzylidene-1-benzofuran-3-one | 4,5,6-trihydroxy-aurone, aureusidin, hispidol, leptosidin, maritimetin, and sulfuretin |
| Flavones | 2-phenylchromen-4-one | acacetin, apiin, apigenin, apigetrin, artoindonesianin P, baicalein, baicalin, chrysin, cynaroside, diosmetin, diosmin, eupatilin, flavoxate, 6-hydroxyflavone, genkwanin, hidrosmin, luteolin, nepetin, nepitrin, nobiletin, orientin, oroxindin, oroxylin A, rhoifolin, scutellarein, scutellarin, tangeritin, techtochrysin, tetuin, tricin, veronicastroside, vitexin, wogonin |
| Flavonols | 3-hydroxy-2-phenylchromen-4-one | 3-hydroxyflavone, azaleatin, fisetin, galangin, gossypetin, kaempferide, kaempferol, isorhamnetin, morin, myricetin, natsudaidain, pachypodol, quercetin, rhamnazin, rhamnetin, sophorin |
| Flavanones | 2,3-dihydro-2-phenylchromen-4-one | butin, eriodictyol, hesperetin, hesperidin, homoeriodictyol, isosakuranetin, naringenin, naringin, pinocembrin, poncirin, sakuranetin, sakuranin, sterubin |
| Flavanonols | 3-hydroxy-2,3-dihydro-2-phenylchromen-4-one | aromadedrin, taxifolin |
| Isoflavones | 3-phenylchromen-4-one | alpinumisoflavone, anagyroidisoflavone A and B, calycosin, daidzein, daidzin, derrubone, di-O-methylalpinumisoflavone, formononetin, genistein, genistin, glycitein, ipriflavone, irigenin, iridin, irilone, 4'-methyl-alpinumisoflavone, 5-O-methylgenistein, luteone, ononin, orobol, pratensein, prunetin, pseudobaptigenin, psi-tectorigenin, puerarin, retusin, tectoridin, tectorigenin, wighteone |
| Isoflavenes | 3-phenylchroman | lonchocarpane, laxiflorane |
| Neoflavones | 4-phenylcoumarine | calophyllolide |
| Neoflavenes | 4-phenylchromene | dalbergichromene |
| Flavan-3-ols | 2-phenyl-3,4-dihydro-2H-chromen-3-ol | arthromerin A, arthromerin B, fisetinidol, guibourtinidol, meciadanol (3-O-methylcatechin), mesquitol, robinetinidol, thearubigin. |

TABLE 3-continued

Flavonoids

| Flavonoids | Base compound | Examples |
| --- | --- | --- |
| Catechins | (2R,3S)-2-(3,4-dihydroxyphenyl)-3,4-dihydro-2H-chromene-3,5,7-triol | (+)-catechin (2R-3S), (−)-catechin (2S-3R), (−)-Epicatechin (2R-3R), (+)-epicatechin (2S-3S) |
| Flavan-4-ols | 2-phenylchroman-4-ol | apiforol, luteoforol |
| Flavan-3,4-diols | 2-phenyl-3,4-dihydro-2H-chromene-3,4-diol | leucocyanidin, leucodelphinidin, leucomalvidin, leucopelargonidin, leucopeonidin, leucorobinetinidin, melacacidin |
| Anthocyanidins | 2-phenylchromenylium | antirrhinin, apigeninidin, aurantinidin, capensinidin, chrysanthenin, columnidin, commelinin, cyanidin, 6-hydroxycyanidin, cyanidin-3-(di-p-coumarylglucoside)-5-glucoside, cyanosalvianin, delphinidin, diosmetinidin, europinidin, fisetinidin, gesneridin, guibourtinidin, hirsutidin, luteolinidin, malvidin, 5-desoxy-malvidin, malvin, myrtillin, oenin, peonidin, 5-desoxy-peonidin, pelargonidin, petunidin, primulin, protocyanin, protodelphin, pulchellidin, pulchellidin 3-glucoside, pulchellidin 3-rhamnoside, robinetinidin, rosinidin, tricetinidin, tulipanin, violdelphin |
| Hydrolyzable tannins | gallic acid or ellagic acid | castalagin, castalin, casuarictin, casuariin, casuarinin, corilagin, cornusiin E, grandinin, galloyl glucose, digalloyl glucose, trigalloyl glucose, tetragalloyl glucose, pentagalloyl glucose, hexagalloyl glucose, heptagalloyl glucose, octagalloyl glucose, pedunculagin, punicacortein C, punigluconin, punicalagin, punicalagin alpha, punicalin, 2-O-galloyl-punicalin, stachyurin, strictinin, tannic acid, tellimagrandin II |
| Condensed tannins | polymer chains of flavonoid units | proanthocyanidin, prodelphinidin, profisetinidin, proguibourtinidin, prorobinetidin |

The amount of a flavonoid included in a fluid composition disclosed in the present specification is an amount effective to reduce or prevent degradation of a matrix polymer disclosed in the present specification. As such, the amount of a flavonoid included in a fluid composition disclosed in the present specification is between about 0.1% to about 10% by weight of the total composition. In addition, a fluid composition disclosed in the present specification may comprise a single flavonoid, or a plurality of flavonoid. Further, a fluid composition disclosed in the present specification comprises a flavonoid that is pharmaceutically acceptable.

Thus in an embodiment, a fluid composition comprises a pharmaceutically acceptable flavonoid that can reduce or prevent degradation of a matrix polymer. In aspects of this embodiment, a fluid composition comprises a pharmaceutically acceptable C-methylated flavonoid, a pharmaceutically acceptable O-methylated flavonoid, a pharmaceutically acceptable isoflavonoid, a pharmaceutically acceptable neoflavonoid, a pharmaceutically acceptable flavonolignan, a pharmaceutically acceptable furanoflavonoid, a pharmaceutically acceptable pyranoflavonoid, a pharmaceutically acceptable methylenedioxyflavonoid, a pharmaceutically acceptable prenylated flavonoid, a pharmaceutically acceptable aurone, a pharmaceutically acceptable flavone, a pharmaceutically acceptable flavonol, a pharmaceutically acceptable flavanone, a pharmaceutically acceptable flavanonol, a pharmaceutically acceptable flavan-3-ol, a pharmaceutically acceptable flavan-4-ol, a pharmaceutically acceptable leucoanthocyanidin, a pharmaceutically acceptable anthocyanidin, and a pharmaceutically acceptable tannin.

In another embodiment, a fluid composition comprises a single flavonoid that can reduce or prevent degradation of a matrix polymer. In yet another embodiment, a fluid composition comprises a plurality of flavonoids, each of which can reduce or prevent the degradation of a matrix polymer. In aspects of this embodiment, a fluid composition comprises one or more flavonoids, two or more flavonoids, three or more flavonoids, four or more flavonoids, or five or more flavonoids. In other aspects of this embodiment, a fluid composition comprises one to five flavonoids, two to five flavonoids, three to five flavonoids, two to four flavonoids, two to five flavonoids, or three to five flavonoids.

In yet another embodiment, a fluid composition comprises a flavonoid in an amount sufficient to reduce or prevent degradation of a matrix polymer. In aspects of this embodiment, a fluid composition comprises a flavonoid in an amount of, e.g., about 0.1% (w/v) of the composition, about 0.2% (w/v) of the composition, about 0.3% (w/v) of the composition, about 0.4% (w/v) of the composition, about 0.5% (w/v) of the composition, about 0.6% (w/v) of the composition, about 0.7% (w/v) of the composition, about 0.8% (w/v) of the composition, about 0.9% (w/v) of the composition, about 1.0% (w/v) of the composition, about 2.0% (w/v) of the composition, about 3.0% (w/v) of the composition, about 4.0% (w/v) of the composition, about 5.0% (w/v) of the composition, about 6.0% (w/v) of the composition, about 7.0% (w/v) of the composition, about 8.0% (w/v) of the composition, about 9.0% (w/v) of the composition, or about 10% (w/v) of the composition. In other aspects, a fluid composition comprises a flavonoid in an amount of, e.g., at least 0.1% (w/v) of the composition, at least 0.2% (w/v) of the composition, at least 0.3% (w/v) of the composition, at least 0.4% (w/v) of the composition, at least 0.5% (w/v) of the composition, at least 0.6% (w/v) of the composition, at least 0.7% (w/v) of the composition, at least 0.8% (w/v) of the composition, at least 0.9% (w/v) of the composition, at least 1.0% (w/v) of the composition, at least 2.0% (w/v) of the composition, at least 3.0% (w/v) of the composition, at least 4.0% (w/v) of the composition, at least 5.0% (w/v) of the composition, at least 6.0% (w/v) of the composition, at least 7.0% (w/v) of the composition, at least 8.0% (w/v) of the composition, at least 9.0% (w/v) of the composition, or at least 10% (w/v) of the composition. In yet other aspects, a fluid composition comprises a flavonoid in an amount of, e.g., at most 0.1% (w/v) of the composition, at most 0.2% (w/v) of the composition, at most 0.3% (w/v) of the composition, at most 0.4% (w/v) of the composition, at most 0.5% (w/v) of the composition, at most 0.6% (w/v) of the composition, at most 0.7% (w/v) of the composition, at most 0.8% (w/v) of the composition, at most 0.9% (w/v) of the composition, at most 1.0% (w/v) of the composition, at most 2.0% (w/v) of the composition, at most 3.0% (w/v) of the composition, at most 4.0% (w/v) of the composition, at most 5.0% (w/v) of the composition, at most 6.0% (w/v) of the composition, at most 7.0% (w/v) of the composition, at most 8.0% (w/v) of the composition, at most 9.0% (w/v) of the composition, or at most 10% (w/v) of the composition. In still other aspects, a fluid composition comprises a flavonoid in an amount of, e.g., about 0.1% (w/v) to about 1.0% (w/v) of the composition, about 0.1% (w/v) to about 2.0% (w/v) of the composition, about 0.1% (w/v) to about 3.0% (w/v) of the composition, about 0.1% (w/v) to about 4.0% (w/v) of the composition, about 0.1% (w/v) to about 5.0% (w/v) of the composition, about 0.2% (w/v) to about 0.9% (w/v) of the composition, about 0.2% (w/v) to about 1.0% (w/v) of the composition, about 0.2% (w/v) to about 2.0% (w/v) of the composition, about 0.5% (w/v) to about 1.0% (w/v) of the composition, or about 0.5% (w/v) to about 2.0% (w/v) of the composition.

Aspects of the present specification provide, in part, a fluid composition that can optionally comprise or not comprise another active ingredient. As used herein, the term "active ingredient" includes but is not limited to a drug. A drug can generally be defined as a chemical substance used in the treatment, cure, prevention, or diagnosis of disease or used to otherwise enhance physical or mental well-being.

Aspects of the present specification provide, in part, a fluid composition that can optionally comprise or not comprise an anti-itch agent. The amount of an anti-itch agent included in a fluid composition disclosed in the present specification is an amount effective to mitigate an itch response experienced by an individual upon administration of the composition. As such, the amount of an anti-itch agent included in a fluid composition disclosed in the present specification is between about 0.1% to about 5% by weight of the total composition. Non-limiting examples of anti-itch agents include methyl sulphonyl methane, sodium bicarbonate, calamine, allantoin, kaolin, peppermint, tea tree oil and combinations thereof.

Thus in an embodiment, a fluid composition comprises a matrix polymer, a stabilizing component, and an anti-itch agent. In aspects of this embodiment, a fluid composition comprises a matrix polymer, a stabilizing component, and an anti-itch agent where the amount of anti-itch agent present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and an anti-itch agent where the amount of anti-itch agent present is about 0.3%. In another aspect of this embodiment, a fluid composition comprises a matrix polymer, a stabilizing component, and methyl sulphonyl methane, sodium bicarbonate, calamine, allantoin, kaolin, peppermint, tea tree oil, or combinations thereof. In aspects of this embodiment, a fluid composition comprises a matrix polymer, a stabilizing component, and a methyl sulphonyl methane, sodium bicarbonate, calamine, allantoin, kaolin, peppermint, tea tree oil, or combinations thereof where the amount of methyl sulphonyl methane, sodium bicarbonate, calamine, allantoin, kaolin, peppermint, or tea tree oil present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and a methyl sulphonyl methane, sodium bicarbonate, calamine, allantoin, kaolin, peppermint, tea tree oil, or combinations thereof where the amount of methyl sulphonyl methane, sodium bicarbonate, calamine, allantoin, kaolin, peppermint, or tea tree oil present is about 0.3%. In another embodiment, a fluid composition comprises a matrix polymer, a stabilizing component, but not an anti-itch agent.

Aspects of the present specification provide, in part, a fluid composition that can optionally comprise or not comprise an anti-cellulite agent. The amount of an anti-cellulite agent included in a fluid composition disclosed in the present specification is an amount effective to mitigate a fatty deposit experienced by an individual upon administration of the composition. As such, the amount of an anti-cellulite agent included in a fluid composition disclosed in the present specification is between about 0.1% to about 5% by weight of the total composition. Non-limiting examples of anti-cellulite agents include forskolin, xanthine compounds such as, but not limited to, caffeine, theophylline, theobromine, and aminophylline, and combinations thereof.

Thus in an embodiment, a fluid composition comprises a matrix polymer, a stabilizing component, and an anti-cellulite agent. In aspects of this embodiment, a fluid composition comprises a matrix polymer, a stabilizing component, and an anti-cellulite agent where the amount of anti-cellulite agent present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and an anti-cellulite agent where the amount of anti-cellulite agent present is about 0.3%. In another aspect of this embodiment, a fluid composition comprises a matrix polymer, a stabilizing component, and forskolin, a xanthine compound, or combinations thereof. In aspects of this embodiment, a fluid composition comprises a matrix polymer, a stabilizing component, and a forskolin, a xanthine compound, or combinations thereof where the amount of forskolin or a xanthine compound present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and a forskolin, a xanthine compound, or combinations thereof where the amount of forskolin or a xanthine compound present is about 0.3%. In another embodiment, a fluid composition comprises a matrix polymer, a stabilizing component, but not an anti-cellulite agent.

Aspects of the present specification provide, in part, a fluid composition that can optionally comprise or not comprise an anti-scarring agent. The amount of an anti-scarring agent included in a fluid composition disclosed in the present specification is an amount effective to mitigate a scaring response experienced by an individual upon administration of the composition. As such, the amount of an anti-scarring agent included in a fluid composition disclosed in the present specification is between about 0.1% to about 5% by weight of the total composition. Non-limiting examples of anti-scarring agents include IFN-γ, fluorouracil, poly(lactic-co-glycolic acid), methylated polyethylene glycol, polylactic acid, polyethylene glycol and combinations thereof.

Thus in an embodiment, a fluid composition comprises a matrix polymer, a stabilizing component, and an anti-scarring agent. In aspects of this embodiment, a fluid composition comprises a matrix polymer, a stabilizing component, and an anti-scarring agent where the amount of anti-scarring agent present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and an anti-scarring agent where the amount of anti-scarring agent present is about 0.3%. In another aspect of this embodiment, a fluid composition comprises a matrix polymer, a stabilizing component, and IFN-γ, fluorouracil, poly(lactic-co-glycolic acid), methylated polyethylene glycol, polylactic acid, polyethylene glycol, or combinations thereof. In aspects of this embodiment, a fluid composition comprises a matrix polymer, a stabilizing component, and a IFN-γ, fluorouracil, poly(lactic-co-glycolic acid), methylated polyethylene glycol, polylactic acid, polyethylene glycol, or combinations thereof where the amount of IFN-γ, fluorouracil, poly(lactic-co-glycolic acid), methylated polyethylene glycol, polylactic acid, or polyethylene glycol present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and a IFN-γ, fluorouracil, poly(lactic-co-glycolic acid), methylated polyethylene glycol, polylactic acid, polyethylene glycol, or combinations thereof where the amount of IFN-γ, fluorouracil, poly(lactic-co-glycolic acid), methylated polyethylene glycol, polylactic acid, or polyethylene glycol present is about 0.3%. In another embodiment, a fluid composition comprises a matrix polymer, a stabilizing component, but not an anti-scarring agent.

Aspects of the present specification provide, in part, a fluid composition that can optionally comprise or not comprise an anti-inflammatory agent. The amount of an anti-inflammatory agent included in a fluid composition disclosed in the present specification is an amount effective to mitigate an inflammatory response experienced by an individual upon administration of the composition. As such, the amount of an anti-inflammatory agent included in a fluid composition disclosed in the present specification is between about 0.1% to about 5% by weight of the total composition. Non-limiting examples of anti-inflammatory agents include dexamethasone, prednisolone, corticosterone, budesonide, estrogen, sulfasalazine, mesalamine and combinations thereof.

Thus in an embodiment, a fluid composition comprises a matrix polymer, a stabilizing component, and an anti-inflammatory agent. In aspects of this embodiment, a fluid composition comprises a matrix polymer, a stabilizing component, and an anti-inflammatory agent where the amount of anti-inflammatory agent present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and an anti-inflammatory agent where the amount of anti-inflammatory agent present is about 0.3%. In another aspect of this embodiment, a fluid composition comprises a matrix polymer, a stabilizing component, and dexamethasone, prednisolone, corticosterone, budesonide, estrogen, sulfasalazine, mesalamine, or combinations thereof. In aspects of this embodiment, a fluid composition comprises a matrix polymer, a stabilizing component, and a dexamethasone, prednisolone, corticosterone, budesonide, estrogen, sulfasalazine, mesalamine, or combinations thereof where the amount of dexamethasone, prednisolone, corticosterone, budesonide, estrogen, sulfasalazine, or mesalamine present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and a dexamethasone, prednisolone, corticosterone, budesonide, estrogen, sulfasalazine, mesalamine, or combinations thereof where the amount of dexamethasone, prednisolone, corticosterone, budesonide, estrogen, sulfasalazine, or mesalamine present is about 0.3%. In another embodiment, a fluid composition comprises a matrix polymer, a stabilizing component, but not an anesthetic agent.

Aspects of the present specification provide, in part, a fluid composition that can optionally comprise or not comprise an anesthetic agent. An anesthetic agent is preferably a local anesthetic agent, i.e., an anesthetic agent that causes a reversible local anesthesia and a loss of nociception, such as, e.g., aminoamide local anesthetics and aminoester local anesthetics. The amount of an anesthetic agent included in a fluid composition disclosed in the present specification is an amount effective to mitigate pain experienced by an individual upon administration of the composition. As such, the amount of an anesthetic agent included in a fluid composition disclosed in the present specification is between about 0.1% to about 5% by weight of the total composition. Non-limiting examples of anesthetic agents include lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, combinations thereof, and salts thereof. Non-limiting examples of aminoester local anesthetics include procaine, chloroprocaine, cocaine, cyclomethycaine, dimethocaine (larocaine), propoxycaine, procaine (novocaine), proparacaine, tetracaine (amethocaine). Non-limiting examples of aminoamide local anesthetics include articaine, bupivacaine, cinchocaine (dibucaine), etidocaine, levobupivacaine, lidocaine (lignocaine), mepivacaine, piperocaine, prilocaine, ropivacaine, and trimecaine. A non-limiting example of a combination local anesthetic is lidocaine/prilocaine (EMLA).

Thus in an embodiment, a fluid composition comprises a matrix polymer, a stabilizing component, and an anesthetic agent and salts thereof. In aspects of this embodiment, a fluid composition comprises a matrix polymer, a stabilizing component, and an aminoamide local anesthetic and salts thereof or an aminoester local anesthetic and salts thereof. In other aspects of this embodiment, a fluid composition comprises a matrix polymer, a stabilizing component, and procaine, chloroprocaine, cocaine, cyclomethycaine, dimethocaine, propoxycaine, procaine, proparacaine, tetracaine, or salts thereof. In yet other aspects of this embodiment, a fluid composition comprises a matrix polymer, a stabilizing component, and articaine, bupivacaine, cinchocaine, etidocaine, levobupivacaine, lidocaine, mepivacaine, piperocaine, prilocaine, ropivacaine, trimecaine, or salts thereof. In still other aspects of this embodiment, a fluid composition comprises a matrix polymer, a stabilizing component, and lidocaine/prilocaine combination.

In other aspects of this embodiment, a fluid composition comprises a matrix polymer, a stabilizing component, and an anesthetic agent where the amount of anesthetic agent present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and an anesthetic agent where the amount of anesthetic agent present is about 0.3%. In other aspects of this embodiment, a fluid composition comprises a matrix polymer, a stabilizing component, and an aminoamide local anesthetic and salts thereof or an aminoester local anesthetic and salts thereof where the amount of the local anesthetic present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and an aminoamide local anesthetic and salts thereof or an aminoester local anesthetic and salts thereof where the amount of the local anesthetic agent present is about 0.3%.

In another aspect of this embodiment, a fluid composition comprises a matrix polymer, a stabilizing component, and lidocaine or a lidocaine salt. In aspects of this embodiment, a fluid composition comprises a matrix polymer, a stabilizing component, and a lidocaine or a lidocaine salt where the amount of lidocaine or a lidocaine salt present is about 0.1% (w/v) to about 5% (w/v) of the total composition, about 0.1% (w/v) to about 1% (w/v) of the total composition, or about 0.1% (w/v) to about 0.5% (w/v) of the total composition. In other aspects of this embodiment, a fluid composition comprises a matrix polymer, a stabilizing component, and a lidocaine or a lidocaine salt where the amount of lidocaine or a lidocaine salt present is about 0.3%.

In another embodiment, a fluid composition comprises a matrix polymer, a stabilizing component, but not an anesthetic agent.

Aspects of the present specification provide, in part, a fluid composition disclosed in the present specification exhibiting a complex modulus, an elastic modulus, a viscous modulus and a tan δ. Matrix polymers disclosed in the present specification are viscoelastic in that the composition has an elastic component (solid-like such as, e.g., crosslinked matrix polymer) and a viscous component (liquid-like such as, e.g., uncrosslinked matrix polymer) when a force is applied (stress, deformation). The rheological attribute that described this property is the complex modulus (G*), which defines a fluid compositions total resistance to deformation. The complex modulus can be defined as the sum of the elastic modulus (G') and the viscous modulus (G"). Falcone, et al., *Temporary Polysaccharide Dermal Fillers: A Model for Persistence Based on Physical Properties*, Dermatol Surg. 35(8): 1238-1243 (2009); Tezel, supra, 2008; Kablik, supra, 2009; Beasley, supra, 2009; each of which is hereby incorporated by reference in its entirety. Elastic modulus characterizes the firmness of a composition and is also known as the storage modulus because it describes the storage of energy from the motion of the composition. The elastic modulus describes the interaction between elasticity and strength (G'=stress/strain) and, as such, provides a quantitative measurement of a composition's hardness or softness. Although depending on the speed at which the force is applied, a stiffer composition will have a higher elastic modulus and it will take a greater force to deform the material a given distance, such as, e.g., an injection.

Viscous modulus is also known as the loss modulus because it describes the energy that is lost as viscous dissipation. Tan δ is the ratio of the viscous modulus and the elastic modulus, tan δ=G'/G". Falcone, supra, 2009. For tan δ values disclosed in the present specification, a tan δ is obtained from the dynamic modulus at a frequency of 0.628 rad/s. A lower tan δ corresponds to a stiffer, harder, or more elastic composition.

Thus, in an embodiment, a fluid composition exhibits a complex modulus. In aspects of this embodiment, a fluid composition exhibits a complex modulus of, e.g., about 25 Pa, about 50 Pa, about 75 Pa, about 100 Pa, about 125 Pa, about 150 Pa, about 175 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, or about 800 Pa. In other aspects of this embodiment, a fluid composition exhibits a complex modulus of, e.g., at most 25 Pa, at most 50 Pa, at most 75 Pa, at most 100 Pa, at most 125 Pa, at most 150 Pa, at most 175 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, at most 700 Pa, at most 750 Pa, or at most 800 Pa. In yet other aspects of this embodiment, a fluid composition exhibits a complex modulus of, e.g., about 25 Pa to about 150 Pa, about 25 Pa to about 300 Pa, about 25 Pa to about 500 Pa, about 25 Pa to about 800 Pa, about 125 Pa to about 300 Pa, about 125 Pa to about 500 Pa, or about 125 Pa to about 800 Pa.

In another embodiment, a fluid composition exhibits an elastic modulus. In aspects of this embodiment, a fluid composition exhibits an elastic modulus of, e.g., about 25 Pa, about 50 Pa, about 75 Pa, about 100 Pa, about 125 Pa, about 150 Pa, about 175 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, or about 800 Pa. In other aspects of this embodiment, a fluid composition exhibits an elastic modulus of, e.g., at most 25 Pa, at most 50 Pa, at most 75 Pa, at most 100 Pa, at most 125 Pa, at most 150 Pa, at most 175 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, at most 700 Pa, at most 750 Pa, or at most 800 Pa. In yet other aspects of this embodiment, a fluid composition exhibits an elastic modulus of, e.g., about 25 Pa to about 150 Pa, about 25 Pa to about 300 Pa, about 25 Pa to about 500 Pa, about 25 Pa to about 800 Pa, about 125 Pa to about 300 Pa, about 125 Pa to about 500 Pa, or about 125 Pa to about 800 Pa.

In another embodiment, a fluid composition exhibits a viscous modulus. In aspects of this embodiment, a fluid composition exhibits a viscous modulus of, e.g., about 10 Pa, about 20 Pa, about 30 Pa, about 40 Pa, about 50 Pa, about 60 Pa, about 70 Pa, about 80 Pa, about 90 Pa, about 100 Pa, about 110 Pa, about 120 Pa, about 130 Pa, about 140 Pa, or about 150 Pa. In other aspects of this embodiment, a fluid composition exhibits a viscous modulus of, e.g., at most 10 Pa, at most 20 Pa, at most 30 Pa, at most 40 Pa, at most 50 Pa, at most 60 Pa, at most 70 Pa, at most 80 Pa, at most 90 Pa, at most 100 Pa, at most 110 Pa, at most 120 Pa, at most 130 Pa, at most 140 Pa, or at most 150 Pa. In yet other aspects of this embodiment, a fluid composition exhibits a viscous modulus of, e.g., about 10 Pa to about 30 Pa, about 10 Pa to about 50 Pa, about 10 Pa to about 100 Pa, about 10 Pa to about 150 Pa, or about 70 Pa to about 100 Pa.

In another embodiment, a fluid composition disclosed in the present specification exhibiting a tan δ. In aspects of this embodiment, a fluid composition exhibits a tan δ of, e.g., about 0.1, about 0.2, about 0.3, about 0.4, about 0.5, about 0.6, about 0.7, about 0.8, about 0.9, or about 1.0. In other aspects of this embodiment, a fluid composition exhibits a tan δ of, e.g., at most 0.1, at most 0.2, at most 0.3, at most 0.4, at most 0.5, at most 0.6, at most 0.7, at most 0.8, at most 0.9, or at most 1.0. In yet other aspects of this embodiment, a fluid composition exhibits a tan δ of, e.g., about 0.1 to about 0.3, about 0.3 to about 0.5, about 0.3 to about 0.6, about 0.1 to about 0.5, or about 0.1 to about 0.6.

Aspects of the present specification provide, in part, a fluid composition disclosed in the present specification exhibiting a dynamic viscosity. Viscosity is resistance of a fluid to shear or flow caused by either shear stress or tensile stress. Viscosity describes a fluid's internal resistance to flow caused by intermolecular friction exerted when layers of fluids attempt to slide by one another and may be thought of as a measure of fluid friction. The less viscous the fluid, the greater its ease of movement (fluidity).

Viscosity can be defined in two ways; dynamic viscosity (μ, although q is sometimes used) or kinematic viscosity (v). Dynamic viscosity, also known as absolute or complex viscosity, is the tangential force per unit area required to move one horizontal plane with respect to the other at unit velocity when maintained a unit distance apart by the fluid. The SI physical unit of dynamic viscosity is the Pascal-second (Pa·s), which is identical to N·m−2·s. Dynamic viscosity can be expressed as $\tau = \mu dv_x/dz$, where $\tau$=shearing stress, $\mu$=dynamic viscosity, and $dv_x/dz$ is the velocity gradient over time. For example, if a fluid with a viscosity of one Pa·s is placed between two plates, and one plate is pushed sideways with a shear stress of one Pascal, it moves a distance equal to the thickness of the layer between the plates in one second. Dynamic viscosity symbolize by is also used, is measured with various types of rheometers, devices used to measure the way in which a liquid, suspension or slurry flows in response to applied forces.

Kinematic viscosity (v) is the ratio of dynamic viscosity to density, a quantity in which no force is involved and is defined as follows: $v = \mu/\rho$, where $\mu$ is the dynamic viscosity $\rho$ is density with the SI unit of $kg/m^3$. Kinematic viscosity is usually measured by a glass capillary viscometer as has an SI unit of $m^2/s$.

The viscosity of a fluid is highly temperature dependent and for either dynamic or kinematic viscosity to be meaningful, the reference temperature must be quoted. For the viscosity values disclosed in the present specification, a dynamic viscosity is measured at 1 Pa with a cone/plane geometry 2°/40 cm and a temperature of 20° C. Examples of the dynamic viscosity of various fluids at 20° C. is as follows: water is about $1.0 \times 10^{-3}$ Pa·s, blood is about $3\text{-}4 \times 10^{-3}$ Pa·s, vegetable oil is about $60\text{-}85 \times 10^{-3}$ Pa·s, motor oil SE 30 is about 0.2 Pa·s, glycerin is about 1.4 Pa·s, maple syrup is about 2-3 Pa·s, honey is about 10 Pa·s, chocolate syrup is about 10-25 Pa·s, peanut butter is about 150-250 Pa·s, lard is about 1,000 Pa·s, vegetable shortening is about 1,200 Pa·s, and tar is about 30,000 Pa·s.

Thus, in an embodiment, a fluid composition comprising a matrix polymer and a stabilizing component exhibits a dynamic viscosity. In aspects of this embodiment, a fluid composition comprising a matrix polymer and a stabilizing component exhibits a dynamic viscosity of, e.g., about 10 Pa·s, about 20 Pa·s, about 30 Pa·s, about 40 Pa·s, about 50 Pa·s, about 60 Pa·s, about 70 Pa·s, about 80 Pa·s, about 90 Pa·s, about 100 Pa·s, about 125 Pa·s, about 150 Pa·s, about 175 Pa·s, about 200 Pa·s, about 225 Pa·s, about 250 Pa·s, about 275 Pa·s, about 300 Pa·s, about 400 Pa·s, about 500 Pa·s, about 600 Pa·s, about 700 Pa·s, about 750 Pa·s, about 800 Pa·s, about 900 Pa·s, about 1,000 Pa·s, about 1,100 Pa·s, or about 1,200 Pa·s. In other aspects of this embodiment, a fluid composition comprising a matrix polymer and a stabilizing component exhibits a dynamic viscosity of, e.g., at most 10 Pa·s, at most 20 Pa·s, at most 30 Pa·s, at most 40 Pa·s, at most 50 Pa·s, at most 60 Pa·s, at most 70 Pa·s, at most 80 Pa·s, at most 90 Pa·s, at most 100 Pa·s, at most 125 Pa·s, at most 150 Pa·s, at most 175 Pa·s, at most 200 Pa·s, at most 225 Pa·s, at most 250 Pa·s, at most 275 Pa·s, at most 300 Pa·s, at most 400 Pa·s, at most 500 Pa·s, at most 600 Pa·s, at most 700 Pa·s, at most 750 Pa·s, at most 800 Pa·s, at most 900 Pa·s, or at most 1000 Pa·s. In yet other aspects of this embodiment, a fluid composition comprising a matrix polymer and a stabilizing component exhibits a dynamic viscosity of, e.g., about 10 Pa·s to about 100 Pa·s, about 10 Pa·s to about 150 Pa·s, about 10 Pa·s to about 250 Pa·s, about 50 Pa·s to about 100 Pa·s, about 50 Pa·s to about 150 Pa·s, about 50 Pa·s to about 250 Pa·s, about 100 Pa·s to about 500 Pa·s, about 100 Pa·s to about 750 Pa·s, about 100 Pa·s to about 1,000 Pa·s, about 100 Pa·s to about 1,200 Pa·s, about 300 Pa·s to about 500 Pa·s, about 300 Pa·s to about 750 Pa·s, about 300 Pa·s to about 1,000 Pa·s, or about 300 Pa·s to about 1,200 Pa·s.

Aspects of the present specification provide, in part, a fluid composition disclosed in the present specification that is injectable. As used herein, the term "injectable" refers to a fluid composition disclosed in the present specification having the properties necessary to administer the composition into a dermal region of an individual using an injection device with a fine needle. As used herein, the term "fine needle" refers to a needle that is 27 gauge or smaller. Injectability of a fluid composition disclosed in the present specification can be accomplished by sizing the fluid composition, as discussed below.

Thus, in an embodiment, a fluid composition comprising a matrix polymer and a stabilizing component, wherein the composition is injectable. In aspect of this embodiment, a fluid composition comprising a matrix polymer and a stabilizing component is injectable through a fine needle. In other aspects of this embodiment, a fluid composition comprising a matrix polymer and a stabilizing component is injectable through a needle of, e.g., about 27 gauge, about 30 gauge, or about 32 gauge. In yet other aspects of this embodiment, a fluid composition comprising a matrix polymer and a stabilizing component is injectable through a needle of, e.g., 27 gauge or smaller, 30 gauge or smaller, or 32 gauge or smaller. In still other aspects of this embodiment, a fluid composition comprising a matrix polymer and a stabilizing component is injectable through a needle of, e.g., about 27 gauge to about 32 gauge.

In other aspects of this embodiment, a fluid composition comprising a crosslinked matrix polymer where the mean particle size of the crosslinked matrix polymer is, e.g., about 200 μm, about 250 μm, about 300 μm, about 350 μm, about 400 μm, about 450 μm, about 500 μm, about 550 μm, about 600 μm, about 650 μm, about 700 μm, about 750 μm, or about 800 μm. In yet other aspects of this embodiment, a fluid composition comprising a crosslinked matrix polymer where the mean particle size of the crosslinked matrix polymer is, e.g., at most 200 μm, at most 250 μm, at most 300 μm, at most 350 μm, at most 400 μm, at most 450 μm, at most 500 μm, at most 550 μm, at most 600 μm, at most 650 μm, at most 700 μm, at most 750 μm, or at most 800 μm. In still other aspects of this embodiment, a fluid composition comprising a crosslinked matrix polymer where the mean particle size of the crosslinked matrix polymer is, e.g., about 200 μm to about 300 μm, about 300 μm to about 400 μm, about 400 μm to about 500 μm, about 500 μm to about 600 μm, about 600 μm to about 700 μm, about 700 μm to about 800 μm, about 200 μm to about 400 μm, about 200 μm to about 500 μm, about 200 μm to about 600 μm, about 200 μm to about 700 μm, about 200 μm to about 800 μm, about 300 μm to about 500 μm, about 300 μm to about 600 μm, about 300 μm to about 700 μm, or about 300 μm to about 800 μm.

Aspects of the present specification provide, in part, a fluid composition disclosed in the present specification exhibiting a physiologically-acceptable osmolarity. As used herein, the term "a physiologically-acceptable osmolarity" refers to an osmolarity in accord with, or characteristic of, the normal functioning of a living organism. As such, administration of a fluid composition disclosed in the present composition exhibits an osmolarity that has substantially no long term or permanent detrimental effect when administered to mammal. Osmolarity refers to the concentration of osmotically active solutes in solution. Osmolarity is expressed in terms of osmoles of osmotically active solute per liter of solvent (Osmol/L or Osm/L). Osmolarity is distinct from molarity because it measures moles of osmotically active solute particles rather than moles of solute. The distinction arises because some compounds can dissociate in solution, whereas others cannot. The osmolarity of a solution can be calculated from the following expression: Osmol/L=$\Sigma \phi \, \phi_i \eta_i C_i$, where $\phi$ is the osmotic coefficient, which accounts for the degree of non-ideality of the solution; $\eta$ is the number of particles (e.g. ions) into which a molecule dissociates; and C is the molar concentration of the solute; and i is the index representing the identity of a particular solute. The osmolarity of a composition disclosed in the present specification can be measured using a conventional method that measures solutions.

Aspects of the present specification provide, in part, a fluid composition disclosed in the present specification exhibiting a physiologically-acceptable osmolality. As used herein, the term "a physiologically-acceptable osmolality" refers to an osmolality in accord with, or characteristic of, the normal functioning of a living organism. As such, administration of a fluid composition disclosed in the present composition exhibits an osmolality that has substantially no long term or permanent detrimental effect when administered to mammal. Osmolality refers to the concentration of osmotically active solutes per kilo of water in the body and is expressed in terms of osmoles of osmotically active solute per kilogram of solvent (Osmol/kg or Osm/kg) and is equal to the sum of the molalities of all the solutes present in that solution. The osmolality of a solution can be measured using an osmometer. The most commonly used instrument in modern laboratories is a freezing point depression osmometer. This instruments measure the change in freezing point that occurs in a solution with increasing osmolality (freezing point depression osmometer) or the change in vapor pressure that occurs in a solution with increasing osmolality (vapor pressure depression osmometer).

Thus, in an embodiment, a fluid composition comprising a matrix polymer and a stabilizing component exhibit a physiologically-acceptable osmolarity. In aspects of this embodiment, a fluid composition comprising a matrix polymer and a stabilizing component exhibit an osmolarity of, e.g., about 100 mOsm/L, about 150 mOsm/L, about 200 mOsm/L, about 250 mOsm/L, about 300 mOsm/L, about 350 mOsm/L, about 400 mOsm/L, about 450 mOsm/L, or about 500 mOsm/L. In other aspects of this embodiment, a fluid composition comprising a matrix polymer and a stabilizing component exhibit an osmolarity of, e.g., at least 100 mOsm/L, at least 150 mOsm/L, at least 200 mOsm/L, at least 250 mOsm/L, at least 300 mOsm/L, at least 350 mOsm/L, at least 400 mOsm/L, at least 450 mOsm/L, or at least 500 mOsm/L. In yet other aspects of this embodiment, a fluid composition comprising a matrix polymer and a stabilizing component exhibit an osmolarity of, e.g., at most 100 mOsm/L, at most 150 mOsm/L, at most 200 mOsm/L, at most 250 mOsm/L, at most 300 mOsm/L, at most 350 mOsm/L, at most 400 mOsm/L, at most 450 mOsm/L, or at most 500 mOsm/L. In still other aspects of this embodiment, a fluid composition comprising a matrix polymer and a stabilizing component exhibit an osmolarity of, e.g., about 100 mOsm/L to about 500 mOsm/L, about 200 mOsm/L to about 500 mOsm/L, about 200 mOsm/L to about 400 mOsm/L, about 300 mOsm/L to about 400 mOsm/L, about 270 mOsm/L to about 390 mOsm/L, about 225 mOsm/L to about 350 mOsm/L, about 250 mOsm/L to about 325 mOsm/L, about 275 mOsm/L to about 300 mOsm/L, or about 285 mOsm/L to about 290 mOsm/L.

In another embodiment, a fluid composition comprising a matrix polymer and a stabilizing component exhibit a physiologically-acceptable osmolality. In aspects of this embodiment, a fluid composition comprising a matrix polymer and a stabilizing component exhibit an osmolality of, e.g., about 100 mOsm/kg, about 150 mOsm/kg, about 200 mOsm/kg, about 250 mOsm/kg, about 300 mOsm/kg, about 350 mOsm/kg, about 400 mOsm/kg, about 450 mOsm/kg, or about 500 mOsm/kg. In other aspects of this embodiment, a fluid composition comprising a matrix polymer and a stabilizing component exhibit an osmolality of, e.g., at least 100 mOsm/kg, at least 150 mOsm/kg, at least 200 mOsm/kg, at least 250 mOsm/kg, at least 300 mOsm/kg, at least 350 mOsm/kg, at least 400 mOsm/kg, at least 450 mOsm/kg, or at least 500 mOsm/kg. In yet other aspects of this embodiment, a fluid composition comprising a matrix polymer and a stabilizing component exhibit an osmolality of, e.g., at most 100 mOsm/kg, at most 150 mOsm/kg, at most 200 mOsm/kg, at most 250 mOsm/kg, at most 300 mOsm/kg, at most 350 mOsm/kg, at most 400 mOsm/kg, at most 450 mOsm/kg, or at most 500 mOsm/kg. In still other aspects of this embodiment, a fluid composition comprising a matrix polymer and a stabilizing component exhibit an osmolality of, e.g., about 100 mOsm/kg to about 500 mOsm/kg, about 200 mOsm/kg to about 500 mOsm/kg, about 200 mOsm/kg to about 400 mOsm/kg, about 300 mOsm/kg to about 400 mOsm/kg, about 270 mOsm/kg to about 390 mOsm/kg, about 225 mOsm/kg to about 350 mOsm/kg, about 250 mOsm/kg to about 325 mOsm/kg, about 275 mOsm/kg to about 300 mOsm/kg, or about 285 mOsm/kg to about 290 mOsm/kg.

Aspects of the present specification provide, in part, a fluid composition disclosed in the present specification that is a pharmaceutical composition. As used herein, the term "pharmaceutical composition" is synonymous with "pharmaceutically-acceptable composition" and refers to a therapeutically effective concentration of an active ingredient, such as, e.g., any of the matrix polymers disclosed in the present specification. A pharmaceutical composition comprising a matrix polymer active ingredient is useful for medical and veterinary applications. A pharmaceutical composition may be administered to a patient alone, or in combination with other supplementary active ingredients, agents, drugs or hormones.

Aspects of the present specification provide, in part, a fluid composition disclosed in the present specification that is a pharmaceutical composition comprising a pharmacologically acceptable excipient. As used herein, the term "pharmacologically acceptable excipient" is synonymous with "pharmacological excipient" or "excipient" and refers to any excipient that has substantially no long term or permanent detrimental effect when administered to mammal and encompasses compounds such as, e.g., stabilizing agent, a bulking agent, a cryo-protectant, a lyo-protectant, an additive, a vehicle, a carrier, a diluent, or an auxiliary. An excipient generally is mixed with an active ingredient, or permitted to dilute or enclose the active ingredient and can be a solid, semi-solid, or liquid agent. It is also envisioned that a pharmaceutical composition comprising a matrix polymer active ingredient can include one or more pharmaceutically acceptable excipients that facilitate processing of an active ingredient into pharmaceutically acceptable compositions. Insofar as any pharmacologically acceptable excipient is not incompatible with the matrix polymer active ingredient, its use in pharmaceutically acceptable compositions is contemplated. Non-limiting examples of pharmacologically acceptable excipients can be found in, e.g., Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

It is further envisioned that a pharmaceutical composition disclosed in the present specification may optionally include or not include, without limitation, other pharmaceutically acceptable components (or pharmaceutical components), including, without limitation, buffers, preservatives, tonicity adjusters, salts, antioxidants, osmolality adjusting agents, emulsifying agents, wetting agents, sweetening or flavoring agents, and the like.

Pharmaceutically acceptable buffer is any buffer that can be used to prepare a pharmaceutical composition disclosed in the present specification, provided that the resulting preparation is pharmaceutically acceptable. Non-limiting examples of pharmaceutically acceptable buffers include acetate buffers, borate buffers, citrate buffers, neutral buffered salines, phosphate buffers, and phosphate buffered salines. Any concentration of a pharmaceutically acceptable buffer can be useful in formulating a pharmaceutical composition disclosed in the present specification, with the proviso that a therapeutically effective amount of the matrix polymer active ingredient is recovered using this effective concentration of buffer. Non-limiting examples of concentrations of physiologically-acceptable buffers occur within the range of about 0.1 mM to about 900 mM. The pH of pharmaceutically acceptable buffers may be adjusted, provided that the resulting preparation is pharmaceutically acceptable. It is understood that acids or bases can be used to adjust the pH of a pharmaceutical composition as needed. Any buffered pH level can be useful in formulating a pharmaceutical composition, with the proviso that a therapeutically effective amount of the matrix polymer active ingredient is recovered using this effective pH level. Non-limiting examples of physiologically-acceptable pH occur within the range of about pH 5.5 to about pH 8.5.

Pharmaceutically acceptable antioxidants include, without limitation, sodium metabisulfite, sodium thiosulfate, acetylcysteine, butylated hydroxyanisole and butylated hydroxytoluene. Pharmaceutically acceptable preservatives include, without limitation, benzalkonium chloride, chlorobutanol, thimerosal, phenylmercuric acetate, phenylmercuric nitrate, a stabilized oxy chloro composition, such as, e.g., PURITE® (Allergan, Inc. Irvine, Calif.) and chelants, such as, e.g., DTPA or DTPA-bisamide, calcium DTPA, and CaNaDTPA-bisamide.

Tonicity adjustors useful in a pharmaceutical composition include, without limitation, salts such as, e.g., sodium chloride and potassium chloride; and glycerin. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention. Other non-limiting examples of pharmacologically acceptable components can be found in, e.g., Ansel, supra, (1999); Gennaro, supra, (2000); Hardman, supra, (2001); and Rowe, supra, (2003), each of which is hereby incorporated by reference in its entirety.

A pharmaceutical compositions disclosed in the present specification generally is administered as a pharmaceutical acceptable composition comprising a matrix polymer active ingredient. As used herein, the term "pharmaceutically acceptable" means any molecular entity or composition that does not produce an adverse, allergic or other untoward or unwanted reaction when administered to an individual.

Aspects of the present specification provide, in part, a method of making a fluid composition disclosed in the present specification. In an aspect, a method for making a fluid composition, the method comprising the steps of: a) combining a stabilizing component with a physiologically-acceptable buffer to make a stabilizing component-buffered solution; b) combining a matrix polymer with the stabilizing component-buffered solution to hydrate the matrix polymer, and; c) sizing the fluid composition. This method may, or may not, further comprise a step comprising titrating a stabilizing component-buffered solution to obtain a desired pH after step (a); a step comprising filtering the stabilizing component-buffered solution after step (a); a step (b) where combining a matrix polymer with the stabilizing component-buffered solution to hydrate the matrix polymer occurs by mixing the matrix polymer with the stabilizing component-buffered solution at a low speed for a relatively long period of time; a step (b) where combining a matrix polymer with the stabilizing component-buffered solution to hydrate the matrix polymer occurs by mixing the matrix polymer with the stabilizing component-buffered solution at a low speed for a relatively long period of time and then followed by a rest for a relative long period of time; a step (b) where combining a matrix polymer with the stabilizing component-buffered solution to hydrate the matrix polymer occurs by mixing the matrix polymer with the stabilizing component-buffered solution at a low speed for a relatively long period of time and then by mixing the matrix polymer with the stabilizing component-buffered solution using a cycle of alternating periods of agitation for a relatively short period of time followed by periods of rest for a relatively long period of time; a step (b) where combining a matrix polymer with the stabilizing component-buffered solution to hydrate the matrix polymer occurs by mixing the matrix polymer with the stabilizing component-buffered solution at a low speed for a relatively long period of time and then by mixing the matrix polymer with the stabilizing component-buffered solution using a cycle of alternating periods of agitation for a relatively short period of time followed by periods of rest for a relatively long period of time, and then followed by a rest for a relative long period of time; a step comprising degassing a fluid composition after step (b) or step (c); a step comprising filling a syringe with a fluid composition after step (c); and/or a step comprising sterilizing a syringe filled with a fluid composition after step (c).

Aspects of the present specification provide, in part, a fluid composition disclosed in the present specification made by a method disclosed in the present specification. In an aspect, a fluid composition comprises a matrix polymer and a stabilizing component wherein the fluid composition is made by a method comprising the steps of: a) combining a stabilizing component with a physiologically-acceptable buffer to make a stabilizing component-buffered solution; b) combining a matrix polymer with the stabilizing component-buffered solution to hydrate the matrix polymer, and; c) sizing the fluid composition. This method may, or may not, further comprise a step comprising titrating a stabilizing component-buffered solution to obtain a desired pH after step (a); a step comprising filtering the stabilizing component-buffered solution after step (a); a step (b) where combining a matrix polymer with the stabilizing component-buffered solution to hydrate the matrix polymer occurs by mixing the matrix polymer with the stabilizing component-buffered solution at a low speed for a relatively long period of time; a step (b) where combining a matrix polymer with the stabilizing component-buffered solution to hydrate the matrix polymer occurs by mixing the matrix polymer with the stabilizing component-buffered solution at a low speed for a relatively long period of time and then followed by a rest for a relative long period of time; a step (b) where combining a matrix polymer with the stabilizing component-buffered solution to hydrate the matrix polymer occurs by mixing the matrix polymer with the stabilizing component-buffered solution at a low speed for a relatively long period of time and then by mixing the matrix polymer with the stabilizing component-buffered solution using a cycle of alternating periods of agitation for a relatively short period of time followed by periods of rest for a relatively long period of time; a step (b) where combining a matrix polymer with the stabilizing component-buffered solution to hydrate the matrix polymer occurs by mixing the matrix polymer with the stabilizing component-buffered solution at a low speed for a relatively long period of time and then by mixing the matrix polymer with the stabilizing component-buffered solution using a cycle of alternating periods of agitation for a relatively short period of time followed by periods of rest for a relatively long period of time, and then followed by a rest for a relative long period of time; a step comprising degassing a fluid composition after step (b) or step (c); a step comprising filling a syringe with a fluid composition after step (c); and/or a step comprising sterilizing a syringe filled with a fluid composition after step (c).

Aspects of the present specification provide, in part, a method having a step of combining a stabilizing component with a physiologically-acceptable buffer to make a stabilizing component-buffered solution. A stabilizing component can be any one of the stabilizing components disclosed in the present specification. As used herein, the term "a physiologically-acceptable buffer" refers to a buffer in accord with, or characteristic of, the normal functioning of a living organism. As such, a buffer used to make a fluid composition disclosed in the present specification exhibits a buffering capacity that has substantially no long term or permanent detrimental effect when administered to mammal. Physiologically-acceptable buffers include, without limitation, acetate buffers, borate buffers, citrate buffers, neutral buffered salines, phosphate buffers, and phosphate buffered salines. In addition, the physiologically-acceptable buffer is at a concentration to achieve an effective buffering capacity. Non-limiting examples of a concentration to a physiologically-acceptable buffer to achieve an effective buffering capacity is from between about 0.1 mM to about 900 mM.

Thus, in an embodiment, a stabilizing component is combined with a physiologically-acceptable buffer to make a stabilizing component-buffered solution. In aspects of this embodiment, a stabilizing component is combined with an acetate buffer, a borate buffers, a citrate buffer, a neutral buffered saline, a phosphate buffer, or a phosphate buffered saline to make a stabilizing-buffered solution. In other an stabilizing component is combined with sodium chloride, sodium phosphate, or both.

In another embodiment, a physiologically-acceptable buffer is at a concentration necessary to achieve an effective buffering capacity. In aspects of this embodiment, a physiologically-acceptable buffer is at a concentration of, e.g., at least 0.1 mM, at least 0.2 mM, at least 0.3 mM, at least 0.4 mM, at least 0.5 mM, at least 0.6 mM, at least 0.7 mM, at least 0.8 mM, or at least 0.9 mM. In other aspects of this embodiment, a physiologically-acceptable buffer is at a concentration of, e.g., at least 1.0 mM, at least 2.0 mM, at least 3.0 mM, at least 4.0 mM, at least 5.0 mM, at least 6.0 mM, at least 7.0 mM, at least 8.0 mM, or at least 9.0 mM. In yet other aspects of this embodiment, a physiologically-acceptable buffer is at a concentration of, e.g., at least 10 mM, at least 20 mM, at least 30 mM, at least 40 mM, at least 50 mM, at least 60 mM, at least 70 mM, at least 80 mM, or at least 90 mM. In still other aspects of this embodiment, a physiologically-acceptable buffer is at a concentration of, e.g., at least 100 mM, at least 200 mM, at least 300 mM, at least 400 mM, at least 500 mM, at least 600 mM, at least 700 mM, at least 800 mM, or at least 900 mM.

In further aspects of this embodiment, a physiologically-acceptable buffer is at a concentration of, e.g., at most 0.1 mM, at most 0.2 mM, at most 0.3 mM, at most 0.4 mM, at most 0.5 mM, at most 0.6 mM, at most 0.7 mM, at most 0.8 mM, or at most 0.9 mM. In still other aspects of this embodiment, a physiologically-acceptable buffer is at a concentration of, e.g., at most 1.0 mM, at most 2.0 mM, at most 3.0 mM, at most 4.0 mM, at most 5.0 mM, at most 6.0 mM, at most 7.0 mM, at most 8.0 mM, or at most 9.0 mM. In yet other aspects of this embodiment, a physiologically-acceptable buffer is at a concentration of, e.g., at most 10 mM, at most 20 mM, at most 30 mM, at most 40 mM, at most 50 mM, at most 60 mM, at most 70 mM, at most 80 mM, or at most 90 mM. In still other aspects of this embodiment, a physiologically-acceptable buffer is at a concentration of, e.g., at most 100 mM, at most 200 mM, at most 300 mM, at most 400 mM, at most 500 mM, at most 600 mM, at most 700 mM, at most 800 mM, or at most 900 mM. In still further aspects of this embodiment, a physiologically-acceptable buffer is at a concentration of, e.g., about 0.1 mM to about 900 mM, 0.1 mM to about 500 mM, 0.1 mM to about 100 mM, 0.1 mM to about 90 mM, 0.1 mM to about 50 mM, 1.0 mM to about 900 mM, 1.0 mM to about 500 mM, 1.0 mM to about 100 mM, 1.0 mM to about 90 mM, or 1.0 mM to about 50 mM.

Aspects of the present specification provide, in part, a method having an optional step of titrating a stabilizing component-buffered solution to obtain a desired pH. A stabilizing component-buffered solution can be titrated to any physiologically-acceptable pH desired. As used herein, the term "a physiologically-acceptable pH" refers to a pH in accord with, or characteristic of, the normal functioning of a living organism. As such, a pH used to make a fluid composition disclosed in the present specification is a pH that has substantially no long term or permanent detrimental effect when administered to mammal. Non-limiting examples of physiologically-acceptable pH occur within the range of about pH 5.5 to about pH 8.5. It is understood that acids or bases can be used to adjust the pH of a stabilizing component-buffered solution.

Thus, in an embodiment, a stabilizing component-buffered solution is titrated to a physiologically-acceptable pH. In an aspect of this embodiment, a stabilizing component-buffered solution is titrated to pH of, e.g., at least about pH 5.0, at least about pH 5.5, at least about pH 6.0, at least about pH 6.5, at least about pH 7.0 or at about pH 7.5. In another aspect of this embodiment, a stabilizing component-buffered solution is titrated to pH of, e.g., at most about pH 5.0, at most about pH 5.5, at most about pH 6.0, at most about pH 6.5, at most about pH 7.0 or at most about pH 7.5. In yet another aspect of this embodiment, a stabilizing component-buffered solution is titrated to pH of, e.g., about pH 5.0 to about pH 8.0, an effective pH level is about pH 5.0 to about pH 7.0, an effective pH level is about pH 5.0 to about pH 6.0, is about pH 5.5 to about pH 8.0, an effective pH level is about pH 5.5 to about pH 7.0, an effective pH level is about pH 5.5 to about pH 5.0, is about pH 5.5 to about pH 7.5, an effective pH level is about pH 5.5 to about pH 6.5.

Aspects of the present specification provide, in part, a method having an optional step of filtering a stabilizing component-buffered solution to remove particulates and impurities. For example, a stabilizing component-buffered solution may, or may not, be filtered to remove particulates and impurities from the stabilizing component-buffered solution. The filters used should be of a pore size that sufficiently removes the particulates and impurities desired to be removed from a stabilizing component-buffered solution. Non-limiting examples of pore sizes are of the range of 5.0 μm or less.

Thus, in an embodiment, a stabilizing component-buffered solution is filtered to remove particulates and impurities. In an aspect of this embodiment, a stabilizing component-buffered solution is filtered through a pore size sufficient to remove particulates and impurities. In other aspects of this embodiment, a stabilizing component-buffered solution is filtered through a pore size of, e.g., about 0.1 μm or less, about 0.25 μm or less, about 0.5 μm or less, about 0.75 μm or less, about 1 μm or less, about 2 μm or less, about 3 μm or less, about 4 μm or less, or about 5 μm or less.

Aspects of the present specification provide, in part, a method having a step of combining a matrix polymer with a stabilizing component-buffered solution to hydrate the matrix polymer. A matrix polymer can be any one of the matrix polymers disclosed in the present specification, its salts, and/or mixtures thereof. A matrix polymer can be a partially crosslinked matrix polymer, a substantially uncrosslinked matrix polymer, a matrix polymer that is essentially free of a crosslinked matrix polymer, or a matrix polymer that is entirely free of a crosslinked matrix polymer as disclosed in the present specification. The source of the matrix polymer can be from a bacterial source or an animal source.

Combining a matrix polymer with a stabilizing component-buffered solution can be accomplished by any method with the proviso that the method used is sufficient to hydrate the matrix polymer in a manner that produces a fluid composition disclosed in the present specification. It is also understood that any method employed does not result in substantial degradation of matrix polymer as this is inconsistent with a fluid composition disclosed in the present specification. For example, the step of combining a matrix polymer with a stabilizing component-buffered solution can comprises mixing a matrix polymer with a stabilizing component-buffered solution at a low speed for a relatively long period of time. Non-limiting examples of a speed used for mixing is from about 50 rpm to about 500 rpm. The relatively long time period for agitation is a time period sufficient to effectively combine a matrix polymer with a stabilizing component-buffered solution to allow the matrix polymer to hydrate. Non-limiting examples of time periods for mixing at a relative low speed include from about 4 hours to about 16 hours. This combining step is performed at cool ambient temperature. Non-limiting examples of a cool ambient temperature include a temperature not exceeding about 25° C., such as, a temperature not exceeding about 20° C., a temperature not exceeding about 15° C., or a temperature not exceeding about 10° C. As another non-limiting example, a cool ambient temperature is a temperature from about 2° C. and about 8° C.

As another non-limiting example, the step of combining a matrix polymer with a stabilizing component-buffered solution may, or may not, involve a cycle of alternating periods of agitation for a relatively short period of time followed by periods of rest for a relatively long period of time. This agitation/rest step may be performed once in order to combine a matrix polymer with a stabilizing component-buffered solution composition, or may be performed for a plurality of times. For example, the agitation/rest step may be performed two or more times, five or more times, or ten or more times. Agitation of a matrix polymer with a stabilizing component-buffered solution can be accomplished by any method sufficient to agitate the composition including, without limitation, mechanical shaking, manual shaking, ultrasound, vibration, and the like, and combinations thereof. The relatively short time period for agitation is a time period sufficient to effectively combine a matrix polymer with a stabilizing component-buffered solution to create a fluid composition disclosed in the present specification. Non-limiting examples of time periods for agitation include from about 1 minute to about 15 minutes. Similarly, the relatively long time period for rest is a time period sufficient to effectively combine a matrix polymer with a stabilizing component-buffered solution to create a fluid composition disclosed in the present specification. Non-limiting examples of time periods for rest include from about 15 minute to about 180 minutes. For example, a matrix polymer with a stabilizing component-buffered solution composition can be agitated for about 1 minute and then allowed to rest for about 30 minutes. If such an agitation/rest step is used, it typically follows the combining step comprising a low speed for a relatively long period of time described above.

After combining a matrix polymer with a stabilizing component-buffered solution, this composition is allowed to rest for a relative long period of time. A relatively long time period for rest is a time period sufficient to effectively combine a matrix polymer with a stabilizing component-buffered solution to create a fluid composition disclosed in the present specification. Non-limiting examples of time periods for resting after the combining step include from about 4 hours to about 16 hours.

Thus, in an embodiment, a matrix polymer is combined with a stabilizing component-buffered solution in order to hydrate the matrix polymer. In an aspect of this embodiment, a matrix polymer is combined with a stabilizing component-buffered solution in order to hydrate the matrix polymer and achieve a smooth consistency of the composition. In other aspects of this embodiment, a stabilizing component-buffered solution is combined with a partially crosslinked matrix polymer, a substantially uncrosslinked matrix polymer, a matrix polymer that is essentially free of a crosslinked matrix polymer, or a matrix polymer that is entirely free of a crosslinked matrix polymer.

In another embodiment, a matrix polymer is combined with a stabilizing component-buffered solution by mixing the matrix polymer with the stabilizing component-buffered solution at a low speed for a relatively long period of time. In aspects of this embodiment, a matrix polymer is combined with a stabilizing component-buffered solution by mixing the matrix polymer with the stabilizing component-buffered solution at, e.g., about 50 rpm, about 100 rpm, about 150 rpm, about 200 rpm, about 250 rpm, about 300 rpm, about 350 rpm, about 400 rpm, about 450 rpm, or about 500 rpm for about 6 hours, 7 hours, 8 hours, 9 hours, 10 hours, 11 hours, 12 hours, 13 hours, or 14 hours. In other aspects of this embodiment, a matrix polymer is combined with a stabilizing component-buffered solution by mixing the matrix polymer with the stabilizing component-buffered solution at, e.g., about 50 rpm, about 100 rpm, about 150 rpm, about 200 rpm, about 250 rpm, about 300 rpm, about 350 rpm, about 400 rpm, about 450 rpm, or about 500 rpm for about 6 hours or more, 7 hours or more, 8 hours or more, 9 hours or more, 10 hours or more, 11 hours or more, 12 hours or more, 13 hours or more, or 14 hours or more. In yet other aspects of this embodiment, a matrix polymer is combined with a stabilizing component-buffered solution by mixing the matrix polymer with the stabilizing component-buffered solution at, e.g., at most 50 rpm, at most 100 rpm, at most 150 rpm, at most 200 rpm, at most 250 rpm, at most 300 rpm, at most 350 rpm, at most 400 rpm, at most 450 rpm, or at most 500 rpm for about 6 hours or more, 7 hours or more, 8 hours or more, 9 hours or more, 10 hours or more, 11 hours or more, 12 hours or more, 13 hours or more, or 14 hours or more. In still other aspects of this embodiment, a matrix polymer is combined with a stabilizing component-buffered solution by mixing the matrix polymer with the stabilizing component-buffered solution at about 50 rpm to about 500 rpm for about 8 hours to about 12 hours.

In another embodiment, a matrix polymer is combined with a stabilizing component-buffered solution by mixing the matrix polymer with the stabilizing component-buffered solution using a cycle of alternating periods of agitation for a relatively short period of time followed by periods of rest for a relatively long period of time. In aspects of this embodiment, a matrix polymer and a stabilizing component-buffered solution is agitated for about 1 minute, about 5 minutes, about 10 minutes, or about 15 minutes, and then allowed to rest for about 15 minutes, about 30 minutes, about 45 minutes, about 60 minutes, about 75 minutes, about 90 minutes, about 105 minutes, about 120 minutes, about 135 minutes, about 150 minutes, about 165 minutes, or about 180 minutes. In other aspects of this embodiment, a matrix polymer and a stabilizing component-buffered solution is agitated for about 1 minute or more, about 5 minutes or more, about 10 minutes or more, or about 15 minutes or more, and then allowed to rest for about 15 minutes or more, about 30 minutes or more, about 45 minutes or more, about 60 minutes or more, about 75 minutes or more, about 90 minutes or more, about 105 minutes, about 120 minutes or more, about 135 minutes or more, about 150 minutes or more, about 165 minutes or more, or about 180 minutes or more. In yet other aspects of this embodiment, a matrix polymer and a stabilizing component-buffered solution is agitated for at most 1 minute, at most 5 minutes, at most 10 minutes, or at most 15 minutes, and then allowed to rest for at most 15 minutes, at most 30 minutes, at most 45 minutes, at most 60 minutes, at most 75 minutes, at most 90 minutes, at most 105 minutes, at most 120 minutes, at most 135 minutes, at most 150 minutes, at most 165 minutes, or at most 180 minutes. In still other aspects of this embodiment, a matrix polymer and a stabilizing component-buffered solution is agitated for at most 1 minute, at most 5 minutes, at most 10 minutes, or at most 15 minutes, and then allowed to rest for about 15 minutes or more, about 30 minutes or more, about 45 minutes or more, about 60 minutes or more, about 75 minutes or more, about 90 minutes or more, about 105 minutes, about 120 minutes or more, about 135 minutes or more, about 150 minutes or more, about 165 minutes or more, or about 180 minutes or more. In further aspects of this embodiment, a matrix polymer and a stabilizing component-buffered solution is agitated for about 1 minute to about 15 minutes, and then allowed to rest for about 30 minutes to about 60 minutes.

Aspects of the present specification provide, in part, a method having a step of sizing the fluid composition. Sizing the fluid composition is particularly important if crosslinked matrix polymers are present because this step 1) produces a composition with a particular mean sized of gel particle, and/or 2) produces a composition with a smooth consistency as opposed to a granular consistency. In fluid compositions comprising a crosslinked matrix polymer, the initial crosslinking process produces a large gel mass that must be sized down in order to produce a composition that can be properly administered to an individual, such as, e.g., by injection. Sizing of gel particles can be accomplished by any method suitable to produce a fluid composition that can be properly administered into an individual. Non-limiting examples include sieving and homogenization. In a sieving method, a large gel mass included in a fluid composition is broken down by passing through a series of sieves or screens in order to size the gel particles. This method produces gel particles that have a well-defined average size. In a homogenization method, a large gel mass included in a fluid composition is broken down by recirculating the fluid composition between a first vessel and a second vessel through a narrow aperture. The recirculation of a fluid composition may comprise passing the composition from a first vessel into a second vessel through an orifice having any diameter sufficient to achieve a smooth fluid composition. Non-limiting examples of orifice diameters include about 2 mm to about 10 mm. The recirculating step can be performed once or a plurality of times, such as, e.g., from 2 to 10 times.

Thus, in an embodiment, a fluid composition is sized. In other aspects of this embodiment, a fluid composition is sized by sieving wherein after sizing the mean particle size of the crosslinked matrix polymer is, e.g., about 200 µm, about 250 µm, about 300 µm, about 350 µm, about 400 µm, about 450 µm, about 500 µm, about 550 µm, about 600 µm, about 650

μm, about 700 μm, about 750 μm, or about 800 μm. In yet other aspects of this embodiment, a fluid composition is sized by sieving wherein after sizing the mean particle size of the crosslinked matrix polymer is, e.g., at most 200 μm, at most 250 μm, at most 300 μm, at most 350 μm, at most 400 μm, at most 450 μm, at most 500 μm, at most 550 μm, at most 600 μm, at most 650 μm, at most 700 μm, at most 750 μm, or at most 800 μm. In still other aspects of this embodiment, a fluid composition is sized by sieving wherein after sizing the mean particle size of the crosslinked matrix polymer is, e.g., about 200 μm to about 300 μm, about 300 μm to about 400 μm, about 400 μm to about 500 μm, about 500 μm to about 600 μm, about 600 μm to about 700 μm, about 700 μm to about 800 μm, about 200 μm to about 400 μm, about 200 μm to about 500 μm, about 200 μm to about 600 μm, about 200 μm to about 700 μm, about 200 μm to about 800 μm, about 300 μm to about 500 μm, about 300 μm to about 600 μm, about 300 μm to about 700 μm, or about 300 μm to about 800 μm.

In other aspects of this embodiment, a fluid composition comprising a crosslinked matrix polymer is sized by sieving wherein after sizing the mean particle size of the crosslinked matrix polymer is, e.g., about 200 μm, about 250 μm, about 300 μm, about 350 μm, about 400 μm, about 450 μm, about 500 μm, about 550 μm, about 600 μm, about 650 μm, about 700 μm, about 750 μm, or about 800 μm. In yet other aspects of this embodiment, a fluid composition comprising a crosslinked matrix polymer is sized by sieving wherein after sizing the mean particle size of the crosslinked matrix polymer is, e.g., at most 200 μm, at most 250 μm, at most 300 μm, at most 350 μm, at most 400 μm, at most 450 μm, at most 500 μm, at most 550 μm, at most 600 μm, at most 650 μm, at most 700 μm, at most 750 μm, or at most 800 μm. In still other aspects of this embodiment, a fluid composition comprising a crosslinked matrix polymer is sized by sieving wherein after sizing the mean particle size of the crosslinked matrix polymer is, e.g., about 200 μm to about 300 μm, about 300 μm to about 400 μm, about 400 μm to about 500 μm, about 500 μm to about 600 μm, about 600 μm to about 700 μm, about 700 μm to about 800 μm, about 200 μm to about 400 μm, about 200 μm to about 500 μm, about 200 μm to about 600 μm, about 200 μm to about 700 μm, about 200 μm to about 800 μm, about 300 μm to about 500 μm, about 300 μm to about 600 μm, about 300 μm to about 700 μm, or about 300 μm to about 800 μm.

In other aspects of this embodiment, a fluid composition is sized by recirculating between a first vessel and a second vessel through a narrow aperture wherein after recirculation the mean particle size of the crosslinked matrix polymer is, e.g., about 200 μm, about 250 μm, about 300 μm, about 350 μm, about 400 μm, about 450 μm, about 500 μm, about 550 μm, about 600 μm, about 650 μm, about 700 μm, about 750 μm, or about 800 μm. In yet other aspects of this embodiment, a fluid composition is sized by recirculating between a first vessel and a second vessel through a narrow aperture once wherein after recirculation the mean particle size of the crosslinked matrix polymer is, e.g., at most 200 μm, at most 250 μm, at most 300 μm, at most 350 μm, at most 400 μm, at most 450 μm, at most 500 μm, at most 550 μm, at most 600 μm, at most 650 μm, at most 700 μm, at most 750 μm, or at most 800 μm. In still other aspects of this embodiment, a fluid composition is sized by recirculating between a first vessel and a second vessel through a narrow aperture wherein after recirculation the mean particle size of the crosslinked matrix polymer is, e.g., about 200 μm to about 300 μm, about 300 μm to about 400 μm, about 400 μm to about 500 μm, about 500 μm to about 600 μm, about 600 μm to about 700 μm, about 700 μm to about 800 μm, about 200 μm to about 400 μm, about 200 μm to about 500 μm, about 200 μm to about 600 μm, about 200 μm to about 700 μm, about 200 μm to about 800 μm, about 300 μm to about 500 μm, about 300 μm to about 600 μm, about 300 μm to about 700 μm, or about 300 μm to about 800 μm.

In other aspects of this embodiment, a fluid composition comprising a crosslinked matrix polymer is sized by recirculating between a first vessel and a second vessel through a narrow aperture wherein after recirculation the mean particle size of the crosslinked matrix polymer is, e.g., about 200 μm, about 250 μm, about 300 μm, about 350 μm, about 400 μm, about 450 μm, about 500 μm, about 550 μm, about 600 μm, about 650 μm, about 700 μm, about 750 μm, or about 800 μm. In yet other aspects of this embodiment, a fluid composition comprising a crosslinked matrix polymer is sized by recirculating between a first vessel and a second vessel through a narrow aperture wherein after recirculation the mean particle size of the crosslinked matrix polymer is, e.g., at most 200 μm, at most 250 μm, at most 300 μm, at most 350 μm, at most 400 μm, at most 450 μm, at most 500 μm, at most 550 μm, at most 600 μm, at most 650 μm, at most 700 μm, at most 750 μm, or at most 800 μm. In still other aspects of this embodiment, a fluid composition comprising a crosslinked matrix polymer is sized by recirculating between a first vessel and a second vessel through a narrow aperture wherein after recirculation the mean particle size of the crosslinked matrix polymer is, e.g., about 200 μm to about 300 μm, about 300 μm to about 400 μm, about 400 μm to about 500 μm, about 500 μm to about 600 μm, about 600 μm to about 700 μm, about 700 μm to about 800 μm, about 200 μm to about 400 μm, about 200 μm to about 500 μm, about 200 μm to about 600 μm, about 200 μm to about 700 μm, about 200 μm to about 800 μm, about 300 μm to about 500 μm, about 300 μm to about 600 μm, about 300 μm to about 700 μm, or about 300 μm to about 800 μm.

In aspects of this embodiment, a fluid composition is sized by recirculating between a first vessel and a second vessel through a narrow aperture once. In aspects of this embodiment, a fluid composition is sized recirculating between a first vessel and a second vessel through a narrow aperture, e.g., twice, three times, four times, five times, six times, seven times, eight times, nine times, or ten times. In aspects of this embodiment, a fluid composition is sized by recirculating between a first vessel and a second vessel through a narrow aperture, e.g., twice, three times, four times, five times, six times, seven times, eight times, nine times, or ten times. In other aspects of this embodiment, a fluid composition is sized by recirculating between a first vessel and a second vessel through a narrow aperture, e.g., twice to ten times, twice to eight times, twice to six times, twice to four times, three times to five times, three times to six times, or three times to seven times.

In other aspects of this embodiment, a fluid composition is recirculated between a first vessel and a second vessel through a narrow aperture having a diameter of, e.g., about 2 mm, about 3 mm, about 4 mm, about 5 mm, about 6 mm, about 7 mm, about 8 mm, about 9 mm, or about 10 mm. In yet other aspects of this embodiment, a fluid composition is recirculated between a first vessel and a second vessel through a narrow aperture having a diameter of, e.g., at least 2 mm, at least 3 mm, at least 4 mm, at least 5 mm, at least 6 mm, at least 7 mm, at least 8 mm, at least 9 mm, or at least 10 mm. In still other aspects of this embodiment, a fluid composition is recirculated between a first vessel and a second vessel through a narrow aperture having a diameter of, e.g., at most 2 mm, at most 3 mm, at most 4 mm, at most 5 mm, at most 6 mm, at most 7 mm, at most 8 mm, at most 9 mm, or at most 10 mm.

In further aspects of this embodiment, a fluid composition is recirculated between a first vessel and a second vessel through a narrow aperture having a diameter of, e.g., about 2 mm to about 4 mm, about 2 mm to about 6 mm, about 2 mm to about 8 mm, or about 2 mm to about 10 mm.

Additional method steps in accordance with making a fluid composition disclosed in the present specification may, or may not, include degassing the composition, filling syringes with the composition, and sterilizing the composition.

Aspects of the present specification provide, in part, a method having an optional step of degassing a fluid composition disclosed in the present specification. Degassing a fluid composition disclosed in the present specification can be accomplished using a standard device based on conventional techniques and may be done under vacuum. Degassing is performed for a time period sufficient to remove the desired amount of gases from a fluid composition. Non-liming examples of sufficient time period for degassing include about 2 hours to about 8 hours.

Aspects of the present specification provide, in part, a method having an optional step of filling a syringe with a fluid composition disclosed in the present specification. Syringes useful according to the present description include any syringe known in the art for administering a therapeutically effective amount a fluid composition disclosed in the present specification into a dermal region, such as, e.g., a syringe having an internal volume of about 0.4 mL to about 3.0 mL. In addition the type of needle used in conjunction with the syringe is a needle sufficient to effectively administer a therapeutically effective amount of a fluid composition disclosed in the present specification into a dermal region, such as, e.g., a diameter of between about 18 G and about 40 G and a needle length of at about 2 mm or more in length.

Thus, in an embodiment, a fluid composition is filled into a syringe. In aspects of this embodiment, a fluid composition is filled into a syringe having an internal volume of about 0.4 mL, about 0.5 mL, about 0.6 mL, about 0.7 mL, about 0.8 mL, about 0.9 mL, about 1 mL, about 1 mL, about 1.5 mL, about 2 mL, about 2.5 mL, or about 3 mL. In other aspects of this embodiment, a fluid composition is filled into a syringe having an internal volume of at least 0.4 mL, at least 0.5 mL, at least 0.6 mL, at least 0.7 mL, at least 0.8 mL, at least 0.9 mL, at least 1 mL, at least 1 mL, at least 1.5 mL, at least 2 mL, at least 2.5 mL, or at least 3 mL. In yet other aspects of this embodiment, a fluid composition is filled into a syringe having an internal volume of about 0.4 mL to about 3 mL, about 0.5 mL to about 1.5 mL, or about 0.8 mL to about 2.5 mL. In another aspect, a syringe filled with a fluid composition is combined with a needle. In aspects of this embodiment, a syringe filled with a fluid composition is combined with a needle having a diameter of about 18 G, about 22 G, about 25 G, about 28 G, about 30 G, about 33 G, or about 40 G. In other aspects of this embodiment, a syringe filled with a fluid composition is combined with a needle having a diameter of about 18 G or smaller, about 22 G or smaller, about 25 G or smaller, about 28 G or smaller, about 30 G or smaller, about 33 G or smaller, or about 40 G or smaller. In yet other aspects of this embodiment, a syringe filled with a fluid composition is combined with a needle having a diameter of about 18 G to about 40 G, about 22 G to about 33 G, or about 26 G to about 40 G.

Aspects of the present specification provide, in part, a method having an optional step of sterilizing a syringe filled with a fluid composition disclosed in the present specification. As used herein, the term "sterilizing" refers to any method known in the art to effectively kill or eliminate transmissible agents without substantially altering of degrading a fluid composition disclosed in the specification. A sterilized fluid composition can remain stable for about 3 months to about 3 years. One method of sterilization of a filled syringe is by autoclave. Autoclaving can be accomplished by applying a mixture of heat, pressure and moisture to a sample in need of sterilization. Many different sterilization temperatures, pressures and cycle times can be used for this step. For example, the filled syringes may be sterilized at a temperature of at least about 120° C. to about 130° C. or greater. Moisture may or may not be utilized. The pressure applied is in some embodiments depending on the temperature used in the sterilization process. The sterilization cycle may be at least about 1 minute to about 20 minutes or more.

Another method of sterilization incorporates the use of a gaseous species which is known to kill or eliminate transmissible agents. Preferably, ethylene oxide is used as the sterilization gas and is known in the art to be useful in sterilizing medical devices and products.

A further method of sterilization incorporates the use of an irradiation source which is known in the art to kill or eliminate transmissible agents. A beam of irradiation is targeted at the syringe containing the HA composition, and the wavelength of energy kills or eliminates the unwanted transmissible agents. Preferable energy useful include, but is not limited to ultraviolet (UV) light, gamma irradiation, visible light, microwaves, or any other wavelength or band of wavelengths which kills or eliminates the unwanted transmissible agents, preferably without substantially altering of degrading the HA composition.

Thus, in an embodiment, a syringe filled with a fluid composition is sterilized. In aspects of this embodiment, a syringe filled with a fluid composition is sterilized by autoclaving, gas sterilization, or irradiation. In other aspects of this embodiment, a syringe filled with a fluid composition can remain stable after sterilization for about 3 months, about 6 months, about 9 months, about 12 months, about 18 months, about 24 months, about 30 months, or about 36 months. In yet other aspects of this embodiment, a syringe filled with a fluid composition can remain stable after sterilization for at least 3 months, at least 6 months, at least 9 months, at least 12 months, at least 18 months, at least 24 months, at least 30 months, or at least 36 months. In still other aspects of this embodiment, a syringe filled with a fluid composition can remain stable after sterilization for about 3 months to about 12 months, about 3 months to about 24 months, about 3 months to about 36 months, about 6 months to about 12 months, about 6 months to about 24 months, or about 6 months to about 36 months.

Aspects of the present specification provide, in part, a method of improving a condition of skin in an individual in need thereof, the method comprising the steps of administering a fluid composition disclosed in the present specification into a dermal region of the individual, wherein the administration improves the condition.

Aspects of the present invention provide, in part, a condition of skin. Non-limiting examples of a skin condition include dehydration, lack of skin elasticity, roughness, lack of skin tautness, skin stretch line and/or marks, skin paleness, skin wrinkles, and the like.

Aspects of the present invention provide, in part, improving a skin condition. Non-limiting examples of improving a skin condition include rehydrating the skin, providing increased elasticity to the skin, reducing skin roughness, making the skin tauter, reducing or eliminating stretch lines or marks, giving the skin better tone, shine, brightness and/or radiance to reduce paleness, reducing or eliminating wrinkles in the skin, providing wrinkle resistance to the skin, and the like.

Thus, in an embodiment, a method of treating a skin condition comprises the step of administering to an individual suffering from a skin condition a fluid composition comprising a matrix polymer and a stabilizing component, wherein the administration of the composition improves the skin condition, thereby treating the skin condition. In an aspect of this embodiment, a method of treating skin dehydration comprises the step of administering to an individual suffering from skin dehydration a fluid composition comprising a matrix polymer and a stabilizing component, wherein the administration of the composition rehydrates the skin, thereby treating skin dehydration. In another aspect of this embodiment, a method of treating a lack of skin elasticity comprises the step of administering to an individual suffering from a lack of skin elasticity a fluid composition comprising a matrix polymer and a stabilizing component, wherein the administration of the composition increases the elasticity of the skin, thereby treating a lack of skin elasticity. In yet another aspect of this embodiment, a method of treating skin roughness comprises the step of administering to an individual suffering from skin roughness a fluid composition comprising a matrix polymer and a stabilizing component, wherein the administration of the composition decreases skin roughness, thereby treating skin roughness. In still another aspect of this embodiment, a method of treating a lack of skin tautness comprises the step of administering to an individual suffering from a lack of skin tautness a fluid composition comprising a matrix polymer and a stabilizing component, wherein the administration of the composition makes the skin tauter, thereby treating a lack of skin tautness.

In a further aspect of this embodiment, a method of treating a skin stretch line or mark comprises the step of administering to an individual suffering from a skin stretch line or mark a fluid composition comprising a matrix polymer and a stabilizing component, wherein the administration of the composition reduces or eliminates the skin stretch line or mark, thereby treating a skin stretch line or mark. In another aspect of this embodiment, a method of treating skin paleness comprises the step of administering to an individual suffering from skin paleness a fluid composition comprising a matrix polymer and a stabilizing component, wherein the administration of the composition increases skin tone or radiance, thereby treating skin paleness. In another aspect of this embodiment, a method of treating skin wrinkles comprises the step of administering to an individual suffering from skin wrinkles a fluid composition comprising a matrix polymer and a stabilizing component, wherein the administration of the composition reduces or eliminates skin wrinkles, thereby treating skin wrinkles. In yet another aspect of this embodiment, a method of treating skin wrinkles comprises the step of administering to an individual a fluid composition comprising a matrix polymer and a stabilizing component, wherein the administration of the composition makes the skin resistant to skin wrinkles, thereby treating skin wrinkles.

Aspects of the present invention provide, in part, a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis is not part of the skin, and lies below the dermis. Its purpose is to attach the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

Aspects of the present invention provide, in part, an individual. As used herein, the term "individual" refers to any mammal including a human being.

Aspects of the present invention provide, in part, administering a fluid composition disclosed in the present specification. As used herein, the term "administering" means any delivery mechanism that provides a fluid composition comprising a matrix polymer and a stabilizing component to an individual that potentially results in a clinically, therapeutically, or experimentally beneficial result. The actual delivery mechanism used to administer a fluid composition disclosed in the present specification to an individual can be determined by a person of ordinary skill in the art by taking into account factors, including, without limitation, the type of skin condition, the location of the skin condition, the cause of the skin condition, the severity of the skin condition, the degree of relief desired, the duration of relief desired, the particular fluid composition used, the rate of excretion of the particular fluid composition used, the pharmacodynamics of the particular fluid composition used, the nature of the other compounds included in the particular fluid composition used, the particular route of administration, the particular characteristics, history and risk factors of the individual, such as, e.g., age, weight, general health and the like, or any combination thereof.

Thus, in an embodiment, a fluid composition comprising a matrix polymer and a stabilizing component is administered to a skin region of an individual. In an aspect of this embodiment, a fluid composition comprising a matrix polymer and a stabilizing component is administered to a skin region of an individual by injection. In another aspect of this embodiment, a fluid composition comprising a matrix polymer and a stabilizing component is administered to a skin region of an individual by injection into a dermal region. In aspects of this embodiment, a fluid composition comprising a matrix polymer and a stabilizing component is administered to a skin region of an individual by injection into, e.g., an epidermal-dermal junction region, a papillary region, a reticular region, or any combination thereof.

EXAMPLES

The following examples illustrate representative embodiments now contemplated, but should not be construed to limit the disclosed fluid compositions, methods of forming such fluid compositions, and methods of treating skin conditions using such fluid compositions.

Example 1

A Method of Making a Fluid Composition

This example illustrates how to make a fluid composition disclosed in the present specification.

To combine a stabilizing component with a physiologically-acceptable buffer to make a stabilizing component-buffered solution, 0.9 g of mannitol (Cooper Pharmaceutical, Inc.) was added to 1 L of a phosphate buffer solution (comprising 8.5 g NaCl, 0.563 g $NaH_2PO_4$, 0.045 g $Na_2HPO_4$, and water) in a 10 liter bottle, and mixed for 15 minutes. This step produces a stabilizing component-buffered solution comprising a phosphate buffer solution (pH 7.2) containing 0.9 mg/mL of mannitol.

To filter the stabilizing component-buffered solution, the mannitol-phosphate buffer solution made above was filtered on line with a 0.2 μm filter under pressure.

To combining a matrix polymer with the stabilizing component-buffered solution to hydrate the matrix polymer, about 60% of the mannitol-phosphate buffer solution was poured in a new bottle and uncrosslinked sodium hyaluronan polymer having a molecular weight between about 2.5 MDa and about 3.0 MDa was added to the mannitol-phosphate buffer solution. This was completed with the remaining 40% of the mannitol-phosphate buffer solution, giving a final concentration of uncrosslinked hyaluronan of about 13.5 mg/L. This composition was then gently, mechanically mixed at a speed of about 100 rpm to about 200 rpm for about 8 hours to about 12 hours at a cool ambient temperature of about 2° C. to about 8° C. The composition was then subjected to agitation by manually shaking the bottle containing the composition for about 1 minute, followed by a period of rest for about 30 minutes. This mixing step was repeated three additional times before the composition was then allowed to rest about 8 to about 12 hours.

To size a fluid composition, the fluid composition above was recirculated four times from one bottle into a second bottle thorough a narrow orifice having a diameter of about 3 mm and about 5 mm.

To degas a fluid composition, the composition described above was degassed for about four hours using standard device based on conventional techniques.

Example 2A

Stabilizing Component Reduces or Prevents Degradation of Matrix Polymer

This example illustrates that the addition of a stabilizing component reduces or prevents degradation of a matrix polymer included in a fluid composition disclosed in the present specification.

Fluid compositions made for testing were prepared as described in Example 1, except that 1) 1 mL of each fluid composition was made and the amount of mannitol added to the test fluid compositions was 0% (w/v) for control, 0.5% (w/v) and 5% (w/v).

Degradation of hyaluronan polymer included in the fluid compositions and rheological processing of the results were performed according to conventional methods. Resistance of hyaluronan polymer to degradation was assessed in fluid composition with and without mannitol and these compositions were compared by analyzing the time it took for the composition to reach a dynamic viscosity of 5 Pa·s [$T(\eta^*=5$ Pa·s)]. The degradation test was repeated twice and a mean dynamic viscosity [$T(\eta^*=5$ Pa·s)$_{mean}$] was calculated from the 2 tests (Table 4). In general, the shorter the time to reach a dynamic viscosity of 5 Pa·s [$T(\eta^*=5$ Pa·s)], the lower the resistance of hyaluronan polymer to degradation. Thus, to show that addition of mannitol to a fluid composition had a beneficial effect on resistance of hyaluronan polymer to breakdown, it was shown that $T(\eta^*=5$ Pa·s)$_{HA\ with\ mannitol}$>$T(\eta^*=5$ Pa·s)$_{HA\ without\ mannitol}$. For each fluid composition the results of the rheological test (values of G', G'', tan δ, $\eta^*$=f(time)+mathematical model of curve $\eta^*$=f(time)) were determined and the curves obtained (FIG. 1).

TABLE 4

| | Breakdown Test | | | | |
|---|---|---|---|---|---|
| Fluid Composition | Test | $T(\eta^*=5$ Pa·s) | Mean $T(\eta^*=5$ Pa·s) | Std. deviation | CV(%) |
| Hyaluronan (13.5 mg/L) | 1 | 747 | 1099 | 498 | 45 |
| | 2 | 1452 | | | |
| Hyaluronan (13.5 mg/L) 5% mannitol | 1 | 3351 | 3127 | 317 | 10 |
| | 2 | 2903 | | | |
| Hyaluronan (13.5 mg/L) 0.5% mannitol | 1 | 2933 | 2355 | 818 | 35 |
| | 2 | 1776 | | | |

Figure 1B:
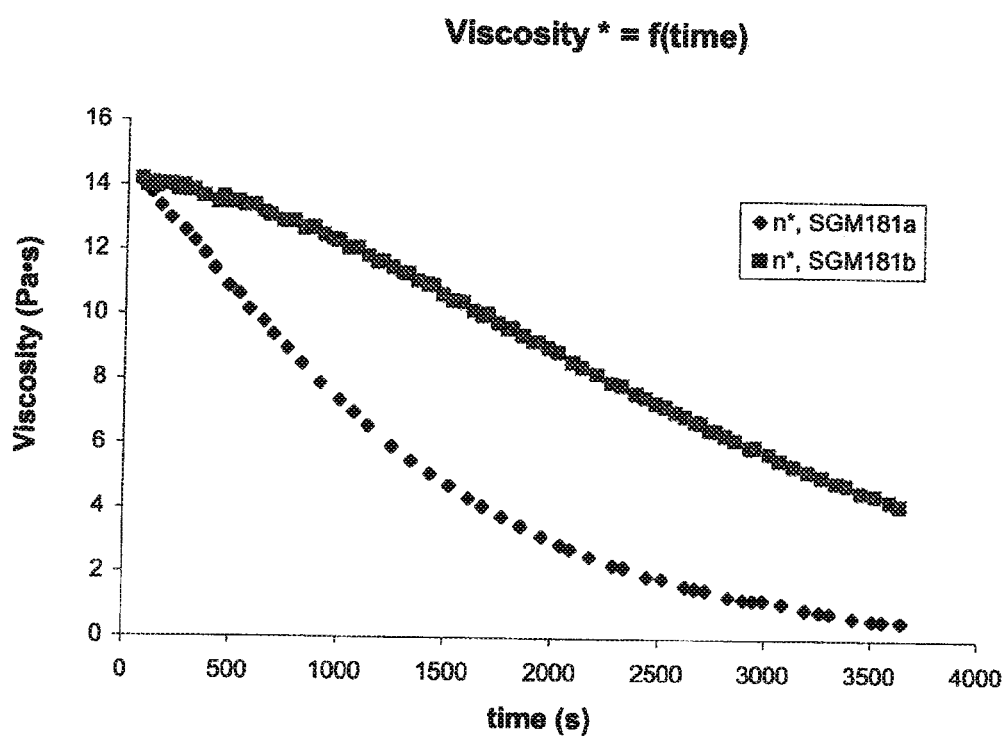
FIG. 1B shows a graph plotting dynamic viscosity over time. SGM181a is a fluid composition comprising 13.5 mg/mL hyaluronan polymer without mannitol (control) and SGM181b is a fluid composition comprising 13.5 mg/mL hyaluronan polymer and 5% mannitol.

As shown in Table 4, hyaluronan polymer was more resistant to degradation when mannitol was included in the fluid composition as compared to the resistance hyaluronan polymer in composition without mannitol (Table 4, FIG. 1). In fact, the higher the mannitol concentration in a fluid composition, the longer the time required for the hyaluronan polymer to degrade. As such, incorporating a stabilizing component like mannitol into a fluid composition allowed uncrosslinked hyaluronan polymer remained intact longer because the stabilizing component increased the resistance of hyaluronan polymer to degradation (FIG. 1). Thus, the addition of a stabilizing component to a fluid composition provided protection to a matrix polymer to degradation.

Example 2B

Effects of Stabilizing Component on Various Properties of Fluid Composition

This example illustrates the effects of a stabilizing component on various properties of a fluid composition disclosed in the present specification including fluid appearance, pH, osmolarity, and dynamic viscosity.

Fluid compositions made for testing were prepared as described in Example 1, except that 1) 1 mL of each fluid composition was made and the amount of mannitol added to the test fluid compositions was 0% (w/v) for control, 0.5% (w/v), 5% (w/v), 9% (w/v), and 17% (w/v).

The appearance of the fluid compositions was visually examined. Test compositions comprising 0% (w/v), 0.5% (w/v), 5% (w/v), and 9% (w/v) mannitol all appeared colorless and transparent, while the fluid composition comprising 17% (w/v) mannitol appeared white and cloudy (Table 5). These results indicate that mannitol was soluble in all fluid compositions tested, except for the composition comprising 17% (w/v) mannitol. Furthermore, it is known that mannitol solubility in water is 1 g mannitol/5.5 ml water, i.e. mass solubility of 15.4%. Taken together, these results indicate that fluid compositions comprising a matrix polymer can include about 15.4% mannitol before this polyol begins to precipitate out of solution.

The pH of the fluid compositions was measured using a pH meter. Test compositions comprising 0% (w/v), 0.5% (w/v), 5% (w/v), and 9% (w/v) mannitol all had a pH of 6.9, while the fluid composition comprising 17% (w/v) had a pH of 6.8 (Table 5). These results indicate that mannitol has no effect on the pH of a fluid composition because all pH values were within the measurement error range of the pH meter (±0.2).

The osmolarity of the fluid compositions was measured using an osmometer. Test compositions exhibited a wide range of osmolarity that was correlated with the amount of mannitol added to the composition (Table 5). In general, the osmolarity of a fluid composition increase as the amount of mannitol increased. The results indicated that a fluid composition comprising a matrix polymer and 0.5% mannitol preserved the required osmolarity for hyaluronan, namely an osmolarity range of about 270 mOsm/L to about 390 mOsm/L. It general, an osmolarity range of about 200 mOsm/L to about 400 mOsm/L is the range approved for viscoelastic ophthalmic devices.

The data obtained from the osmolarity test were further analyzed by linear regression. This analysis revealed that y=68.576x−17.118 and that $R^2$=0.9888. From this formula, it was calculated that the addition of 1% mannitol to a fluid composition comprising hyaluronan would increase the osmolarity of the composition by 52 mOsm/L to approximately 351 mOsm/L. As such, a fluid composition comprising a matrix polymer and 1% mannitol was an effective combination that balanced the opposite effects of improving a fluid composition's resistance to hyaluronan degradation and the increase in osmolarity upon addition of mannitol to the composition.

TABLE 5

Mannitol Effects on Properties of Fluid Compositions

| Fluid Composition | Appearance of Fluid Composition | pH | Osmolarity (mOsm/L) |
|---|---|---|---|
| Hyaluronan (13.5 mg/L) | Colorless and transparent | 6.9 | 299 |
| Hyaluronan (13.5 mg/L) Mannitol (0.5%) | Colorless and transparent | 6.9 | 333 |
| Hyaluronan (13.5 mg/L) Mannitol (5%) | Colorless and transparent | 6.9 | 589 |
| Hyaluronan (13.5 mg/L) Mannitol (9%) | Colorless and transparent | 6.9 | 918 |
| Hyaluronan (13.5 mg/L) Mannitol (17%) | White and cloudy | 6.8 | ND |

Figure 2:
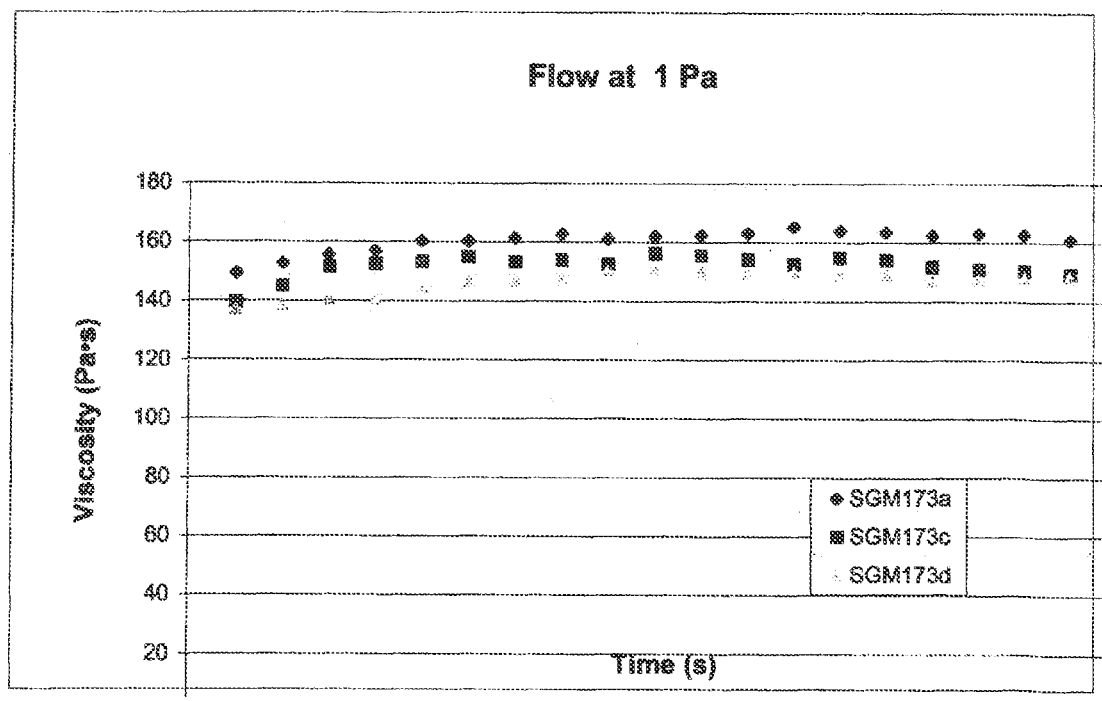
FIG. 2 is a graph showing the effects of increasing stabilizing concentration on the dynamic viscosity of a fluid composition comprising a matrix polymer. The graph plots dynamic viscosity (Pa·s) over time (s). SGM173a is a fluid composition comprising 13.5 mg/mL hyaluronan polymer without mannitol (control), SGM173c is a fluid composition comprising 13.5 mg/mL hyaluronan polymer and 5% mannitol and SGM173d is a fluid composition comprising 13.5 mg/mL hyaluronan polymer and 9% mannitol.

The dynamic viscosity of the fluid compositions was measured using a rheometer. Test compositions comprising 0% (w/v), 5% (w/v), and 9% (w/v) mannitol exhibited a consistent dynamic viscosity over time and all within 20 Pa·s of each other at 1 Pa (FIG. 2). The mean dynamic viscosity of these three fluid compositions was as follows: compositions comprising 0% (w/v) mannitol had a mean dynamic viscosity of 162 Pa·s; compositions comprising 5% (w/v) mannitol had a mean dynamic viscosity of 152 Pa·s; compositions comprising 9% (w/v) mannitol had a mean dynamic viscosity of 148 Pa·s. These results indicate that the effect of a stabilizing component was negligible because the addition of mannitol in an amount less than or equal to about 9% only resulted in a change in dynamic viscosity of about 20 Pa·s at 1 Pa.

Example 3

Effects of Sterilization on Fluid Compositions Comprising a Stabilizing Component This example illustrates the effects of sterilization on various properties of a fluid composition disclosed in the present specification including pH, dynamic viscosity and stability of stabilizing component.

Fluid compositions made for testing were prepared as described in Example 1, except that 1) 1 mL of each fluid composition was made and the amount of mannitol added to the test fluid compositions was 0% (w/v) and 1.1% (w/v). Fluid compositions prepared above were filled in a glass syringe and sterilized by autoclaving at 130° C. for 3 minutes.

The pH of the fluid compositions was measured using a pH meter. These results indicate that sterilization had no effect on the pH of a fluid composition because all pH values were within the measurement error range of the pH meter (±0.2) (Table 6).

The dynamic viscosity of the fluid compositions was measured before and after sterilization using a rheometer. The difference in viscosity before and after sterilization was 54 Pa·s for fluid compositions without mannitol and 61 Pa·s for fluid compositions comprising 1.1% (w/v) mannitol (Table 6). These results indicate that the addition of a stabilizing component had a negligible effect on dynamic viscosity because the difference between the two compositions was within the measurement error range of the rheometer (±10%). As such, there was no significant difference in dynamic viscosity of the fluid compositions before and after sterilization.

The chemical and physical stability of mannitol after sterilization was determined by autoclaving 25% Mannitol (Invenex Pharmaceuticals, Itasca, Ill.) five times at 121° C. for 15 minutes. The results indicate that mannitol was chemically and physically stable after this sterilization regime.

TABLE 6

Effects of Sterilization on Properties of Fluid Compositions

| | | Fluid Composition | |
|---|---|---|---|
| Sterilization | Composition Property | Hyaluronan (13.5 mg/L) | Hyaluronan (13.5 mg/L) Mannitol (1.1%) |
| Before sterilization | Dynamic viscosity at 1 Pa | 102 Pa · s | 118 Pa · s |
| | pH | 7.1 | 7.0 |
| After sterilization | Dynamic viscosity at 1 Pa | 48 Pa · s | 57 Pa · s |
| | pH | 7.1 | 7.0 |

Example 4

Determining the Stability of Fluid Composition-Filled Syringe

This example illustrates how to determine the long-term stability of a fluid composition disclosed in the present specification.

Fluid compositions were prepared as described in Example 1, except that the amount of mannitol added to the test fluid compositions was about 1% (w/v). The degassed fluid composition was then filled into a glass syringe and sterilized by autoclaving at 130° C. for 3 minutes.

The resulting composition-filled syringes will be stored at about 2° C. to about 8° C. and at about 18° C. to about 22° C. to determine shelf life of the fluid compositions. The stored compositions will be tested for various properties including dynamic viscosity, pH appearance and osmolarity at 3 months, 6 months, 9 months, 12 months, 18 months, 24 months, 30 months, and 36 months. These tests will determine the stability of fluid composition-filled syringes and as such the shelf life of such products.

Example 5

Safety and Efficacy Study of Fluid Composition

This example illustrates the safety and efficacy of a fluid composition disclosed in the present specification.

Fluid compositions were prepared as described in Example 1, except that the amount of mannitol added to the test fluid compositions was about 1% (w/v). The degassed fluid composition was then filled into a glass syringe and sterilized by autoclaving at 130° C. for 3 minutes.

The study included 39 individuals and comprised men and women between the ages of 30 and 45 years. All baseline data including consent, demographics, adverse events and skin evidence was collected from each individual before the study began. After the baseline visit, each individual was subdermally injected with the fluid composition described above and this was considered day 0 (D0). Follow-up visits took place at day 15 (D15±7 days) for the second injection, at day 30 (D30±7 days) for the third injection and finally at day 60 (D60±7 days) for final assessment. Dermal administration was performed using either a depot injection method or picotage injection method. At each study visit, individuals were examined for adverse events and skin evidence, and a questionnaire was given to assess physician and subject satisfaction. The total study duration was 60 days.

The study evaluated efficacy of the compositions on hydration and elasticity of the skin after 60 days of use of the fluid composition on different skin areas including the region around the eye, the cheek region, the peri-oral region, and the neck region.

Skin measurements were assessed at each of the four visits from day 0 to day 60, on different areas, by Skin Evidence for IOMA™ (IntuiSkin, Research Triangle Park, N.C.). Skin Evidence for IOMA is a probe-based system that measures the physical and visual parameters of the skin. The Visio Probe uses its high-resolution sensor to capture with an extreme precision the skin images including wrinkles, sebum, hairiness, dark spots, and clogged pores/bacterial infection. The Physio Probe contains high-technology sensors and extracts in vivo the key characteristics of the skin including hydration, trans-epidermal water loss (TEWL), and the skin temperature.

For each individual administered the fluid composition using a depot injection method, the cheek, neck, peri-oral and eye regions were measured for hydration (%) at each visit from D0 to D60 by Skin Evidence for IOMA™ and a mean hydration was determined at each visit (Table 7). Coefficient of anisotropy (%), arithmetical roughness (Ra), and luminance (L) were also measured for each individual at each visit from D0 to D60 by Skin Evidence for IOMA™ and mean values calculated. Statistical analyses were performed using SAS® software version 9.1 (SAS Institute, Inc. Cary, N.C.). The results indicate that overall skin hydration of the cheek (p=0.0036), neck (p=0.0346) and peri-oral (p=0.0024) regions was significantly increased by the treatment with the fluid composition. In particular, skin hydration of the cheek region was significantly increased by D15 of treatment (mean of 55.8%) as compared to D0 (mean of 50.9%) and this improvement in skin condition was maintain through D30 of treatment (mean of 56.4%) as compared to D0 (mean of 50.9%, p=0.0262) and D60 of treatment (mean of 59.3%) as compared to D0 (mean of 50.9%, p=0.0021). In addition, skin hydration of the neck region was significantly increased by D15 of treatment (mean of 66.0%) as compared to D0 (mean of 59.0%) and this improvement in skin condition was maintain through D30 of treatment (mean of 66.5%) of as compared to D0 (mean of 59.0%, p=0.0022), and D60 of treatment (mean of 65.3%) as compared to D0 (mean of 59.0%, p=0.0448). Furthermore, skin hydration of the peri-oral region was significantly increased by D15 of treatment (mean of 58.9%) as compared to D0 (mean of 52.4%) and this improvement in skin condition was maintain through D30 of treatment (mean of 61.2%) as compared to D0 (mean of 52.4%, p=0.0041) and D60 of treatment (mean of 59.3%) as compared to D0 (mean of 52.4%, p=0.0467).

TABLE 7

Assessment of Fluid Composition on Hydration of Skin Regions (Depot Method)

| Skin Region | | Visit | | | | |
|---|---|---|---|---|---|---|
| | | D 0 | D 15 | D 30 | D 60 | P |
| Cheek | N | 23 | 20 | 17 | 18 | Mixed |
| | Mean | 50.9% ± 11.0% | 55.8% ± 10.5% | 56.4% ± 13.9% | 59.3% ± 11.4% | model |
| | Median | 54.3% | 57.7% | 55.6% | 58.5% | P = 0.0036 |
| | Min/Max | 29.1%/68.2% | 36.5%/72.7% | 28.0%/83.1% | 41.0%/76.1% | |
| Neck | N | 20 | 19 | 17 | 16 | Mixed |
| | Mean | 59.0% ± 9.4% | 66.0% ± 9.6% | 66.5% ± 11.9% | 65.3% ± 9.9% | model |
| | Median | 58.7% | 66.5% | 70.0% | 61.4% | P = 0.0346 |
| | Min/Max | 41.4%/74.7% | 48.4%/81.2% | 43.5%/83.2% | 47.4%/82.9% | |
| Peri-oral | N | 20 | 16 | 15 | 15 | Mixed |
| | Mean | 52.4% ± 13.5% | 58.9% ± 12.1% | 61.2% ± 14.8% | 59.3% ± 11.0% | model |
| | Median | 50.1% | 58.4% | 62.6% | 61.1% | P = 0.0024 |
| | Min/Max | 27.4%/79.6% | 37.1%/81.7% | 31.0%/80.6% | 37.6%/79.4% | |
| Eyes | N | 21 | 16 | 16 | 14 | Mixed |
| | Mean | 59.6% ± 12.2% | 62.9% ± 10.7% | 55.8% ± 14.3% | 61.4% ± 10.7% | model |
| | Median | 56.3% | 60.6% | 53.7% | 60.9% | P = 0.2808 |
| | Min/Max | 42.6%/81.4% | 45.4%/82.6% | 19.8%/80.8% | 42.4%/78.3% | |

For each individual administered the fluid composition using a picotage injection method, the cheek, neck, peri-oral and eye regions were measured for hydration (%) at each visit from D0 to D60 by Skin Evidence for IOMA™ and a mean hydration was determined at each visit. The results indicated that there was no statistically significant difference in the hydration of the cheek, neck, peri-oral, or eye regions of individuals administered the fluid compositions using the picotage injection method.

With respect to anisotropy, the results indicate an overall improvement of skin condition from the neck and peri-oral regions when the fluid composition was administered using a depot injection method. No statistically significant difference was observed in anisotropy when the fluid compositions were administered using a picotage injection method.

With respect to skin roughness, the results indicate an overall improvement of skin condition from the neck region. In particular, skin roughness of the neck region was significantly decreased by D30 of treatment (median of 16.7%) as compared to D0 (median of 13.9%, p=0.0001). No statistically significant difference was observed in skin roughness when the fluid compositions were administered using a picotage injection method.

No statistically significant differences in skin luminance were detected for any of the four regions examined using either the depot injection method or the picotage injection method.

Treatment was well-tolerated with all adverse events related to injection technique rather than to the product. All adverse events were transient, with a mean duration of 4 days, with no sequels.

Regarding questionnaires designed to evaluate physicians' assessment of treatment, physicians using the depot injection method assessed skin texture (roughness) as "improved" or "very improved" in 88.9% of individuals administered the fluid composition at D15, in 100% of individuals administered the fluid composition at D30, and in 95.7% of individuals administered the fluid composition at D60. Physicians using the depot injection method assessed skin brightness as "improved" or "very improved" in 74.1% of individuals administered the fluid composition at D15, in 87.5% of individuals administered the fluid composition at D30, and in 91.3% of individuals administered the fluid composition at D60. Physicians using the depot injection method assessed skin hydration as "improved" or "very improved" in 88.9% of individuals administered the fluid composition at D15, in 100% of individuals administered the fluid composition at D30, and in 95.7% of individuals administered the fluid composition at D60. Physicians using the depot injection method assessed skin appearance (color) as "improved" or "very improved" in 48.1% of individuals administered the fluid composition at D15, in 91.7% of individuals administered the fluid composition at D30, and in 91.3% of individuals administered the fluid composition at D60.

Regarding questionnaires designed to evaluate individuals' assessment of treatment, individuals administered the fluid composition using the depot injection method assessed skin texture (roughness) as "improved" or "very improved" in 72.0% of individuals administered the fluid composition at D15, in 94.7% of individuals administered the fluid composition at D30, and in 80.9% of individuals administered the fluid composition at D60. Individuals administered the fluid composition using the depot injection method assessed skin brightness as "improved" or "very improved" in 84.0% of individuals administered the fluid composition at D15, in 84.3% of individuals administered the fluid composition at D30, and in 85.7% of individuals administered the fluid composition at D60. Individuals administered the fluid composition using the depot injection method assessed skin hydration as "improved" or "very improved" in 84.0% of individuals administered the fluid composition at D15, in 94.8% of individuals administered the fluid composition at D30, and in 95.0% of individuals administered the fluid composition at D60. Individuals administered the fluid composition using the depot injection method assessed skin appearance (color) as "improved" or "very improved" in 36.0% of individuals administered the fluid composition at D15, in 42.1% of individuals administered the fluid composition at D30, and in 42.9% of individuals administered the fluid composition at D60.

Regarding questionnaires designed to evaluate individuals' assessment of injection method, 100% of individuals administered the fluid composition using the depot injection method assessed global aesthetic effect at day 60 of treatment as "improved" or "very improved", whereas only 14.3% of individuals administered the fluid composition using the picotage injection method assessed global aesthetic effect at day 60 of treatment as "improved" or "very improved." Likewise, 100% of individuals administered the fluid composition using the depot injection method assessed revitalization of skin at day 60 of treatment as "improved" or "very improved", whereas only 14.3% of individuals administered the fluid composition using the picotage injection method assessed revitalization of skin at day 60 of treatment as "improved" or "very improved." Similarly, 78.9% of individuals administered the fluid composition using the depot injection method assessed face fullness at day 60 of treatment as "improved" or "very improved", whereas none of individuals administered the fluid composition using the picotage injection method assessed face fullness as "improved" or "very improved." All told, 95% of individuals administered the fluid composition using the depot injection method were delighted with the treatment at day 60, whereas only 14.3% of individuals administered the fluid composition using the picotage injection method were delighted with the treatment at day 60.

Overall, the fluid compositions disclosed in the present specification have significant efficacy on skin hydration on the cheek, neck, and peri-oral regions; significant efficacy on skin anisotropy on the neck and peri-oral regions; and significant efficacy on skin roughness on the neck region. In addition evaluation of questionnaires indicate physician satisfaction of aesthetic results at each visit showed that skin texture, skin brightness, skin hydration and overall skin condition were "improved" or 'very improved' for greater than 80% of subjects at Day 60. Similarly, subject satisfaction indicated that skin roughness, skin brightness, skin hydration and number of fine wrinkles were "improved" or 'very improved' for greater than 80% of subjects.

In closing, it is to be understood that although aspects of the present specification have been described with reference to the various embodiments, one skilled in the art will readily appreciate that the specific examples disclosed are only illustrative of the principles of the subject matter disclosed in the present specification. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims.

Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A dermal filler for rehydrating skin, the composition comprising:
   a hyaluronan polymer consisting essentially of uncrosslinked hyaluronic acid having a mean molecular weight of at least 2,500,000 Da, the uncrosslinked hyaluronan polymer being at least 95% by weight of the total hyaluronan polymer present in the composition; and
   mannitol present in at about 0.5% (w/v) to about 5% (w/v) of the composition.

2. The dermal filler of claim 1, wherein the hyaluronan polymer is entirely free of a crosslinked hyaluronan polymer.

3. The dermal filler wherein the hyaluronan polymer is present in the filler at a concentration of about 11.5 mg/mL to about 15.5 mg/mL.

4. The dermal filler of claim 1, wherein the hyaluronan polymer is present in the filler at a concentration of about 13.5 mg/mL.

5. The dermal filler of claim 1 wherein the mannitol is present in the filler at about 0.8% (w/v) to about 1.2% (w/v).

6. The dermal filler of claim 1 wherein the mannitol is present in the filler at about 1% (w/v).

7. The dermal filler of claim 1, wherein the hyaluronan polymer is present in the filler at a concentration of about 13.5 mg/mL and the mannitol is present in the filler at about 1% (w/v).

8. The dermal filler of claim 1 wherein the mean molecular weight is about 2,500,000 Da to about 5,000,000 Da.

9. The dermal filler of claim 1 wherein the mean molecular weight is about 2,500,000 Da to about 3,500,000 Da.

10. The dermal filler of claim 1 wherein the mean molecular weight is at least 3,000,000 Da.

11. The dermal filler of claim 1 wherein the mean molecular weight is at least 3,500,000 Da.

12. The dermal filler of claim 1 wherein the mean molecular weight is at least 4,000,000 Da.

13. The dermal filler of claim 1 wherein the mean molecular weight is at least 4,500,000 Da.

14. The dermal filler of claim 1 wherein the mean molecular weight is at least 5,000,000 Da.

* * * * *

UNITED STATES PATENT AND TRADEMARK OFFICE
CERTIFICATE OF CORRECTION

PATENT NO. : 8,921,338 B2
APPLICATION NO. : 14/077980
DATED : December 30, 2014
INVENTOR(S) : Pierre F. Lebreton Page 1 of 2

It is certified that error appears in the above-identified patent and that said Letters Patent is hereby corrected as shown below:

On the Title page, item (56)

On the page 3, in column 2, under "Other Publications", line 26, delete "Breats" and insert -- Breast --, therefor.

On the page 3, in column 2, under "Other Publications", line 38, delete "Sponse:" and insert -- Sponge: --, therefor.

On the page 4, in column 1, under "Other Publications", line 64, delete "Institue" and insert -- Institute --, therefor.

On the page 4, in column 2, under "Other Publications", line 3, delete "Compunds" and insert -- Compounds --, therefor.

On the page 4, in column 2, under "Other Publications", line 19, delete "Plastric" and insert -- Plastic --, therefor.

On the page 5, in column 1, under "Other Publications", line 4, delete "etal" and insert -- et al., --, therefor.

On the page 5, in column 1, under "Other Publications", line 5, delete "Crosslinkedwith" and insert -- Crosslinked with --, therefor.

On the page 5, in column 1, under "Other Publications", line 5, delete "Glyol" and insert -- Glycol --, therefor.

On the page 5, in column 1, under "Other Publications", line 6, delete "Tetracrylates";" and insert -- Tetraacrylate"; --, therefor.

On the page 5, in column 1, under "Other Publications", line 15, delete "Viscoelstic" and insert -- Viscoelastic --, therefor.

On the page 5, in column 2, under "Other Publications", line 28, delete "Hyalruonic" and insert -- Hyaluronic --, therefor.

Signed and Sealed this
Twelfth Day of May, 2015

Michelle K. Lee
*Director of the United States Patent and Trademark Office*

CERTIFICATE OF CORRECTION (continued)
U.S. Pat. No. 8,921,338 B2

In the Specification

In column 6, line 66, delete "(BCD)," and insert -- (BCDI), --, therefor.

In column 7, line 1, delete "(NMDA)," and insert -- (HMDA), --, therefor.

In column 17, line 51, delete "OH." and insert -- OH· --, therefor.

In column 18, line 1, delete "(OH.)." and insert -- (OH·). --, therefor.

In column 18, line 47, delete "OH." and insert -- OH· --, therefor.

In column 24, in table 3, line 46, delete "4-phenylcoumarine" and insert -- 4-phenylcoumarin --, therefor.

In column 32, line 31, delete "Tan 6" and insert -- Tan δ --, therefor.

In column 33, line 48, delete "q" and insert -- η --, therefor.

In column 35, line 52, delete "ΣΦ Φi ηi Ci," and insert -- ΣΦi ηi Ci, --, therefor.